United States Patent
Siedlecki et al.

(10) Patent No.: US 10,266,609 B2
(45) Date of Patent: Apr. 23, 2019

(54) IMMUNOMODULATING BETA-1,6-D-GLUCANS

(71) Applicant: Innate Biotherapeutics, LLC, Newton, MA (US)

(72) Inventors: James Michael Siedlecki, Burlington, MA (US); Gabriel Oscar Reznik, Bedford, MA (US); John James Kane, Cambridge, MA (US); Hua Miao, Newton, MA (US); Arthur F. Kluge, Lincoln, MA (US); Ifat Rubin-Bejerano, Newton, MA (US)

(73) Assignee: Innate Biotherapeutics, LLC, Newton, MA (US)

( * ) Notice: Subject to any disclaimer, the term of this patent is extended or adjusted under 35 U.S.C. 154(b) by 29 days.

(21) Appl. No.: 15/309,313

(22) PCT Filed: May 8, 2015

(86) PCT No.: PCT/US2015/029916
§ 371 (c)(1),
(2) Date: Nov. 7, 2016

(87) PCT Pub. No.: WO2015/172040
PCT Pub. Date: Nov. 12, 2015

(65) Prior Publication Data
US 2017/0081428 A1 Mar. 23, 2017

Related U.S. Application Data

(60) Provisional application No. 61/990,337, filed on May 8, 2014.

(51) Int. Cl.
| | | |
|---|---|---|
| C07H 1/00 | (2006.01) |
| C08B 37/00 | (2006.01) |
| C07H 3/06 | (2006.01) |
| C07H 5/04 | (2006.01) |
| C07H 13/04 | (2006.01) |
| C07H 15/04 | (2006.01) |
| C07H 15/18 | (2006.01) |
| C07H 15/203 | (2006.01) |
| C07H 15/26 | (2006.01) |
| C07H 19/044 | (2006.01) |
| C07H 19/048 | (2006.01) |

(52) U.S. Cl.
CPC ........... *C08B 37/0024* (2013.01); *C07H 3/06* (2013.01); *C07H 5/04* (2013.01); *C07H 13/04* (2013.01); *C07H 15/04* (2013.01); *C07H 15/18* (2013.01); *C07H 15/203* (2013.01); *C07H 15/26* (2013.01); *C07H 19/044* (2013.01); *C07H 19/048* (2013.01)

(58) Field of Classification Search
None
See application file for complete search history.

(56) References Cited

U.S. PATENT DOCUMENTS

| | | |
|---|---|---|
| 2004/0127458 A1 | 7/2004 | Hunter et al. |
| 2006/0147415 A1 | 7/2006 | Mousa et al. |
| 2011/0177532 A1 | 7/2011 | Rubin-Bejerano et al. |

FOREIGN PATENT DOCUMENTS

| | | |
|---|---|---|
| CN | 1188770 A | 7/1998 |
| WO | WO-2007/112567 A1 | 10/2007 |
| WO | WO-2008/057501 A2 | 5/2008 |
| WO | WO-2015/172040 A2 | 11/2015 |

OTHER PUBLICATIONS

Hattori et al. Carbohydrate Research (2013), vol. 366, pp. 6-16.*
Wood J. Exp. Med. (1981), vol. 154, pp. 432-449.*
International Search Report for PCT/US15/39916, 4 pages (dated Oct. 23, 2015).
PubChem 439737—1,6-beta-D-Glucan, National Center for Biotechnology Information, 10 pages (created Jun. 24, 2005).
PubChem CID 25270032, National Center for Biotechnology Information, 9 pages (created May 25, 2009).
Written Opinion for PCT/US15/39916, 9 pages (dated Oct. 23, 2015).
International Preliminary Report on Patentability for International Application No. PCT/US15/29916, dated Nov. 8, 2016.
Mousa et al., "Synthetic oligosaccharide stimulates and stabilizes angiogenesis: structure-function relationships and potential mechanisms," J Cardiovasc Pharmacol, 48(2): 6-13 (2006).
Partial Supplementary European Search Report issued by the European Patent Office in corresponding Application No. 1578970.1, dated Nov. 17, 2017.
Rubin-Bejerano et al., "Phagocytosis by human neutrophils is stimulated by a unique fungal cell wall component," Cell Host Microbe, 2(1):55-67 (2007).
Zhang et al., "Synthesis and applications of a light-fluorous glycosyl donor," J Org Chem, 74(6):2594-2597 (2009).

* cited by examiner

*Primary Examiner* — Patrick T Lewis
(74) *Attorney, Agent, or Firm* — Foley Hoag LLP

(57) ABSTRACT

This invention relates to modifications of β-1,6-D-glucans, e.g., structures according to Formula (I), and the ability of these compositions to modulate an immune response.

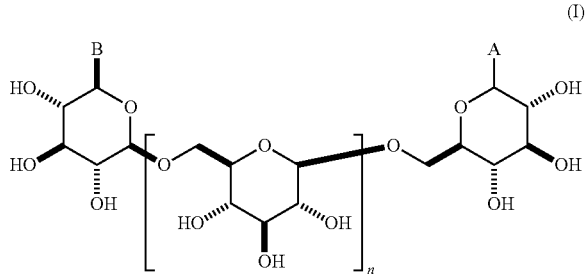

19 Claims, No Drawings

IMMUNOMODULATING BETA-1,6-D-GLUCANS

CROSS-REFERENCE TO RELATED APPLICATIONS

This application claims priority from U.S. Provisional Patent Application No. 61/990,337, filed May 8, 2014, the disclosure of which is hereby incorporated by reference in its entirety.

FIELD OF THE INVENTION

This invention relates to modifications of β-1,6-D-glucans and the ability of these compositions to modulate an immune response.

BACKGROUND OF THE INVENTION

The cell walls of fungi evoke a powerful immune-stimulatory response. More than 50% of the cell walls of *Candida albicans* is composed of an inner layer of β-1,3/1,6-D-glucan covalently linked to a variety of cell surface mannoproteins [Klis, F. M. et al. FEMS Microbiol. Rev. 26, 239-259, 2002]. Preparations of these β-1,3/1,6-glucans act as immunostimulants [Lee, J. N. et al. Biosci. Biotechnol. Biochem. 65, 837-841, 2001; Sakurai, T. et al. J. Leukoc. Biol. 60, 118-124, 1996].

Specifically, β-1,6-D-glucan, more than β-1,3-D-glucan, has been shown to recruit and activate human neutrophils [Rubin-Bejerano I. et al., Cell Host Microbe. 2(1): 55-67, 2007]. The activation is mediated by endogenous anti-β-1,6-glucan antibodies, mostly of the IgG2 isotype [PCT/US09/42117], as well as C3 proteolytic fragments of the complement system [Rubin-Bejerano I. et al., Cell Host Microbe. 2(1): 55-67, 2007]. Therapeutic agents that include β-1,6-D-glucans can be conjugated to a targeting moiety (e.g., a cancer targeting antibody; see, e.g., PCT/US07/23307), as well as methods of using these conjugates as therapeutic agents, e.g., to treat various cancers.

Accordingly, compositions comprising β-1,6-D-glucan oligosaccharides of specific sizes can be useful for the preparation of therapeutic agents. In some embodiments, the oligosaccharides have been modified in a way that would allow conjugation to targeting moieties. Such chemically modified β-1,6-D-glucans have also been assayed for binding to the endogenous anti-β-1,6-D-glucan antibodies, thereby maintaining the desired function.

SUMMARY OF THE INVENTION

The present invention provides novel β-1,6-D-glucans and compositions thereof. Such compositions provide the ability to be recognized by IgG2 antibodies.

In some embodiments, the compositions comprise oligomeric β-1,6-D-glucan compositions represented by the general formula (I),

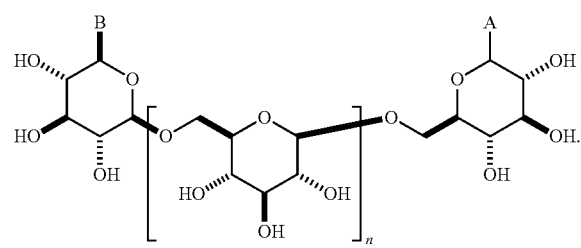

(I)

In general formula (I), n is an integer from 1 to 18 (e.g., an integer from 1 to 18 or an integer from 2 to 18), and groups A and B are each independently any of the moieties described herein.

In some embodiments, n is 1, 2, 3, 4, 5, 6, 7, 8, 9, 10, 11, 12, 13, 14, 15, 16, 17, or 18. In certain embodiments, n is 2, 3, 4, 5, 6, 7, 8, 9, 10, 11, 12, 13, 14, 15, 16, 17, or 18. In other embodiments, n is 8, 9, 10, 11, 12, 13, 14, 15, 16, 17, or 18.

In other embodiments, group B is $CH_2OH$.

In still other embodiments, group B is CHO.

In certain embodiments, group B is $CO_2H$.

In some embodiments, group A is α. In other embodiments, group A is β.

In other embodiments, group A is OR or SR, wherein R is alkyl, alkenyl, alkynyl, aryl, heteroaryl, or heteroaliphatic. In some embodiments, group A is SR. In other embodiments, group A is OR. In some embodiments, R is alkyl, alkenyl, or alkynyl. In other embodiments, R is aryl or heteroaryl. In still other embodiments, R is heteroaliphatic (e.g., heteroalkyl). In some embodiments, R is alkyl. In other embodiments, R is aryl. In certain embodiments, group A is OR, and R is alkyl. In some embodiments, group A is OR, and R is alkyl, aryl, or heteroaliphatic. In certain embodiments, group A is SR, and R is alkyl. In some embodiments, group A is OR, and R is alkyl, aryl, or heteroaliphatic. In some embodiments, R is unsubstituted. In other embodiments, R is substituted (e.g., R comprises an azide moiety, a halogen (e.g., F, Cl, Br, or I), or a carboxylic acid ($CO_2H$) moiety).

In some embodiments, group A is $O(CH_2CH_2O)_a CH_2CH_2Cl$, wherein a is 0, 1, 2, 3, 4, or 5.

In some embodiments, group A is $O(CH_2CH_2O)_a CH_2CH_2N_3$, wherein a is 0, 1, 2, 3, 4, or 5.

In some embodiments, group A is $O(CH_2CH_2O)_a CH_2CH_2CO_2H$, wherein a is 0, 1, 2, 3, 4, or 5.

In some embodiments, group A is $S(CH_2CH_2O)_a CH_2CH_2Cl$, wherein a is 0, 1, 2, 3, 4, or 5.

In some embodiments, group A is $S(CH_2CH_2O)_a CH_2CH_2N_3$, wherein a is 0, 1, 2, 3, 4, or 5.

In some embodiments, group A is $S(CH_2CH_2O)_a CH_2CH_2CO_2H$, wherein a is 0, 1, 2, 3, 4, or 5.

In still other embodiments, group A is a 6-O-substituted-D-glucosamine (W), or a 6-O-substituted-C-glycoside (X),

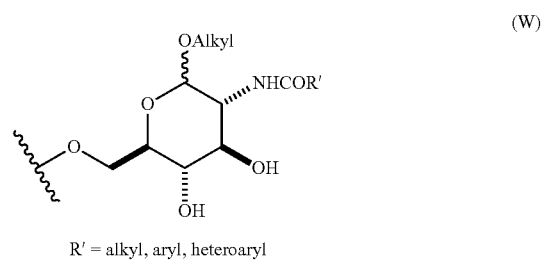

(W)

R' = alkyl, aryl, heteroaryl

-continued

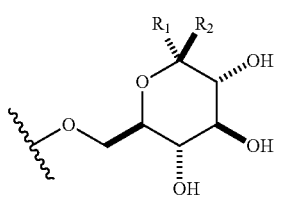

R₁ = H; R₂ = alkenyl, alkynyl, or
heteroaliphatic (e.g.,
O(CH₂CH₂O)ₐCH₂CO₂H)
or
R₂ = H; R₁ = alkenyl, alkynyl, or
heteroaliphatic (e.g.,
O(CH₂CH₂O)ₐCH₂CO₂H)

a = 0, 1, 2, 3, 4, or 5

In some embodiments of W, said OAlkyl moiety comprises an unsubstituted alkyl group. In other embodiments, said OAlkyl moiety comprises a substituted alkyl group. In other embodiments, R' comprises an unsubstituted alkyl, aryl, or heteroaryl group. In other embodiments, R' comprises a substituted alkyl, aryl, or heteroaryl group. In some embodiments of X, R₁ or R₂ is an unsubstituted alkenyl or unsubstituted alkynyl group. In other embodiments, R₁ or R₂ is a substituted alkenyl or substituted alkynyl group. In some embodiments of X, R₁ or R₂ is O(CH₂CH₂O)ₐCH₂CO₂H. In other embodiments, a is 0, 1, 2, 3, 4, or 5.

In some embodiments, n is 1, 2, 3, 4, 5, 6, 7, 8, 9, 10, 11, 12, 13, 14, 15, 16, or 17; and group A is

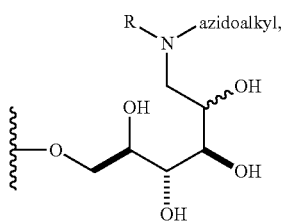

wherein R is H, alkyl, or aryl, and azidoalkyl is an alkyl group containing an azide moiety. In some embodiments, R is H. In other embodiments, R is unsubstituted alkyl or substituted alkyl. In still other embodiments, R is unsubstituted aryl or substituted aryl. In certain embodiments, said azidoalkyl does not comprise additional substituents. In other embodiments, said azidoalkyl comprises additional substituents as described herein.

In some embodiments, n is 1, 2, 3, 4, 5, 6, 7, 8, 9, 10, 11, 12, 13, 14, 15, 16, or 17; and group A is

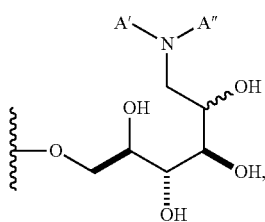

wherein A' is alkyl, aryl, or heteroaryl; and A" is carboxy alkyl, carboxy aryl, or carboxy heteroaryl. In some embodiments, carboxy alkyl represents a residue formed from an aliphatic amino acid; carboxy aryl represents a residue formed from an aromatic amino acid; and carboxy heteroaryl represents a residue formed from a heteroaromatic amino acid. In other embodiments, n is 2, 3, 4, 5, 6, 7, 8, 9, 10, 11, 12, 13, 14, 15, 16, or 17. In some embodiments, n is 1, 2, 3, 4, 5, 6, 7, 8, 9, 10, 11, 12, 13, 14, 15, 16, 17; and group A is

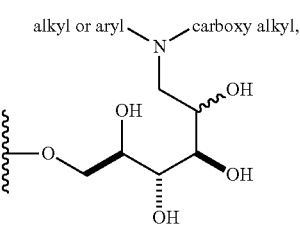

wherein "carboxy alkyl" represents an amino acid residue. In some embodiments, A' is an unsubstituted or a substituted alkyl group. In other embodiments, A' is an unsubstituted or a substituted aryl group. In other embodiments, A' is an unsubstituted or a substituted heteroaryl group. In certain embodiments, A' is an unsubstituted or a substituted carboxyl aryl group. In still other embodiments, A' is an unsubstituted or a substituted carboxylheteroaryl group.

In some embodiments, n is 1, 2, 3, 4, 5, 6, 7, 8, 9, 10, 11, 12, 13, 14, 15, 16, 17; and group A is

wherein A' is alkyl, aryl, or heteroaryl; and "aminoalkyl" represents an alkyl group containing an amino moiety. In some embodiments, the aminoalkyl represents a residue formed from an aliphatic bis-amine. In some embodiments, A' is alkyl or aryl. In some embodiments, group A comprises an unsubstituted or a substituted alkyl group. In other embodiments, group A comprises an unsubstituted or a substituted aryl group.

In other embodiments, n is 1, 2, 3, 4, 5, 6, 7, 8, 9, 10, 11, 12, 13, 14, 15, 16, 17; and group A is

In some embodiments, the alkyl covalently bonded to the nitrogen atom is unsubstituted. In other embodiments, the alkyl covalently bonded to the nitrogen atom is substituted. In certain embodiments, the O-alkyl moiety comprises an unsubstituted alkyl group. In other embodiments, the O-alkyl moiety comprises a substituted alkyl group. In some embodiments, the O-aryl moiety comprises an unsubstituted aryl group. In other embodiments, the O-aryl moiety comprises a substituted aryl group.

In some embodiments, group A is $OCH_3$, $SCH_2CH_3$, $OCH_2CH_2Cl$, $OCH_2CH_2N_3$, $SC_6H_5$,

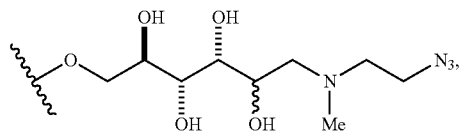

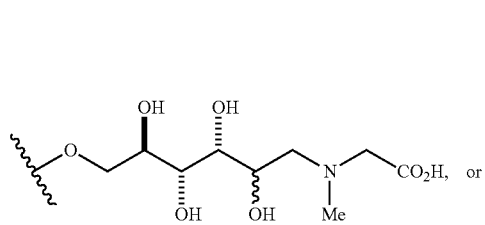

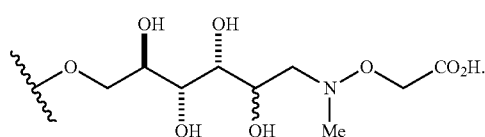

In one embodiment, this invention provides a composition comprising an α- or β-oriented O-glycoside according to formula (Ia), wherein n is an integer between 2-18, the group A is OR and selected from a group that includes O-alkyl, —O-alkenyl, O-alkynyl, O-alkylene, O-alkynylene, O-aryl, O-heteroaryl, a 6-O-substituted-D-glucosamine (W), or a 6-O-substituted-C-glycoside (X); and the group B is $CH_2OH$.

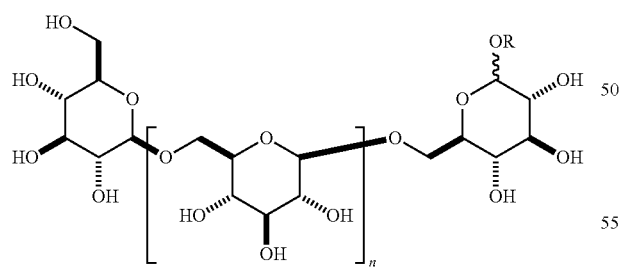

(Ia)

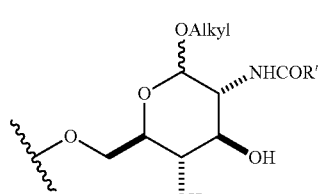

(W)

R' = alkyl, aryl, heteroaryl

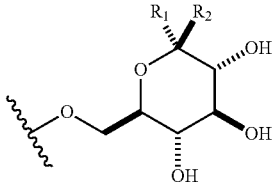

(X)

$R_1$ = H; $R_2$ = alkenyl, alkynyl, or heteroaliphatic (e.g., $O(CH_2CH_2O)_aCH_2CO_2H$)
or
$R_2$ = H; $R_1$ = alkenyl, alkynyl, or heteroaliphatic (e.g., $O(CH_2CH_2O)_aCH_2CO_2H$)

a = 0, 1, 2, 3, 4, or 5

In some embodiments, the alkyl, alkenyl, alkynyl, alkylene, alkynylene, aryl, or heteroaryl in group A is unsubstituted. In other embodiments, the alkyl, alkenyl, alkynyl, alkylene, alkynylene, aryl, or heteroaryl in group A is substituted. In other embodiments, group A is α-oriented. In still other embodiments, group A is β-oriented. In some embodiments, n is 1, 2, 3, 4, 5, 6, 7, 8, 9, 10, 11, 12, 13, 14, 15, 16, 17, or 18. In other embodiments, n is 2, 3, 4, 5, 6, 7, 8, 9, 10, 11, 12, 13, 14, 15, 16, 17, or 18.

In another embodiment, this invention provides a composition comprising an S-glycoside according to general formula (Ib),

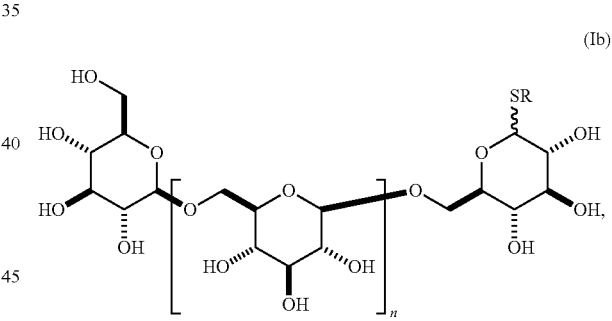

(Ib)

wherein n is an integer between 1-18 (e.g., 2-18), the group A is an α- or β-oriented SR selected from S-alkyl, S-alkenyl, S-alkynyl, S-alkylene, S-alkynylene, S-aryl or S-heteroaryl, and the group B is $CH_2OH$. In some embodiments, the alkyl, alkenyl, alkynyl, alkylene, alkynylene, aryl, or heteroaryl in group A is unsubstituted. In other embodiments, the alkyl, alkenyl, alkynyl, alkylene, alkynylene, aryl, or heteroaryl in group A is substituted as described herein. In other embodiments, group A is α-oriented. In still other embodiments, group A is β-oriented. In some embodiments, n is 1, 2, 3, 4, 5, 6, 7, 8, 9, 10, 11, 12, 13, 14, 15, 16, 17, or 18. In still other embodiments, n is 2, 3, 4, 5, 6, 7, 8, 9, 10, 11, 12, 13, 14, 15, 16, 17, or 18.

In another embodiment, this invention provides a composition comprising an O-glycoside according to formula (Ic),

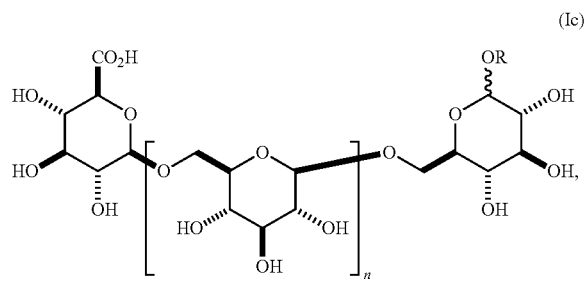

(Ic)

wherein n is an integer between 1-18 (e.g., 2-18), the group A is an α- or β-oriented OR that is O-alkyl, and group B is CO₂H. In some embodiments, group A comprises an unsubstituted alkyl group. In other embodiments, group A comprises a substituted alkyl group. In other embodiments, group A is α-oriented. In still other embodiments, group A is β-oriented. In some embodiments, n is 1, 2, 3, 4, 5, 6, 7, 8, 9, 10, 11, 12, 13, 14, 15, 16, 17, or 18. In still other embodiments, n is 2, 3, 4, 5, 6, 7, 8, 9, 10, 11, 12, 13, 14, 15, 16, 17, or 18.

In yet another embodiment, this invention provides a composition comprising an O-glycoside (Id),

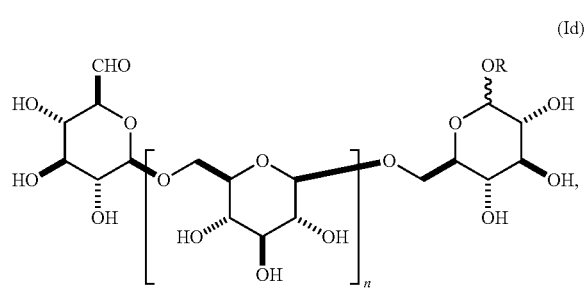

(Id)

wherein n is an integer between 1-18 (e.g., 2-18), group A is an α- or β-oriented OR group that is O-alkyl, and group B is CHO. In some embodiments, group A comprises an unsubstituted alkyl group. In other embodiments, group A comprises a substituted alkyl group. In other embodiments, group A is α-oriented. In still other embodiments, group A is β-oriented. In some embodiments, n is 1, 2, 3, 4, 5, 6, 7, 8, 9, 10, 11, 12, 13, 14, 15, 16, 17, or 18. In still other embodiments, n is 2, 3, 4, 5, 6, 7, 8, 9, 10, 11, 12, 13, 14, 15, 16, 17, or 18.

In other embodiments, the invention provides a composition comprising a dendrimer molecule, wherein said dendrimer comprises repeating units of any of the β-1,6-D-glucan moieties described herein linked to a common core (e.g., an alkyl, aryl, or heteroaryl common core) through linkages such as glycosidic linkages.

In yet another embodiment, this invention provides a composition comprising a dendrimer molecule (Ie),

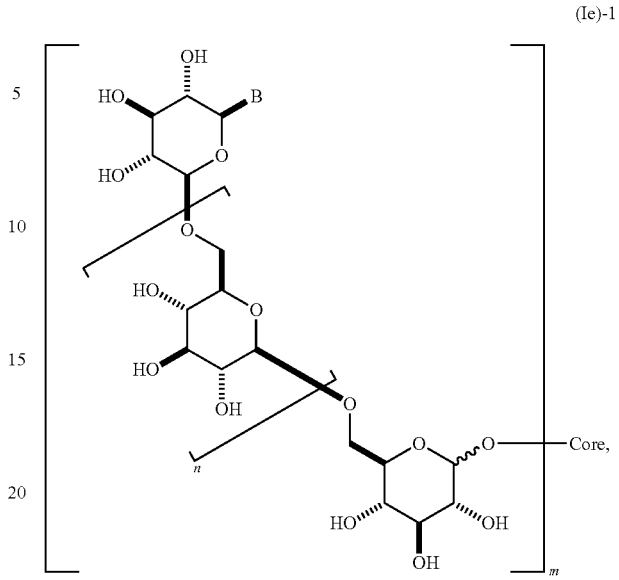

(Ie)-1 containing 2 or more β-1,6-D-glucan moieties as described by the repeating unit of formula (Ie)-1, wherein group B is as described herein and said glucan moieties are linked to a substituted alkyl, substituted aryl or substituted heteroaryl common core through glycosidic linkages; n is an integer from 1-20 (e.g., 2 to 20); and m is an integer from 2 to 6. In some embodiments, n is 1, 2, 3, 4, 5, 6, 7, 8, 9, 10, 11, 12, 13, 14, 15, 16, 17, 18, 19, or 20. In still other embodiments, n is 2, 3, 4, 5, 6, 7, 8, 9, 10, 11, 12, 13, 14, 15, 16, 17, or 18. In other embodiments, m is 2, 3, 4, 5, or 6. In some embodiments, said glycosidic linkage is α. In other embodiments, said glycosidic linkage is β. In some embodiments, B is CH₂OH, CO₂H, CHO, optionally substituted amino, or carboxamide (e.g., CO (optionally substituted amino)). In other embodiments, said dendrimer molecule has a structure according to formula (Ie)-2,

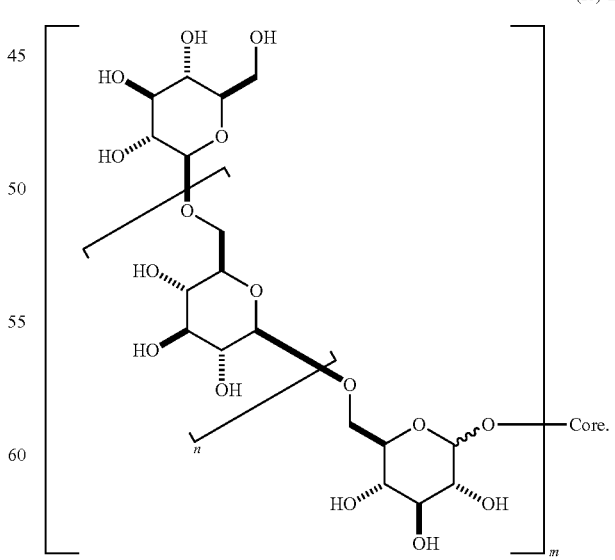

(Ie)-2

In yet another embodiment, this invention provides a composition comprising a dendrimer molecule (If),

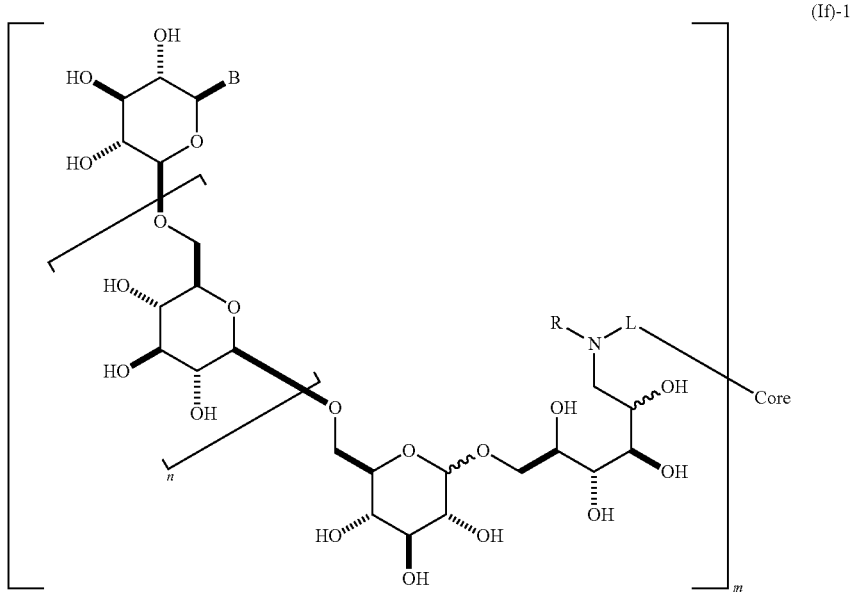

(If)-1 containing 2 or more β-1,6-D-glucan moieties as described by the repeating unit of formula (If)-1, wherein group B is as described herein and said glucan moieties are linked to a substituted alkyl, substituted aryl or substituted heteroaryl common core through optionally substituted linkage L; n is an integer from 1 to 20; R is H, alkyl, or aryl; and m is an integer from 2 to 6. In some embodiments, n is 1, 2, 3, 4, 5, 6, 7, 8, 9, 10, 11, 12, 13, 14, 15, 16, 17, 18, 19, or 20. In other embodiments, m is 2, 3, 4, 5, or 6. In some embodiments, said glycosidic linkage is α. In other embodiments, said glycosidic linkage is β. In some embodiments, B is $CH_2OH$, $CO_2H$, CHO, optionally substituted amino, or carboxamide (e.g., CO (optionally substituted amino)). In other embodiments, the invention provides a composition comprising a dendrimer molecule according to formula (If)-2,

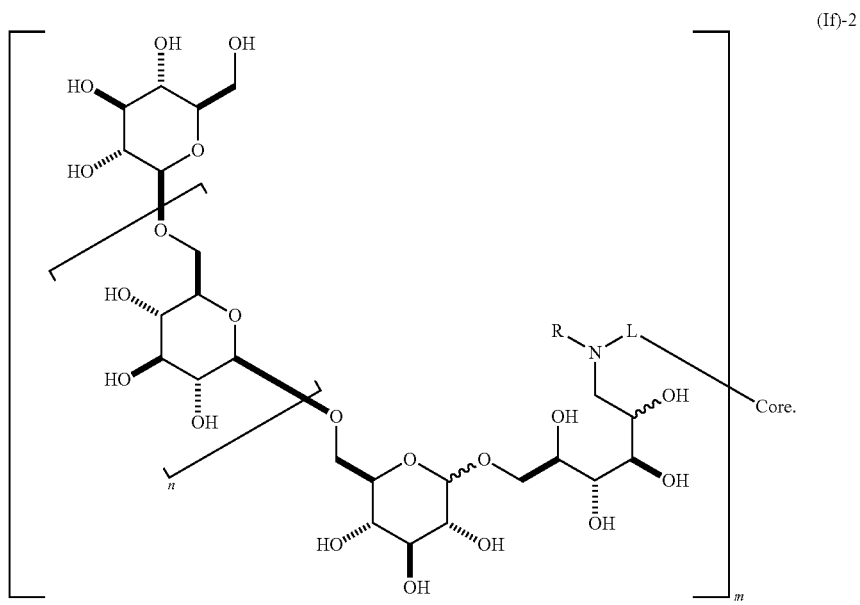

(If)-2

In some embodiments, the linkage between the glucan moiety and the core comprises or is formed from any of the R moieties described herein. In certain embodiments, the linkage (e.g., linkage L) comprises an alkylene, alkenylene, alkynylene, heteroalkylene, heteroalkenylene, or heteroalkynylene moiety. In further embodiments, the linkage (e.g., linkage L) is formed from an azidoalkyl group, a carboxy alkyl group, a carboxy aryl group, an O-alkyl group, or an O-aryl group. In still other embodiments, the linkage (e.g., linkage L) is a covalent bond between the repeating unit and the core.

In other embodiments, said dendrimer molecule has a structure according to formula (Ig),

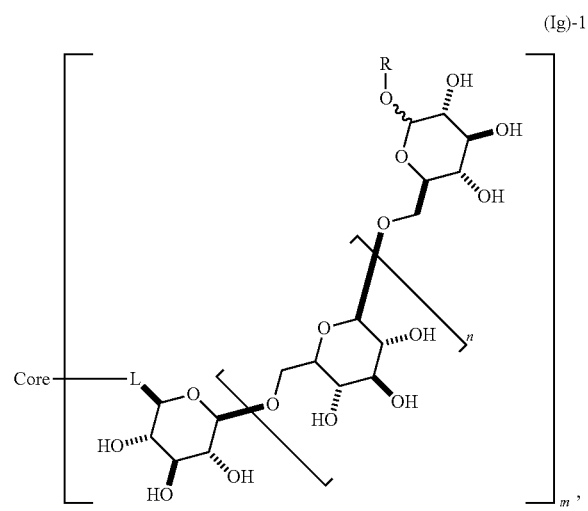

(Ig)-1 containing 2 or more β-1,6-D-glucan moieties as described by the repeating unit of formula (Ig)-1, wherein said glucan moieties are linked through L, which is a carboxamide or heteroalkylene moiety, to a substituted alkyl, substituted aryl or substituted heteroaryl common core; n is an integer from 1 to 20; R is alkyl, aryl, or heteteroaryl; and m is an integer from 2 to 6. In some embodiments, n is 1, 2, 3, 4, 5, 6, 7, 8, 9, 10, 11, 12, 13, 14, 15, 16, 17, 18, 19, or 20. In other embodiments, m is 2, 3, 4, 5, or 6. In some embodiments, R is alkyl. In some embodiments, R is aryl. In some embodiments, R is heteroaryl. In some embodiments, L is a carboxamide moiety. In other embodiments, L is a methyleneamine moiety. In other embodiments, L is $CH_2NR'$—, where R' is H, alkyl, or aryl. In still other embodiments, L is —$C(O)NR'$—, where R' is H, alkyl, or aryl. In some embodiments, R' is alkyl. In some embodiments, R' is aryl. In some embodiments, R' is heteroaryl. For clarity, it is understood that the connectivity of the -L-moiety should be read from right to left. That is, the first listed atom in the exemplary L groups described herein is covalently bonded to the glucan moiety.

In other embodiments, any of formulas (I), (Ia), (Ib), (Ic), (Id), (Ie), (If), or (Ig), is conjugated to a targeting moiety. See, e.g., PCT/US07/23307 (e.g., paragraphs [00111]-[00150]), which is herein incorporated by reference. In some embodiments, group A comprises the targeting moiety. In further embodiments, group A is OR, SR, or NR'R, where R comprises a targeting moiety and R' is H, alkyl, or aryl. In other embodiments, group A is OR, SR, or NR'R, where R is -L-T; L is a covalent bond or a linker molecule; T is a targeting moiety; and R' is H, alkyl, or aryl.

In some embodiments, the term "conjugate" and grammatical forms thereof refers to any association between the indicated molecules. In some embodiments, the conjugation is covalent. In other embodiments, the conjugation is non-covalent. In some embodiments, the conjugation is direct. In other embodiments, the conjugation is via a linker molecule. In some embodiments the conjugation will be via any means known in the art and as described herein. For example, the conjugation may be via amide formation, urethane, imine or disulfide linkage between the respective molecules, or between a linker moiety with the respective molecules. It is to be understood that there is no limitation with respect to the chemical backbone of the linker molecules. In some embodiments, the chemical backbone may be biocompatible, non-immunogenic and/or water soluble. In some embodiments, the linker may comprise poly ethylene glycol (PEG), further comprising active chemical groups which facilitate linkage as herein described. In some embodiments, the linker molecule comprises alkanes, polyesters, polyimines, poly-acids, proteins, peptides, DNA, RNA, other glucans, lipids, saccharides, polysaccharides, carbon nanotubes, dendrimers, or solid particles, such as, for example, polymers, metals, salts, inorganic materials, etc. In other embodiments, the linker molecule comprises an alkylene, alkenylene, alkynylene, heteroalkylene, heteroalkenylene, or heteroalkynylene moiety.

In some embodiments, the targeting moiety is for a particular phagocytic cell type, or in some embodiments, for a particular phagocytic cell, for example, an infected cell, or in some embodiments, a neoplastic cell or in some embodiments, a preneoplastic cell. In some embodiments, for example, targeting of a virally infected cell may be accomplished via linkage of the glucan with a viral co-receptor. In some embodiments, targeting moieties may include integrins or class II molecules of the MHC, which may be up-regulated on infected cells such as professional antigen-presenting cells.

In some embodiments, reference herein to a targeting moiety is to be understood to encompass an antibody, or fragment thereof as described herein, a naturally occurring peptide ligand for the referenced receptor, or a modified form thereof, such as, for example, a truncation product. In some embodiments, reference herein to a targeting moiety is to be understood to encompass artificial peptides, small molecules, and the like.

In certain embodiments, the targeting moiety is a peptide, an antibody, an antibody fragment, a receptor, Protein A, Protein G, Protein L, biotin, avidin, streptavidin, a metal ion chelate, an enzyme cofactor, a nucleic acid or a ligand. In some embodiments, such a targeting moiety may comprise an antibody or antibody fragment. In some embodiments, such an antibody or antibody fragment will specifically interact with a desired target; for example, by interacting with a phagocyte, such that linkage of said antibody or fragment with the glucan does not inhibit such interaction. In other embodiments, the targeting moiety may be an aptamer, a naturally occurring or artificial ligand, or an engineered binding protein.

In other embodiments, the invention relates to a compound described by any of formulas described herein. In some embodiments, the invention relates to a compound described by any of formulas (I), (Ia), (Ib), (Ic), (Id), (Ie), (If), and (Ig) as described herein. In certain embodiments, the invention relates to any of the compounds and formulas described in the schemes (e.g., Schemes I-XII) described herein. In other embodiments, the invention relates to a compound described by any of formulas 1-109 described herein. In certain embodiments of any of formulas 1-109, when n is present in the formula, n may be 1, 2, 3, 4, 5, 6, 7, 8, 9, 10, 11, 12, 13, 14, 15, 16, 17, or 18. In certain embodiments, the compound of any of formulas 1-109 is as described in the Examples provided herein.

In some embodiments, "alkyl," as featured in any of the compounds described herein (e.g., the compound of any of formulas (I), (Ia), (Ib), (Ic), (Id), (Ie), (If), and (Ig), the compound as described in any of Schemes I-XII, or the compound any of formulas 1-109), refers to a saturated, optionally substituted straight or branched chain hydrocarbon group as, e.g., described herein in the Definitions. In other embodiments, "alkyl" as featured in any of the compounds described herein (e.g., the compound of any of formulas (I), (Ia), (Ib), (Ic), (Id), (Ie), (If), and (Ig), the compound as described in any of Schemes I-XII, or the compound any of formulas 1-109), refers to a cycloaliphatic group as, e.g., described herein in the Definitions.

DEFINITIONS

Compounds of this invention include those described generally for formula I, above, and are further illustrated by the classes, subclasses, and species disclosed herein. It will be appreciated that preferred subsets described for each variable herein can be used for any of the structural subsets as well. As used herein, the following definitions shall apply unless otherwise indicated.

As described herein, compounds of the invention may be optionally substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, means that a hydrogen radical of the designated moiety is replaced with the radical of a specified substituent, provided that the substitution results in a stable or chemically feasible compound. The term "substitutable", when used in reference to a designated atom, means that attached to the atom is a hydrogen radical, which hydrogen atom can be replaced with the radical of a suitable substituent. Unless otherwise indicated, an "optionally substituted" group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds.

A stable compound or chemically feasible compound is one in which the chemical structure is not substantially altered when kept at a temperature from about −80° C. to about +40°, in the absence of moisture or other chemically reactive conditions, for at least a week, or a compound which maintains its integrity long enough to be useful for therapeutic or prophylactic administration to a patient.

The phrase "one or more substituents", as used herein, refers to a number of substituents that equals from one to the maximum number of substituents possible based on the number of available bonding sites, provided that the above conditions of stability and chemical feasibility are met.

As used herein, the term "independently selected" means that the same or different values may be selected for multiple instances of a given variable in a single compound.

As used herein, the term "aromatic" includes aryl and heteroaryl groups as described generally below and herein.

The term "aliphatic" or "aliphatic group", as used herein, means an optionally substituted straight-chain or branched $C_{1-12}$ hydrocarbon which is completely saturated or which contains one or more units of unsaturation. For example, suitable aliphatic groups include optionally substituted linear or branched alkyl, alkenyl, and alkynyl groups. Unless otherwise specified, in various embodiments, aliphatic groups have 1-12, 1-10, 1-8, 1-6, 1-4, 1-3, or 1-2 carbon atoms.

The term "alkyl", used alone or as part of a larger moiety, refers to a saturated, optionally substituted straight or branched chain hydrocarbon group having 1-12, 1-10, 1-8, 1-6, 1-4, 1-3, or 1-2 carbon atoms, e.g., methyl, ethyl, n-propyl. i-propyl, n-butyl, i-butyl, s-butyl, t-butyl, n-pentyl, 1-methylbutyl, 2-methylbutyl, 3-methylbutyl, neopentyl, 3,3-dimethylpropyl, hexyl, 2-methylpentyl, heptyl, and the like and of cycloaliphatic groups (e.g., cycloalkyl and cycloalkenyl groups) as described herein.

The term "alkenyl", used alone or as part of a larger moiety, refers to an optionally substituted straight or branched chain hydrocarbon group having at least one double bond and having 2-12, 2-10, 2-8, 2-6, 2-4, or 2-3 carbon atoms. Exemplary alkenyl groups include vinyl, prop-1-enyl, prop-2-enyl, allenyl, 2-methylprop-2-enyl, 3-methylbut-2-enyl, butadienyl, and the like.

The term "alkynyl", used alone or as part of a larger moiety, refers to an optionally substituted straight or branched chain hydrocarbon group having at least one triple bond and having 2-12, 2-10, 2-8, 2-6, 2-4, or 2-3 carbon atoms. Exemplary alkynyl groups include $CH_3$—C≡C—, H—C≡C—$CH_2$—, $CH_3$—C≡C—$CH_2$—, H—C≡C—$CH_2CH_2$—, H—C≡C—$CH(CH_3)CH_2$—, H—C≡C—$CH_2$—C≡C—$CH_2$—, The term "alkylene" refers to a bivalent alkyl group. An "alkylene chain" is a polymethylene group, e.g., —$(CH_2)_n$—, wherein n is a positive integer, e.g., from 1 to 6, from 1 to 4, from 1 to 3, from 1 to 2, or from 2 to 3. An optionally substituted alkylene chain is a polymethylene group in which one or more methylene hydrogen atoms is optionally replaced with a substituent. Suitable substituents include those described below for a substituted aliphatic group and also include those described in the specification herein. It will be appreciated that two substituents of the alkylene group may be taken together to form a ring system. In certain embodiments, two substituents can be taken together to form a 3-7-membered ring. The substituents can be on the same or different atoms.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "alkynylene" refers to a bivalent alkynyl group. A substituted alkynylene chain is a polymethylene group containing at least one triple bond in which one or more hydrogen atoms are replaced with a substituent. Suitable substituents include those described below for a substituted aliphatic group.

The terms "aryl" and "ar-", used alone or as part of a larger moiety, e.g., "aralkyl", "aralkoxy", or "aryloxyalkyl", refer to an optionally substituted $C_{6-14}$ aromatic hydrocarbon moiety comprising one to three aromatic rings. For example, the aryl group is a $C_{6-10}$ aryl group (i.e., phenyl and naphthyl). Aryl groups include, without limitation, optionally substituted phenyl, naphthyl, anthracenyl, and phenanthrenyl. The terms "aryl" and "ar-", as used herein, also include groups in which an aryl ring is fused to one or more cycloaliphatic rings to form an optionally substituted cyclic structure (e.g., 2,3-dihydroindenyl; 1,2,3,4-tetrahydroaphetalenyl; 1,2-dihydronaphthalenyl; 2,3-dihydronaphthalenyl; 8,10-dihydroanthracenyl, fluorenyl, and the like.

The terms "cycloaliphatic", "carbocycle", "carbocyclyl", "carbocyclo", or "carbocyclic", used alone or as part of a larger moiety, refer to an optionally substituted saturated or partially unsaturated cyclic aliphatic ring system having from 3 to about 14 ring carbon atoms. In some embodiments, the cycloaliphatic group is an optionally substituted monocyclic hydrocarbon having 3-8 or 3-6 ring carbon atoms. In particular embodiments, the cycloaliphatic group (e.g., a monocyclic cycloaliphatic group) has 3-8 ring carbon atoms. Cycloaliphatic groups include, without limitation, optionally substituted cyclopropyl, cyclobutyl, cyclopentyl, cyclopentenyl, cyclohexyl, cyclohexenyl, cycloheptyl, cycloheptenyl, cyclooctyl, cyclooctenyl, or cyclooctadienyl. The terms "cycloaliphatic", "carbocycle", "carbocyclyl", "carbocyclo", or "carbocyclic" also include optionally substituted polycyclic rings (e.g., optionally substituted bridged rings) or fused bicyclic rings having 6-12, 6-10, or 6-8 ring carbon atoms, wherein any individual ring in the bicyclic system has 3-8 ring carbon atoms.

The term "heteroaliphatic," as used herein, includes both saturated and unsaturated, nonaromatic, straight chain (i.e., unbranched), branched, acyclic, cyclic (i.e., heterocyclic), or polycyclic hydrocarbons, which are optionally substituted with one or more functional groups, and that contain one or more oxygen, sulfur, nitrogen, phosphorus, or silicon atoms, e.g., in place of carbon atoms. As will be appreciated by one of ordinary skill in the art, "heteroaliphatic" is intended herein to include, but is not limited to, heteroalkyl, heteroalkenyl, heteroalkynyl, and heterocyclyl moieties. Thus, as used herein, the term "heteroalkyl" includes straight, branched and cyclic alkyl groups, as defined herein, which are optionally substituted with one or more functional groups, and that contain one or more oxygen, sulfur, nitrogen, phosphorus, or silicon atoms, e.g., in place of carbon atoms. An analogous convention applies to other generic terms such as "heteroalkenyl", "heteroalkynyl", and the like. Furthermore, as used herein, the terms "heteroalkyl", "heteroalkenyl", "heteroalkynyl", and the like encompass both substituted and unsubstituted groups. In certain embodiments, as used herein, "heteroaliphatic" is used to indicate those heteroaliphatic groups (cyclic, acyclic, substituted, unsubstituted, branched or unbranched) having 1-20 carbon atoms, 1-12 carbon atoms, 1-6 carbon atoms, or 2-6 carbon atoms. In certain embodiments, a heteroaliphatic group has 2-12, 2-10, 2-8, 2-6, or 2-4 carbon atoms. In certain embodiments, a heteroaliphatic group has 1-4 or 2-4 carbon atoms. In certain embodiments, a heteroaliphatic group has 1-3 or 2-3 carbon atoms. In certain embodiments, a heteroaliphatic group has 1-2 carbon atoms. In certain embodiments, an heteroaliphatic group has 1 carbon atom. In certain embodiments, a heteroaliphatic group has 2 carbon atoms. Heteroaliphatic group substituents include, but are not limited to, any of the substituents described herein, that result in the formation of a stable moiety (for example, a heteroaliphatic group substituted with one or more aliphatic, alkyl, alkenyl, alkynyl, heteroaliphatic, heterocyclic, aryl, heteroaryl, acyl, sulfinyl, sulfonyl, oxo, imino, thiooxo, phosphino, cyano, amino, azido, nitro, hydroxy, thio, and/or halo groups).

As used herein, the terms "heterocycle", "heterocyclyl", "heterocyclic radical", and "heterocyclic ring" are used interchangeably and refer to a stable 3- to 8-membered monocyclic or 7-10-membered bicyclic heterocyclic moiety that is either saturated or partially unsaturated, and having, in addition to carbon atoms, one or more, such as one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or NR$^+$ (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, piperidinyl, decahydroquinolinyl, oxazolidinyl, piperazinyl, dioxanyl, dioxolanyl, diazepinyl, oxazepinyl, thiazepinyl, morpholinyl, and thiamorpholinyl. A heterocyclyl group may be mono-, bi-, tri-, or polycyclic, preferably mono-, bi-, or tricyclic, more preferably mono- or bicyclic. The term "heterocyclylalkyl" refers to an alkyl group substituted by a heterocyclyl, wherein the alkyl and heterocyclyl portions independently are optionally substituted. Additionally, a heterocyclic ring also includes groups in which the heterocyclic ring is fused to one or more aryl rings.

The terms "heteroaryl" and "heteroar-", used alone or as part of a larger moiety, e.g., "heteroaralkyl", or "heteroaralkoxy", refer to groups having 5 to 14 ring atoms, preferably 5, 6, 9, or 10 ring atoms; having 6, 10, or 14π electrons shared in a cyclic array; and having, in addition to carbon atoms, from one to five heteroatoms. A heteroaryl group may be mono-, bi-, tri-, or polycyclic, for example, mono-, bi-, or tricyclic, (e.g., mono- or bicyclic). The term "heteroatom" refers to nitrogen, oxygen, or sulfur, and includes any oxidized form of nitrogen or sulfur, and any quaternized form of a basic nitrogen. For example, a nitrogen atom of a heteroaryl may be a basic nitrogen atom and may also be optionally oxidized to the corresponding N-oxide. When a heteroaryl is substituted by a hydroxy group, it also includes its corresponding tautomer. The terms "heteroaryl" and "heteroar-", as used herein, also include groups in which a heteroaromatic ring is fused to one or more aryl, cycloaliphatic, or heterocycloaliphatic rings. Nonlimiting examples of heteroaryl groups include thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, pteridinyl, indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

An aryl (including aralkyl, aralkoxy, aryloxyalkyl and the like) or heteroaryl (including heteroalkyl and heteroarylalkoxy and the like) group may contain one or more substituents and thus may be "optionally substituted". In addition to the substituents defined above and herein, suitable substituents on the unsaturated carbon atom of an aryl or heteroaryl group also include and are generally selected from -halo, —NO$_2$, —CN, —R$^+$, —C(R$^+$)=C(R$^+$)$_2$, —C≡C—R$^+$, —OR$^+$, —SR$^o$, —S(O)R$^o$, —SO$_2$R$^o$, —SO$_3$R$^+$, —SO$_2$N(R$^+$)$_2$, —N(R$^+$)$_2$, —NR$^+$C(O)R$^+$, —NR$^+$C(S)R$^+$, —NR$^+$C(O)N(R$^+$)$_2$, —NR$^+$C(S)N(R$^+$)$_2$, —N(R$^+$)C(=NR$^+$)—N(R$^+$)$_2$, —N(R$^+$)C(=NR$^+$)—R$^o$, —NR$^+$CO$_2$R$^+$, —NR$^+$SO$_2$R$^o$, —NR$^+$SO$_2$N(R$^+$)$_2$, —O—C(O)R$^+$, —O—CO$_2$R$^+$, —OC(O)N(R$^+$)$_2$, —C(O)R$^+$, —C(S)R$^o$, —CO$_2$R$^+$, —C(O)—C(O)R$^+$, —C(O)N(R$^+$)$_2$, —C(S)N(R$^+$)$_2$, —C(O)N(R$^+$)—OR$^+$, —C(O)N(R$^+$)C(=NR$^+$)—N(R$^+$)$_2$, —N(R$^+$)C(=NR$^+$)—N(R$^+$)—C(O)R$^+$, —C(=NR$^+$)—N(R$^+$)$_2$, —C(=NR$^+$)—OR$^+$, —N(R$^+$)—N(R$^+$)$_2$, —C(=NR$^+$)—N(R$^+$)—OR$^+$, —C(R$^o$=N—OR$^+$, —P(O)(R$^+$)$_2$, —P(O)(OR$^+$)$_2$, —O—P(O)—OR$^+$, and —P(O)(NR$^+$)—N(R$^+$)$_2$, wherein R$^+$, independently, is hydrogen or an optionally substituted aliphatic, aryl, heteroaryl, cycloaliphatic, or heterocyclyl group, or two independent occurrences of R$^+$ are taken together with their intervening atom(s) to form an optionally substituted 5-7- membered aryl, heteroaryl, cycloaliphatic, or heterocyclyl ring. Each R$^o$ is an optionally substituted aliphatic, aryl, heteroaryl, cycloaliphatic, or heterocyclyl group.

An aliphatic or heteroaliphatic group, or a non-aromatic carbocyclic or heterocyclic ring may contain one or more substituents and thus may be "optionally substituted". Unless otherwise defined above and herein, suitable substituents on the saturated carbon of an aliphatic or heteroaliphatic group, or of a non-aromatic carbocyclic or heterocyclic ring are selected from those listed above for the unsaturated carbon of an aryl or heteroaryl group and additionally include the following: =O, =S, =C(R*)$_2$, =N—N(R*)$_2$, =N—OR*, =N—NHC(O)R*, =N—NHCO$_2$R$^o$=N—NHSO$_2$R$^o$ or =N—R* where R$^o$ is defined above, and each R* is independently selected from hydrogen or an optionally substituted C$_{1-6}$ aliphatic group. In certain embodiments, an aliphatic group (e.g., an alkyl group as described herein) comprises one or more substitutents independently selected from alkoxy, aryloxy, sulfhydryl, alkylthio, arylthio, halogen, alkylsilyl, hydroxyl, fluoroalkyl, perfluoroalkyl, amino, aminoalkyl disubstituted amino, quaternary amino, hydroxylalkyl, carboxylalkyl, and carboxyl groups.

In addition to the substituents defined above and herein, optional substituents on the nitrogen of a non-aromatic heterocyclic ring also include and are generally selected from R$^+$, —N(R$^+$)$_2$, —C(O)R$^+$, —C(O)OR$^+$, —C(O)C(O)R$^+$, —C(O)CH$_2$C(O)R$^+$, —S(O)$_2$R$^+$, —S(O)$_2$N(R$^+$)$_2$, —C(S)N(R$^+$)$_2$, —C(=NH)—N(R$^+$)$_2$, or —N(R$^+$)S(O)$_2$R$^+$; wherein each R$^+$ is defined above. A ring nitrogen atom of a heteroaryl or non-aromatic heterocyclic ring also may be oxidized to form the corresponding N-hydroxy or N-oxide compound. A nonlimiting example of such a heteroaryl having an oxidized ring nitrogen atom is N-oxidopyridyl.

As detailed above, in some embodiments, two independent occurrences of R$^+$ (or any other variable similarly defined in the specification and claims herein), are taken together with their intervening atom(s) to form a monocyclic or bicyclic ring selected from 3-13-membered cycloaliphatic, 3-12-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur.

Exemplary rings that are formed when two independent occurrences of R$^+$ (or any other variable similarly defined in the specification and claims herein), are taken together with their intervening atom(s) include, but are not limited to the following: a) two independent occurrences of R$^+$ (or any other variable similarly defined in the specification or claims herein) that are bound to the same atom and are taken together with that atom to form a ring, for example, N(R$^+$)$_2$, where both occurrences of R$^+$ are taken together with the nitrogen atom to form a piperidin-1-yl, piperazin-1-yl, or morpholin-4-yl group; and b) two independent occurrences of R$^+$ (or any other variable similarly defined in the specification or claims herein) that are bound to different atoms and are taken together with both of those atoms to form a ring, for example where a phenyl group is substituted with two occurrences of OR$^+$

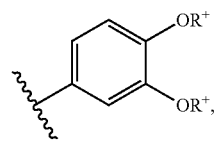

these two occurrences of R$^+$ are taken together with the oxygen atoms to which they are bound to form a fused 6-membered oxygen containing ring:

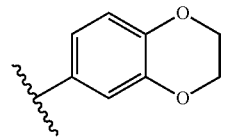

It will be appreciated that a variety of other rings (e.g., spiro and bridged rings) can be formed when two independent occurrences of R$^+$ (or any other variable similarly defined in the specification and claims herein) are taken together with their intervening atom(s) and that the examples detailed above are not intended to be limiting.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures where there is a replacement of hydrogen by deuterium or tritium, or a replacement of a carbon by a $^{13}$C- or $^{14}$C-enriched carbon are within the scope of this invention. Such compounds are useful, as a nonlimiting example, as analytical tools or probes in biological assays.

As used herein, the term "amino acid," in its broadest sense, refers to any compound and/or substance that can be incorporated into a polypeptide chain, e.g., through formation of one or more peptide bonds. In some embodiments, an amino acid has the general structure H$_2$N—C(H)(R)—COOH. In some embodiments, an amino acid is a naturally-occurring amino acid. In some embodiments, an amino acid is a synthetic amino acid; in some embodiments, an amino acid is a D-amino acid; in some embodiments, an amino acid is an L-amino acid. "Standard amino acid" refers to any of the twenty standard L-amino acids commonly found in naturally occurring peptides. "Nonstandard amino acid" refers to any amino acid, other than the standard amino acids, regardless of whether it is prepared synthetically or obtained from a natural source. In some embodiments, an amino acid, including a carboxy- and/or amino-terminal amino acid in a polypeptide, can contain a structural modification as compared with the general structure above. For example, in some embodiments, an amino acid may be modified by methylation, amidation, acetylation, and/or substitution as compared with the general structure. In some embodiments, such modification may, for example, alter the circulating half-life of a polypeptide containing the modified amino acid as compared with one containing an otherwise identical unmodified amino acid. In some embodiments, such modification does not significantly alter a relevant activity of a polypeptide containing the modified amino acid, as compared with one containing an otherwise identical unmodified amino acid. As will be clear from context, in some embodiments, the term "amino acid" is used to refer to a free amino acid; in some embodiments it is used to refer to an amino acid residue of a polypeptide.

DETAILED DESCRIPTION OF THE PRESENT INVENTION

Also described herein are new methods that now allow the preparation the β-1,6-D-glucan oligomers of the formulas described herein. Reagents and starting materials are generally available from commercial sources such as Aldrich Chemicals (Milwaukee, Wis.) or are readily prepared using methods well known to those skilled in the art (see, e.g., Louis F. Fieser and Mary Fieser, Reagents for Organic Synthesis, v. 1-19, Wiley, New York (1967-1999 ed.), Beilsteins Handbuch der organischen Chemie, 4, Aufl. Ed. Springer-Verlag, Berlin, including supplements (also available via the Beilstein online database) or Carbohydrate Chemistry: Proven Synthetic Methods, Pavol Kovac, Ed., CRC Press, Boca Raton).

Various methods for the preparation, isolation, and characterization of lower β-1,6-D-glucan oligomers (e.g., 4-mer through to 9-mer) have been described. Exemplary methods include those described in Linberg, B. et al. *Acta Chem. Scand.* 8, 985-988, 1954 (relating to chemical transformations of pustulan, a 20 kDa β-1,6-linked D-glucose polysaccharide obtained from several species of lichen); Zhu, Y.; et al. *Carbohydrate Res.*, 332, 1-21, 2001 (chemical synthesis); Fujimori, Y. et al. *Carbohydrate Res.* 344, 972-978, 2009 (enzymatic synthesis); and Bi, H. et al. *Carbohydrate Res.* 344, 1254-1258 2009 (natural product extraction). α-1,6-D-Glucan structures are also described in Honda, S. et al. *Methods,* 1992, 4, 233-243. Exemplary oligomeric β-1,6-D-glucans are described in Agri. *Biol. Chem.* 43, 2029-2034, 1979; *Carbohydrate Res.* 332, 1-21, 2001; and *Carbohydrate Res.* 344, 972-978, 2009. Glucans are also described in Carbohydrate Research, 2013, 366:6-16. New methods for the preparation of such oligomers would be useful for the preparation of the oligomers described herein.

In the present invention we have devised a new, general process for the acid-catalyzed hydrolysis of pustulan that now allows for the efficient production and isolation of higher oligomers (e.g., greater than nona-saccharides). The β-1,6-D-glucan oligomers from the 10-mer through the 20-mer described herein are novel compositions of matter. Such oligomers have been isolated as discrete substances, characterized by mass spectrometry, and the stereochemical assignment of repeating β-1,6-D-glucose stereochemistry has been made based on their derivation from the parent β-1,6-D-glucan polymer pustulan.

In the general case, oligosaccharide synthetic methodology has as its key step the selective activation of a glycosidic center (C-1) in a suitably protected donor reactant followed by the formation of a bond to the oxygen of a free hydroxyl group at C-6 of a suitably protected acceptor reactant, giving rise to a product that has both reactants linked 1,6 through a newly formed glycosidic bond. When an acyloxy substituent such as acetate or benzoate is present at C-2 of the donor, there is often a high degree of selectivity for β-stereochemistry of the resulting glycosidic bond. The tendency for β-stereoselectivity of the newly formed glycosidic bond is thought to arise from neighboring group participation by the acyloxy group located at the 2-position of the donor, such that the acyl carbonyl stabilizes the build-up of positive charge at C-1, thus blocking the approach of a nucleophile from the α-face and directing it to the β-face of the donor reactant [Lindhorst, T. K. Essentials in Carbohydrate Chemistry and Biochemistry, Wiley-VCH: Weinheim, 2003].

General chemical synthesis strategies for preparing useful synthetic precursors for the higher β-1,6-linked D-glucose polysaccharides described herein divide along two lines: solid phase synthesis and solution phase synthesis. Solid phase methods providing high stereoselectivity for formation of each β-1,6 glycosidic linkage are described for the preparation of simple β-1,6-linked D-glucose polysaccharides of up to five glucose units comprised of branched β-1,6/1,3)-linked D-glucose oligomers. These methods employ a variety of activating functionalities in the donor reactant, including phosphates, epoxides and phenylsulfoxides [Zheng, C. et al. J. Org. Chem. 63, 1126-1130, 1998; Andrade, R. B. et al. Org. Lett. 1, 1811, 1999; Plante, O. J. et al. Science, 291, 1523, 2001; Nicolaou, K. C. et al. J. Amer. Chem. Soc. 119, 449-450, 1999].

Several solution phase syntheses described in the literature provide specific examples of preparing β-1,6-linked D-glucose polysaccharides in the range of dimers to octamers. Examples include the polymerization of 2,3,4,5-tetra-O-acetyl-D-glucose in the presence of zinc chloride followed by removal of the acetyl groups to give a mixture of β-1,6-linked glucose di-, tri-, tetra-, hexa-, and heptasaccharides [Parish, C. R. et al. PCT, WO199633726] and stepwise synthesis using trichloracetimidate intermediates to prepare di-, tri-, tetra-, hexa- and octa-β-1,6-linked D-glucose polysaccharides [Zhu, Y. et al. Carbohydrate Res. 332, 1-21, 2001]. One example that illustrates the complexity of stepwise synthesis and the critical attention that must be paid to careful strategic choice of orthogonal reactivity to achieve selectivity when forming each β-1,6-linked glucose is seen in the five-step synthesis of a per-benzoylated O-pentenyl β-1,6-linked glucose hexa-saccharide [Kaeothip, S. et al. J. Org. Chem. 76, 7388-7398, 2011]. Other oligosaccharides are described in WO 1996/33726.

For illustrative purposes, the reaction schemes depicted below provide potential routes for synthesizing the compounds of the present invention, as well as key intermediates. For a more detailed description of the individual reaction steps in certain embodiments, see the Examples section below. Those skilled in the art will appreciate that other synthetic routes may be used to synthesize the inventive compounds. Although specific starting materials and reagents are depicted in the schemes and discussed below, it will be recognized that other starting materials and reagents can be easily substituted to provide a variety of derivatives and/or reaction conditions. In addition, many of the compounds prepared by the methods described below can be further modified in light of this disclosure using conventional chemistry well known to those skilled in the art.

In another aspect, the invention features methods for the preparation of β-1,6-D-glucan oligomers, e.g., as described herein in Schemes I-XI.

In other embodiments, the invention features compositions comprising synthetic intermediates or compounds described in Schemes I-XI as described herein.

In one embodiment, β-1,6-D-glucan oligomers of formula (Ia) can be generally prepared according to Scheme I, comprising Steps a, b, and c. In Step a, the β-1,6-D-glucan starting material A containing a C-1 hydroxyl is reacted with an acylating agent to produce a per-acetylated glycoside B. In Step b, intermediate B is reacted with a Lewis acid and an alkyl alcohol to give a β-O-alkyl glycoside C. In Step c, material C is hydrolyzed (e.g., using basic hydrolysis) to remove the acyl groups to give an oligomer D according to formula (Ia), wherein R is an unsubstituted or substituted alkyl.

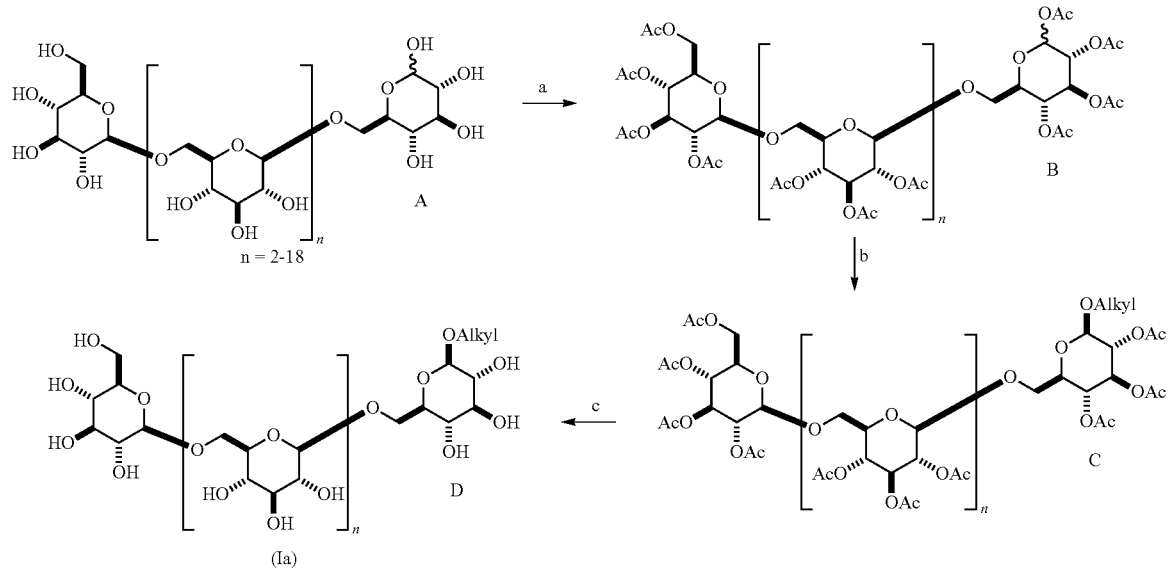

Scheme I

Reactions: a) (RCO)$_2$O or RCOCl/base; b) Lewis acid catalyst, AlkylOH; c) basic hydrolysis In another embodiment, the β-1,6-D-glucan oligomers of formula (Ia) can be prepared as shown in Scheme II.

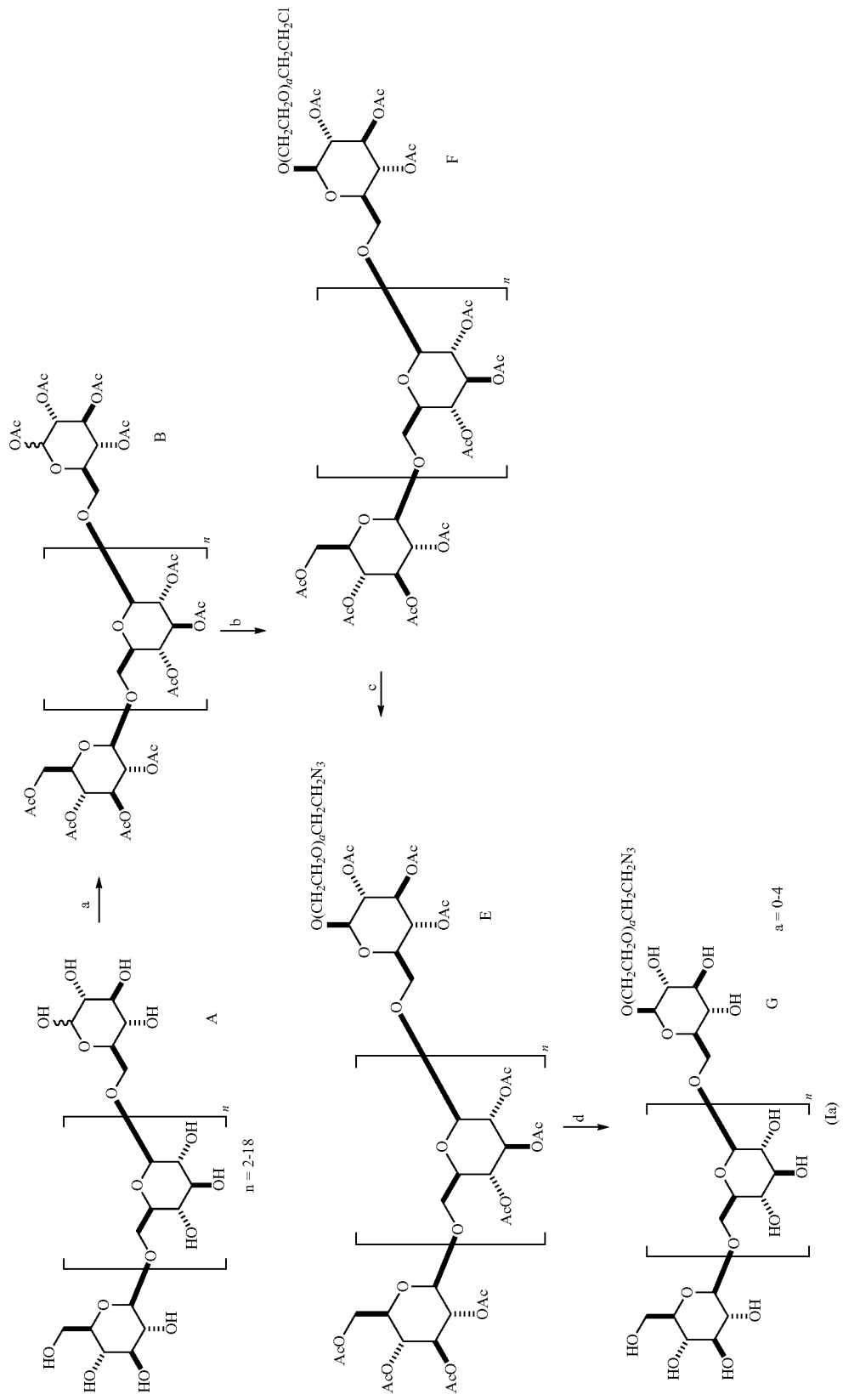

In Scheme II, the β-1,6-D-glucan starting material A containing a C-1 hydroxyl is reacted with acetic anhydride/sodium acetate to produce a per-acetylated glycoside B (Step a). In Step b, intermediate B is reacted with a Lewis acid such as FeCl$_3$ and a halo-substituted alkyl alcohol selected from the group HO(CH$_2$CH$_2$O)$_a$CH$_2$CH$_2$Cl to give a β-O-haloalkyl glycoside F, wherein a is 0, 1, 2, 3, or 4. This material F is reacted with sodium azide to give an azido-substituted O-alkyl glycoside E, which is reacted with NaOMe/MeOH to give the oligomer G of formula (Ia) wherein R is azido-substituted alkyl.

Unexpectedly, we have observed that the Lewis acid, the solvent and the reaction conditions used in step c in Scheme II play a critical role in obtaining a successful outcome. When using the Lewis acid SnCl$_4$/AgO$_2$CCF$_3$ in dichloromethane [see, e.g., Ceccione, S. et al. Carbohydrate Chemistry: Proven Synthetic Methods, pp. 175-180, Pavol Kovac, Ed., CRC Press, Boca Raton], we obtained fragmentation and formation of mixtures of alkyl glycosides of several lower order oligosaccharides. The development of synthetic conditions using FeCl$_3$ in toluene, and heating at 45° C. with careful monitoring gave the desired alkyl glycoside in high yield and with reduced fragmentation.

In another aspect, the invention features any of the oligomers described in any of the synthetic schemes described herein, as well as compositions comprising said oligomers. In one embodiment, the oligomer has a structure according to B,

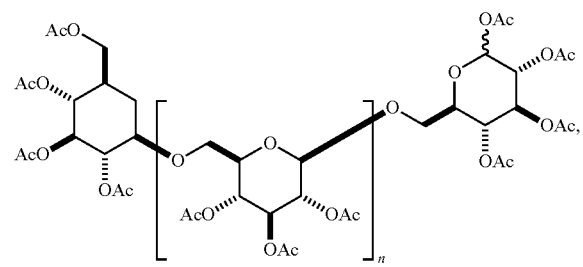

B wherein n is 6, 7, 8, 9, 10, 11, 12, 13, 14, 15, 16, 17, 18, 19, or 20. In some embodiments, n is 6, 7, 8, 9, 10, 11, 12, 13, 14, 15, 16, 17, or 18. In some embodiments, n is 8, 9, 10, 11, 12, 13, 14, 15, 16, 17, 18, 19, or 20. In other embodiments, n is 8, 9, 10, 11, 12, 13, 14, 15, 16, 17, or 18.

In another embodiment, the β-1,6-D-glucan oligomers of formula (Ia) can be prepared as shown in Scheme III.

Scheme III

R' = alkylCO- or ArylCO-
R" = alkylCO- or ArylCO-

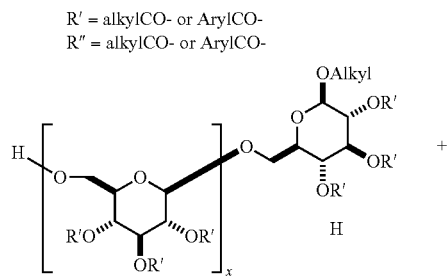

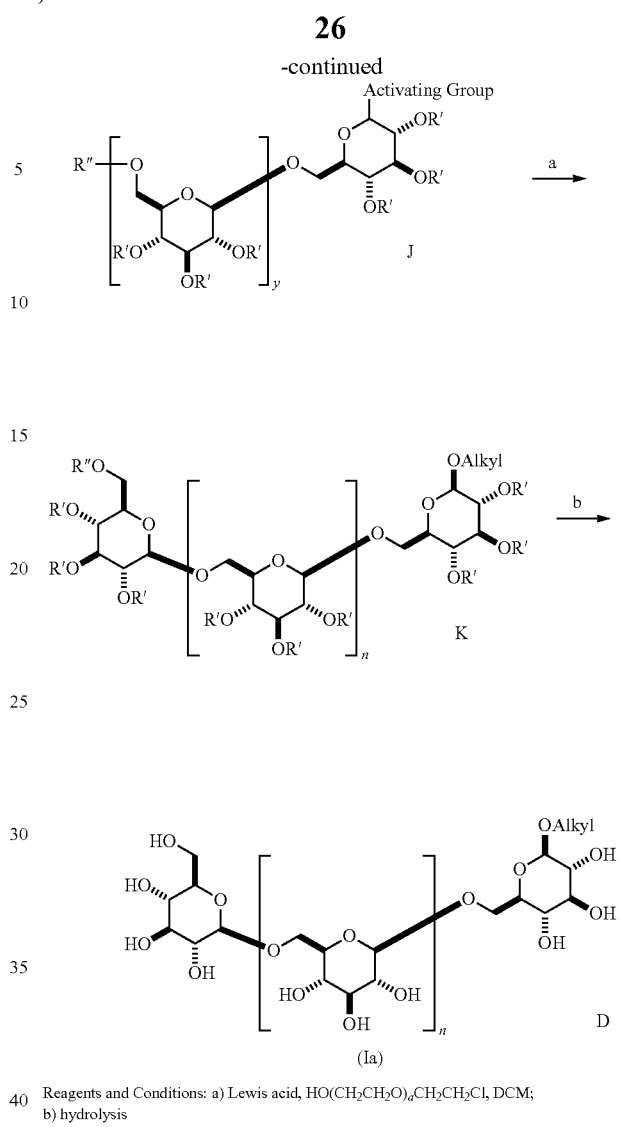

Reagents and Conditions: a) Lewis acid, HO(CH$_2$CH$_2$O)$_a$CH$_2$CH$_2$Cl, DCM; b) hydrolysis In Scheme III, the alkyl or aryl moiety of the carbonyl group is, independently, substituted or unsubstituted. This scheme uses as one reactant a suitably protected acceptor reactant H composed of n D-glucopyranoside units, wherein x is an integer from 0 to 6 (e.g., x is 0, 1, 2, 3, 4, 5 or 6), and containing a β-oriented O-alkyl (unsubstituted or substituted) group at C1 of its first unit and a free hydroxyl group at C6 of its terminal unit. In other embodiments, x is 1, 2, 3, 4, 5, or 6. The donor reactant J is a suitably protected molecule composed of y D-glucopyranoside units, wherein y is an integer from 0 to 6 (e.g., y is 0, 1, 2, 3, 4, 5, or 6), and containing an activating functionality such as trichloroacetimidate, arylsulfinyl, arylsulfide, acetyl, and thioimidate at C1. In other embodiments, y is 1, 2, 3, 4, 5, or 6. Condensation in Step a of this acceptor donor pair using appropriate Lewis acid catalysts results in an oligomeric β-1,6-D-glucan product K. Subsequent hydrolysis in Step b removes the protective groups giving the product D according to formula (Ia).

We have observed unexpected reactivity in step a of Scheme III when attempting the condensation of a 4-mer acceptor (alkyl=CH$_2$CH$_2$N$_3$; x=3; R=C$_6$H$_5$CO) with a 2-mer-donor,

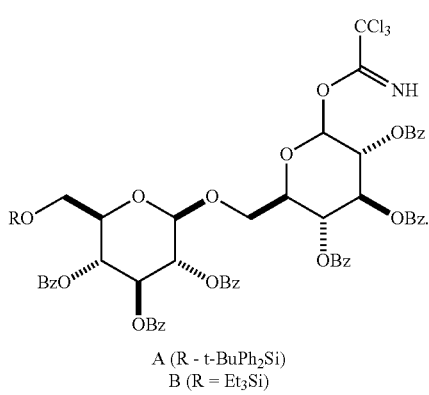

A (R - t-BuPh₂Si)
B (R = Et₃Si)

When the 2-mer donor was the tert-butyldiphenylsilyl-substituted A, only traces of the desired 6-mer product was observed; however when the donor was the triethylsilyl-substituted B, we obtained the desired 6-mer.

In another embodiment, the method Scheme IV can be used for the preparation of compounds of formula I.

Scheme IV

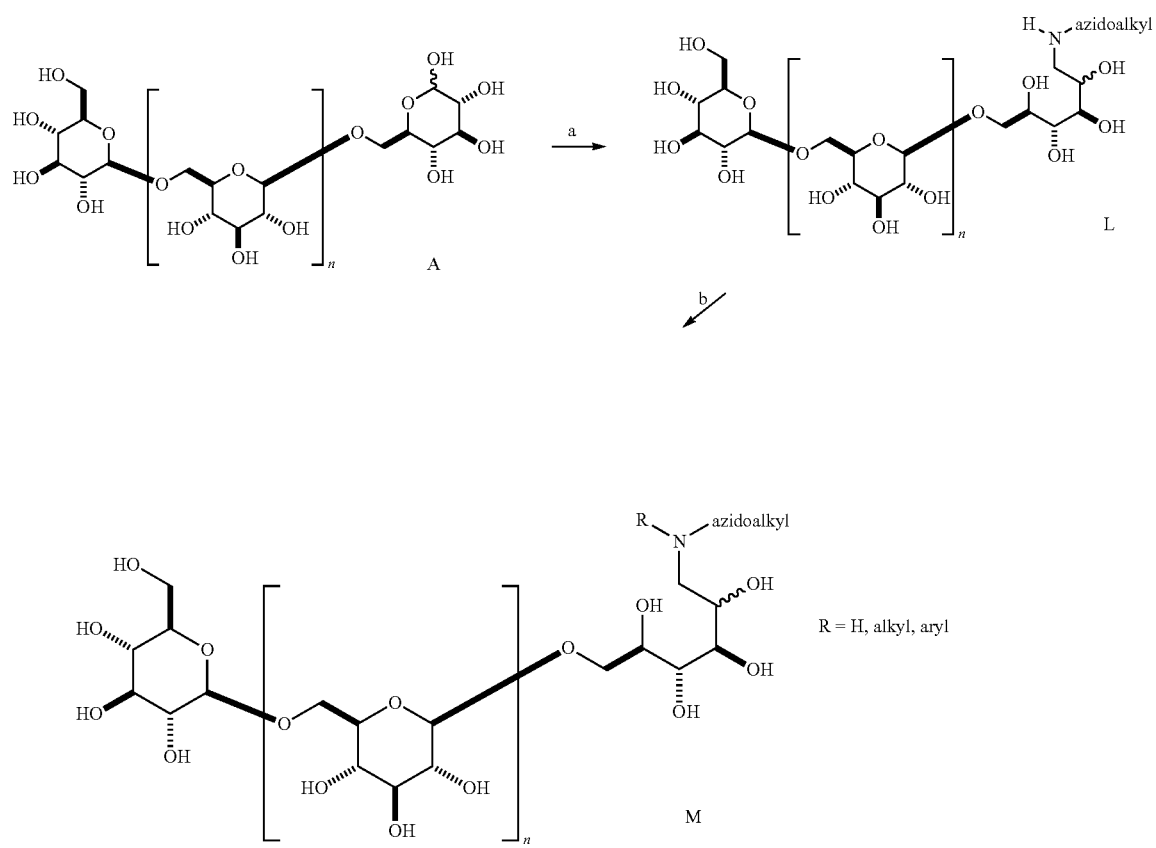

Reagents and Conditions: a) H₂Nalkylazide, NaBH₃CN, b) H₂CO, alkylCHO or arylCHO, NaBH₃CN, In Step A, the β-1,6-D-glucan starting material A containing a C-1 hydroxyl is reacted with an azido-substituted primary alkylamine under conditions of reductive amination. This reaction gives a β-1,6-D-glucan L that is reduced by one D-glucopyranose unit, wherein the terminal reducing D-glucopyranose unit has been transformed into a 1-amino-1-desoxy-D-glucitol. That intermediate is subjected to the reductive alkylation with formaldehyde, or an alkyl or aryl aldehyde to give a trisubstituted amine M according to formula I.

In one embodiment, β-1,6-D-glucan oligomers of formula I can be generally prepared according to Scheme V.

Scheme V

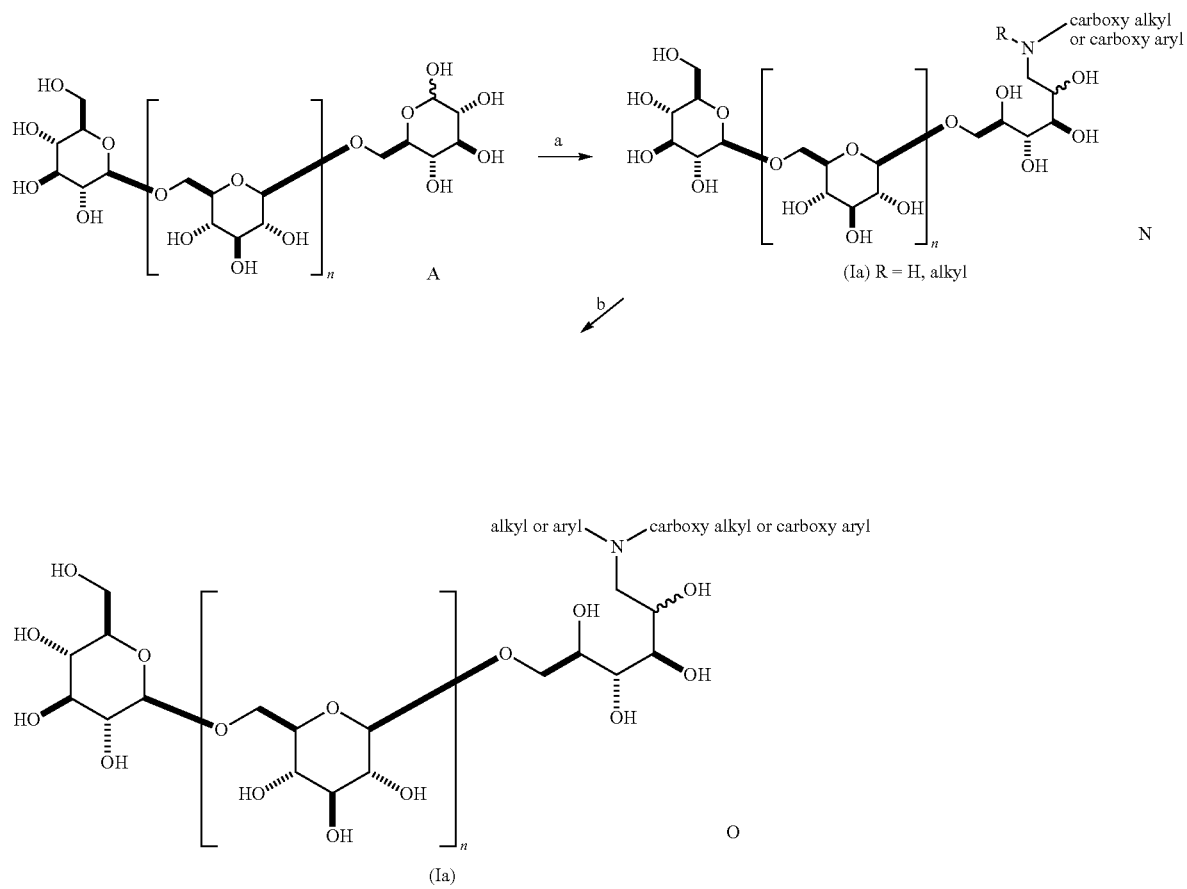

Reagents and Conditions: a) amino acid, NaBH₃CN, b) for R = H: H₂CO or alkylCHO or arylCHO, NaBH₃CN, A β-1,6-D-glucan starting material A containing a C-1 hydroxyl is reacted with an amino acid under conditions of reductive amination to afford a compound comprising, e.g., a carboxyl alkyl (e.g., where an aliphatic amino acid is used) or a carboxy aryl (e.g., where an aromatic amino acid is used). In correspondence with scheme IV this reaction gives a β-1,6-D-glucan N that is reduced by one D-glucopyranose unit, wherein the terminal reducing D-glucopyranose unit has been transformed into a 1-amino-1-desoxy-D-glucitol.

In cases where the product is a secondary amine, that intermediate may be further transformed by reductive alkylation with an alkyl or aryl aldehyde to give a trisubstituted amine O. The resulting product has the composition (Ia) wherein R is (2R,3R,4R,5RS)-2,3,4,5-tetrahydroxy-6-(N-alkyl-N-(carboxy-substituted alkyl))hexyl.

In one embodiment, β-1,6-D-glucan oligomers of formula I can be generally prepared according to Scheme VI.

Scheme VI

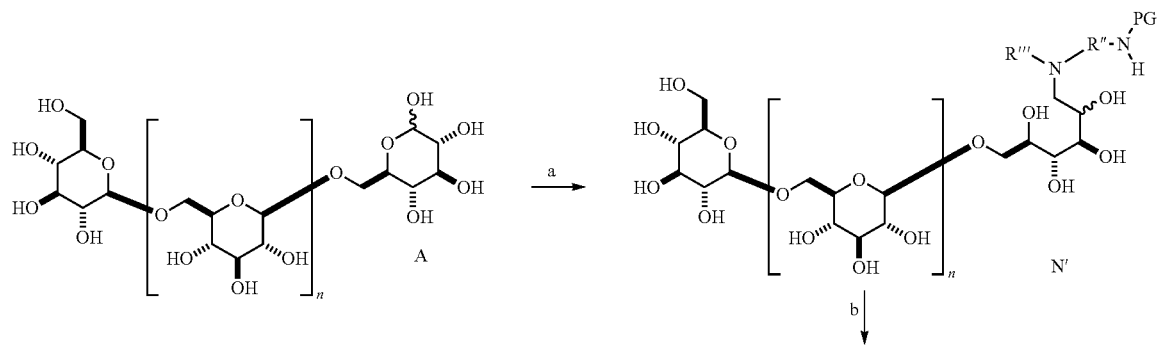

-continued

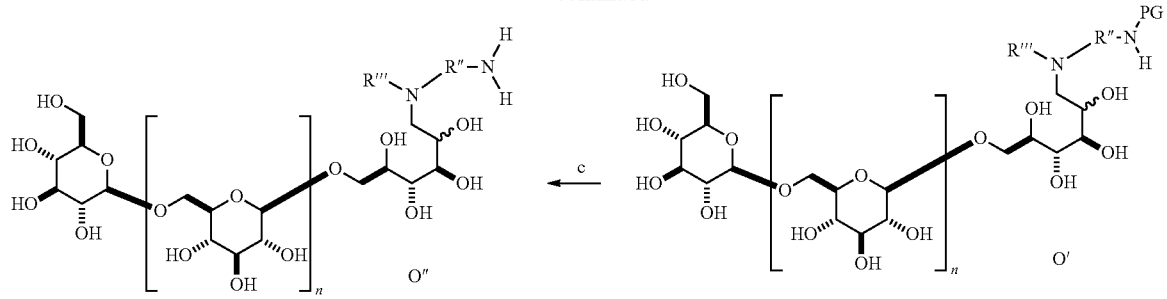

Reagents and Conditions:
a) reductive amination:
a mono-protected bisamine NHR'''-R''-NHPG where R'' is an alkylene, arylene, or heteroarylene; PG is a nitrogen protecting group; and R''' is H or alkyl; and NaBH$_3$CN
b) reductive amination when R''' = H:
H$_2$CO, (alkyl)CHO, (aryl)CHO, or (heteroary)CHO; and NaBH$_3$CN
c) deprotection (e.g., acidic conditions or H$_2$/Pd)

A β-1,6-D-glucan starting material A containing a C-1 hydroxyl is reacted with a suitably mono protected bis-alkyl under conditions of reductive amination to afford a compound comprising, e.g., an amino alkyl (e.g., where an aliphatic bis amine is used). In correspondence with scheme IV this reaction gives a β-1,6-D-glucan N' that is reduced by one D-glucopyranose unit, wherein the terminal reducing D-glucopyranose unit has been transformed into a 1-amino-1-desoxy-D-glucitol. In cases where the product is a secondary amine, that intermediate may be further transformed by reductive alkylation with an alkyl or aryl aldehyde to give a trisubstituted amine O'. The resulting product has the composition (Ia) wherein R is (2R,3R,4R,5RS)-2,3,4,5-tetrahydroxy-6-(N-alkyl-N-(protected amino-substituted alkyl))hexyl. Subsequent removal of the protecting group provides the product O'' wherein R is (2R,3R,4R,5RS)-2,3,4, 5-tetrahydroxy-6-(N-alkyl-N-(amino-substituted alkyl))hexyl.

In another embodiment, the molecules of the present invention are prepared as shown in Scheme VII.

Scheme VII

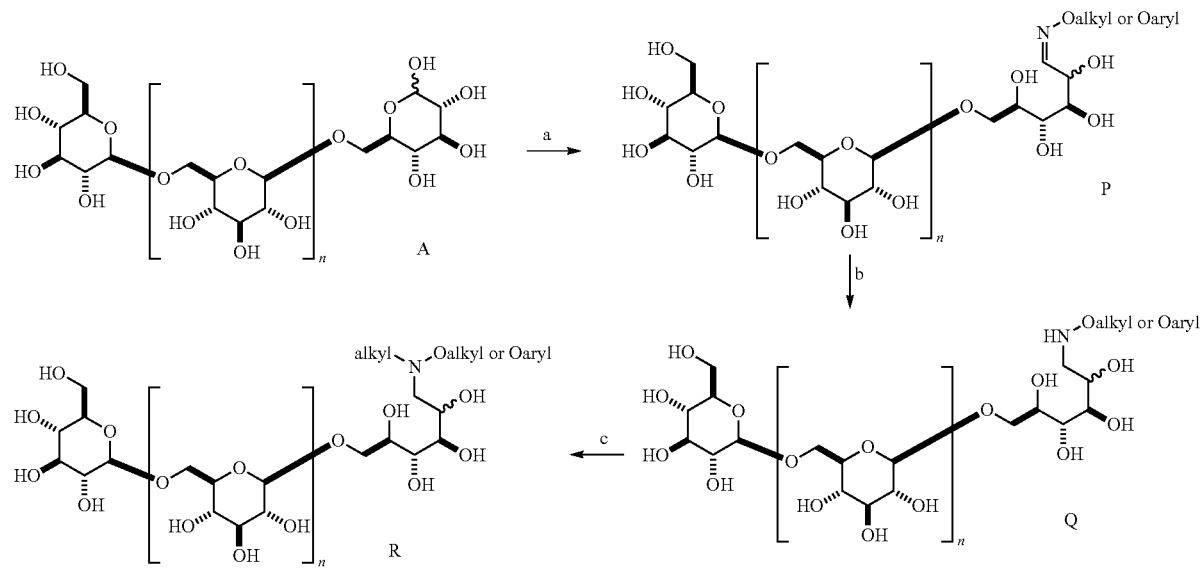

Reagents and Conditions: a) H$_2$NOalkyl or H$_2$NOaryl; b) NaCNBH$_3$; c) CH$_2$O or alkylCHO or arylCHO, NaBH$_3$CN, A β-1,6-D-glucan starting material A containing a C-1 hydroxyl is reacted with an alkyloxyamine to form an oxime P. The oxime is reduced to an amine Q, and the amine is alkylated under conditions of reductive alkylation with an alkyl or aryl aldehyde to give a trisubstituted amine R. The reduced oximes of Scheme VII are novel compositions of matter.

In another embodiment of the present invention is shown in Scheme VIII.

Scheme VIII

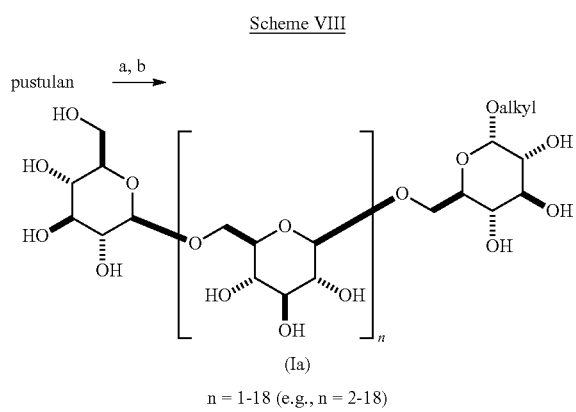

n = 1-18 (e.g., n = 2-18)

Reagents and Conditions: a) TfOH, HOalkyl, heat; b) size exclusion chromatography This scheme expands the scope of synthesis of O-alkyl glycosides of β-1,6-D-glucan from other synthetic methods [Hattori, T. et al. Carbohydrate Res. 366, 6-16, 2013]. Scheme VIII employs the reaction of pustulan with an alkyl alcohol and triflic acid to produce a mixture of 3- to 20-mer O-alkyl glycosides, in which the configuration at the anomeric carbon is largely α. This mixture is separated into the individual oligomeric β-1,6-D-glucan-α-O-alkyl glycosides (Ia). The α-methoxy compositions of scheme VII are novel.

In another embodiment of the present invention as shown in Scheme IX the molecules of the present invention (Ib) contain a substituted thio group at C-1.

In one embodiment of this scheme, a β-1,6-D-glucan starting material A containing a C-1 hydroxyl is reacted with acetic anhydride/sodium acetate to produce a per-acetylated glycoside as in scheme II. This intermediate B is reacted with an alkylthiol, substituted alkylthiol, alkenylthiol, alkynylthiol, alkylenethiol, alkynylene thiol, arylthiol, or heteroarylthiol and a Lewis acid catalyst to produce an acetylated β-1,6-D-glucan thioglycoside S. This material is reacted with NaOMe/MeOH to give T, wherein R is alkyl, alkenyl, alkynyl, alkylene, alkynylene, aryl or heteroaryl. In some embodiments, R is unsubstituted. In other embodiments, R is substituted.

In one embodiment of Scheme IX ethane thiol is used to react with the per-acetylated glycoside in the presence of boron trifluoride diethyl etherate to give a per-acetylated ethylthioglycoside. Hydrolysis of this product gives a compound (Ib) wherein R is ethyl. Compounds of this structure are novel compositions of matter.

In a variation of this scheme, the target β-1,6-D-glucan thioglycoside, having β as the predominant stereochemistry at the anomeric center is formed directly from the reaction of a β-1,6-D-glucan with an aryl or heteroaryl thiol and 2-chloro-1,3-dimethylimidazolium chloride [Tanaka, T. et al., Chem. Left. 38, 458-459, 2009]. The arylthio- and heteroarylthioglycosides of the β-1,6-D-glucan 3-mer to 20-mer are novel compositions of matter. In another embodiment of the present invention as shown in Scheme X the molecules of the present invention (Ib) contain an alkyl or aryl thio group at C-1. Reaction of pustulan with an alkyl or aryl thiol and acid produces a mixture of oligomeric

Scheme IX

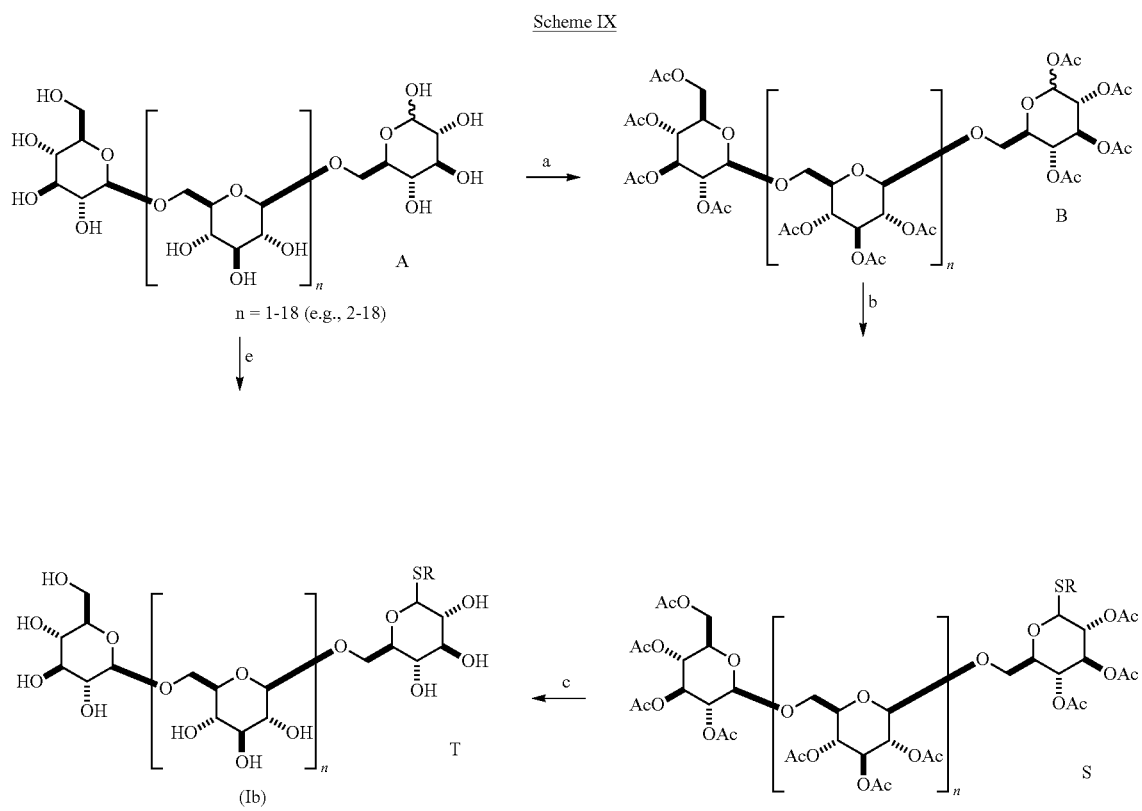

Reagents and Conditions: a) Ac₂O, NaOAc, solvent, heat; b) RSH, BF₃-Et₂O; c) NaOMe, MeOH; e) 2-chloro-1,3-dimethylimidazolium chloride, Et₃N, acetonitrile, H₂O.

β-1,6-D-glucan thioglycosides, which are separated into individual compounds with size exclusion chromatography.

Scheme X

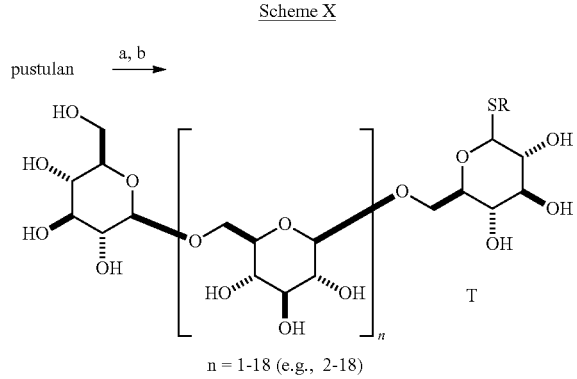

n = 1-18 (e.g., 2-18)

Reagents and Conditions: a) TfOH, HSalkyl or HSaryl, heat; b) size exclusion chromatography In another embodiment of the present invention as shown in Scheme XI composition (Ia) wherein R is alkyl is selectively oxidized to give an acid of composition (Ic).

Scheme XI

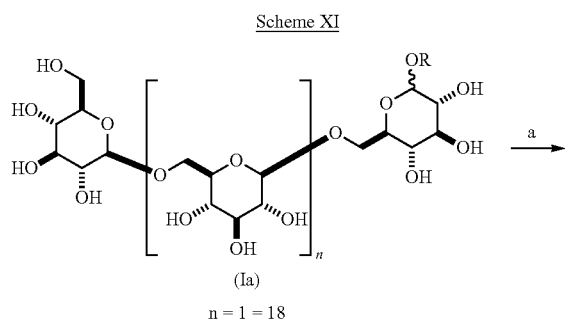

n = 1 = 18

Reagents and Conditions: a) TEMPO, $NaHCO_3$, $Ca(OCl)_2$, t-BuOCl

In another embodiment of the present invention as shown in Scheme XII composition (Ia) wherein R is alkyl is selectively oxidized to give an aldehyde of composition (Id). TEMPO has been used to oxidize methyl glycosides of unprotected mono-saccharides to give unprotected dialdoglycosides [Angelin, M. et al. Eur. J. Org. Chem. 4323-4326, 2006]. The aldehydes of formula (Id) wherein R is methyl are novel compositions of matter.

Scheme XII

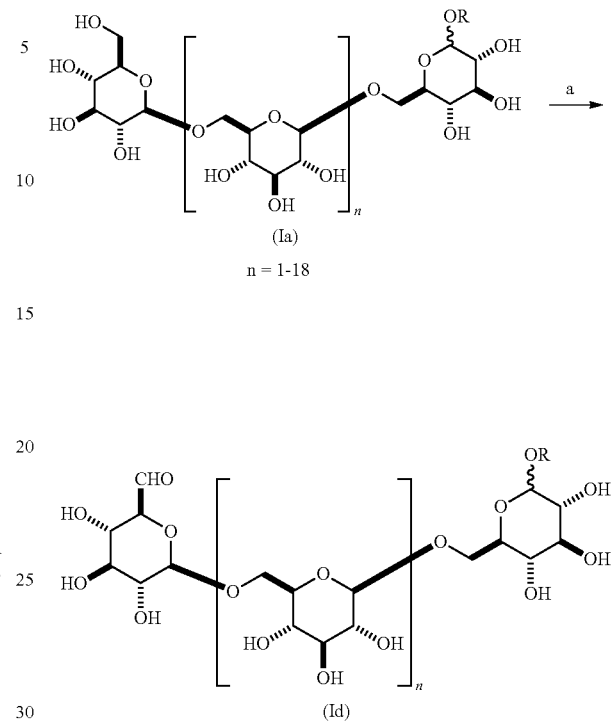

Reagents and Conditions: a) TEMPO, $Ca(OCl)_2$

EXAMPLES

Unless specified otherwise, starting materials are generally available from commercial sources such as Sigma-Aldrich Chemicals Co. (Milwaukee, Wis), VWR Scientific (Radnor, Pa.), and Fisher Scientific. The following acronyms used in the examples below have the corresponding meanings.

| | |
|---|---|
| DCM | dichloromethane |
| DMSO | dimethylsulfoxide |
| DMC | 2-chloro-1,3-dimethylimidazolium chloride |
| TfOH | trifluoromethanesulfonic acid |
| SEC | size exclusion chromatography |
| TEMPO | (2,2,6,6-tetramethylpiperidin-1-yl)oxyl |
| RT | room temperature |
| HPLC | high pressure liquid chromatography |
| HILIC | hydrophobic interaction liquid chromatography |
| LCMS | liquid chromatography mass spectrometry |
| ELSD | electrospray detection |
| IPA | isopropanol |
| TMSOTf | trimethylsilyltriflate |
| Ac | acetyl |
| Bz | benzoyl |
| ThexylDMS | dimethylthexylsilyl |
| DIPEA | diisopropylethylamine |
| TFA | trifluoroacetic acid |
| MeOH | methanol |
| EtOH | ethanol |
| BuOH | butanol |

Example 1

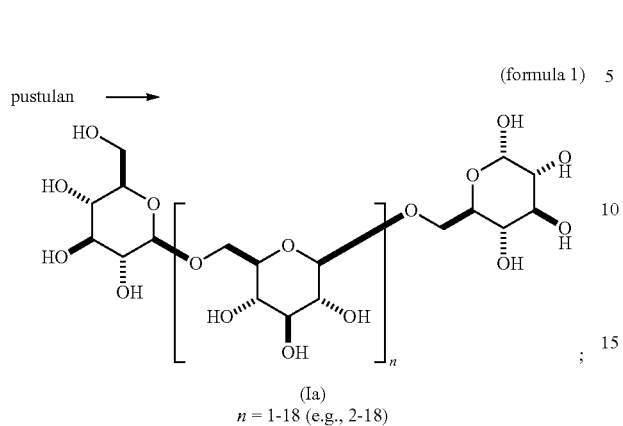

(formula 1)

(Ia)
n = 1-18 (e.g., 2-18)

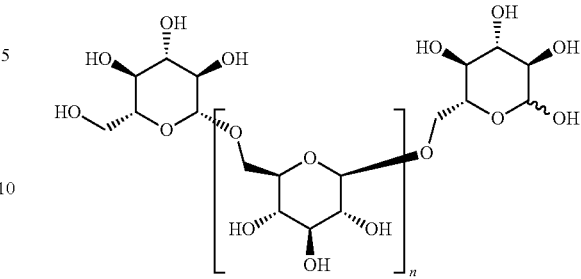

(formula 2)

To a 100-mL round bottom flask containing pustulan (6.12 grams, 0.153 mmol; dry, tan powder) was added 61 mL concentrated HCl. The resulting mixture was stirred vigorously at room temperature (23° C.) for 1.75 h, during which time the mixture thinned out noticeably. At the end of the stirring time a fine, black slurry remained in the flask. The mixture was transferred to a beaker containing 427 mL n-propanol to induce precipitation. The mixture was transferred to centrifuge tubes and the solid material was separated from the liquid by centrifugation 1000×g, 5 min). The supernatant (containing HCl salts and lower order sugars) was decanted to provide light brown pellets. The pellets were washed successively with ethanol (2×10 mL) and n-propanol (1×10 mL) to remove traces of lower order sugars (mono- and di-saccharides). Water (3.0 mL per tube) was then added to each tube (partial solubility) and the subsequent mixtures were stirred overnight (stir plate) at room temperature. Centrifugation of the tubes yielded dark brown pellets (precipitation of unreacted polymeric material) and clear supernatants. Pooling of the supernatants and freeze-drying yielded the target mixture of β-1,6-D-glucans as a tan powder (2.673 g, 44% by mass). Size range: 1- to 20-mer; with the bulk of material in the 3- to 8-mer range (as determined by LC/MS-ELSD analysis).

Example 2

HILIC method of purification—The oligosaccharide was dissolved in either minimal amounts of water or DMSO. The sample was introduced to a Waters Xbridge Amide 5 μm column (19×250 mm) The purified oligosaccharide was eluted from the column utilizing a gradient of 80% acetonitrile w/ 0.1% triethylamine:20% water w/ 0.1% triethylamine to 35% acetonitrile w/ 0.1% triethylamine:65% water w/ 0.1% triethylamine. Alternatively, 0.1% ammonium hydroxide was utilized in place of triethylamine. This method was useful in isolating individual β-1,6-glucan oligomers containing from 1 to 20 D-glucose units.

In addition to the 3-mer to 9-mer β-1,6-D-glucan oligomers, there were obtained the following compounds:

2a. a 10-mer (n=8), [O-β-D-glucopyranosyl-1,6-]$_9$-D-glucose: m/z=1639 (M+H$^+$), 1657 (M+NH$_4{}^+$), 1662 (M+Na$^+$);

2b. an 11-mer (n=9), [O-β-D-glucopyranosyl-1,6]$_{10}$-D-glucose: m/z=1802 (M+H$^+$), 1819 (M+NH$_4{}^+$), 1824 (M+Na$^+$);

2c. a 12-mer (n=10), [O-β-D-glucopyranosyl-1,6-]$_{11}$-D-glucose: m/z=1964 (M+H$^+$), 1981 (M+NH$_4{}^+$), 1986 (M+Na$^+$);

2d. a 13-mer (n=11), [O-β-D-glucopyranosyl-1,6-]$_{12}$-D-glucose: m/z=2126 (M+H$^+$), 2148 (M+Na$^+$);

2e. a 14-mer (n=12), [O-β-D-glucopyranosyl-1,6-]$_{13}$-D-glucose: m/z=2288 (M+H$^+$), 2310 (M+Na$^+$);

2f. a 15-mer (n=13), [O-β-D-glucopyranosyl-1,6-]$_{14}$-D-glucose: m/z=2450 (M+H$^+$), 2472 (M+Na$^+$);

2g. a 16-mer (n=14), [O-β-D-glucopyranosyl-1,6-]$_{15}$-D-glucose: m/z=2611 (M+H$^+$), 2633 (M+Na$^+$);

2h. a 17-mer (n=15), [O-β-D-glucopyranosyl-1,6-]$_{16}$-D-glucose: m/z=2774 (M+H$^+$), 2796 (M+Na$^+$);

2i. an 18-mer (n=16), [O-β-D-glucopyranosyl-1,6-]$_{17}$-D-glucose: m/z=2936 (M+H$^+$), 2958 (M+Na$^+$);

2j. a 19-mer (n=17), [O-β-D-glucopyranosyl-1,6-]$_{18}$-D-glucose: m/z=3098 (M+H$^+$), 3120 (M+Na$^+$); and 2k. a 20-mer (n=18), [O-β-D-glucopyranosyl-1,6-]$_{19}$-D-glucose: m/z=3260 (M+H$^+$), 3282 (M+Na$^+$).

Example 3

Separation of Oligosaccharides by SEC

Separations were carried out using a P2 resin (Bio-rad) in which fines had been removed. The resin was packed onto two 1-meter XK 50/100 columns (GE Healthcare) connected in series, such that the bottom of column 1 was connected to the top of column 2 Separations were achieved isocratically with an Agilent 1100 HPLC system, using 0.1 M acetic acid as the mobile phase at a flow rate of 3.5 mL/min. Samples were injected at the top of column 1 and eluted materials were collected at the bottom of column 2 using a fraction collector. Sample size ranged from 5-13 mL with concentrations from 0.1 to 0.2 g/mL. Fractions were analyzed using a MALDI-TOF 4800 (ABSciex) using 4'-hydroxyazobenzene-2-carboxylic acid (Sigma-Aldrich) as the matrix in reflectron positive mode.

The separations were performed using one of two procedures: in the first procedure, a sample was injected at the top of column 1 and fractions were collected as they eluted from the end column 2 In this method, the mobile phase was pumped from a reservoir containing 0.1 M acetic acid. Using the first procedure, carbohydrates from nine units to one unit in length were resolved and were purified. In the second procedure, initially, columns were connected in a loop, so the mobile phase that eluted from the bottom of column 2 was used to feed the top of column 1 Injected samples were run in this looped arrangement to extend the length of column. After the injected sample had passed through the second column once, the loop was opened and column 1 was fed from a reservoir containing 0.1 M acetic acid. Subsequently, fractions were collected as they elute from the bottom of column 2 The second procedure permitted the resolution and isolation of carbohydrates from eleven units to one unit in length.

Example 4

Methanolysis of Pustulan

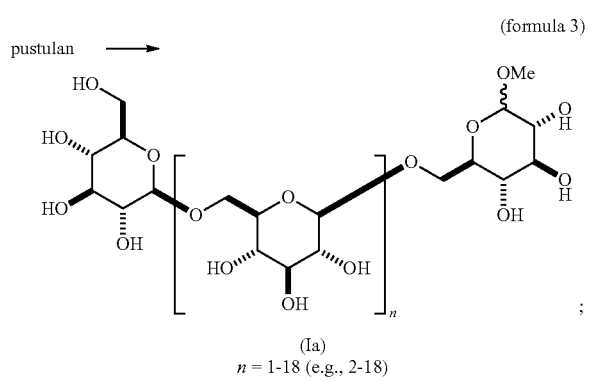

A solution of pustulan (1.4 g, 0.038 mmol) in MeOH (6.1 mL) and DMSO (37.8 mL) was treated with TfOH (47.0 μL, 14 equiv). The reaction mixture was warmed to 80° C. After 6 h, TLC analysis showed conversion of the pustulan to a ladder of oligomers ranging from 3-mer and higher. The products were precipitated out with acetonitrile (300 mL) and a pellet formed via centrifugation (3000 rpm×5 min) The supernatant was removed and the pellet was suspended in water (10 mL) and was warmed to 50° C. to obtain solution. The mixture was then centrifuged (3000 rpm×5 min) and the supernatant was separated from the pellet. This solution was purified by P2 SEC.

Example 5

Preparation of methyl [O-β-D-glucopyranosyl-1,6]$_5$-D-glucopyranoside

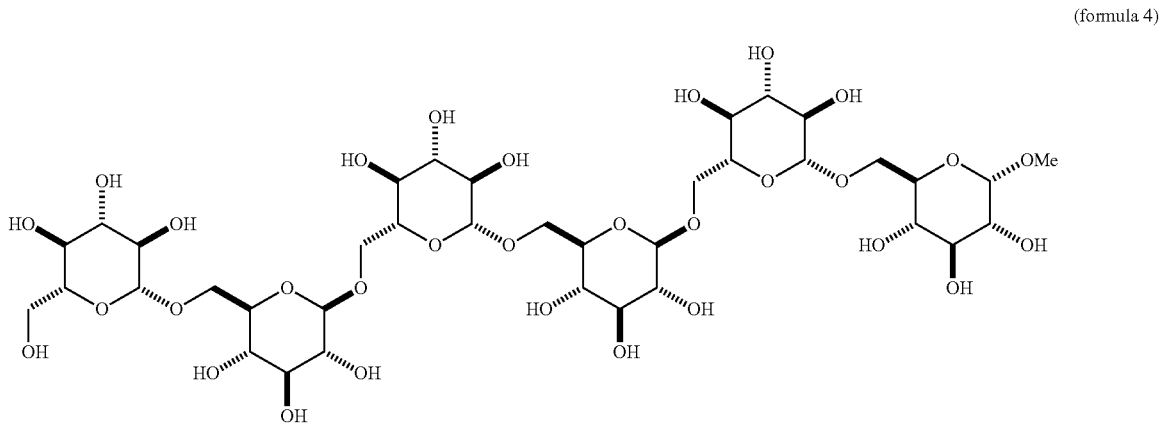 [SMILES: CO[C@H]1O[C@H](CO[C@@H]2O[C@H](CO[C@@H]3O[C@H](CO[C@@H]4O[C@H](CO[C@@H]5O[C@H](CO[C@@H]6O[C@H](CO)[C@@H](O)[C@H](O)[C@H]6O)[C@@H](O)[C@H](O)[C@H]5O)[C@@H](O)[C@H](O)[C@H]4O)[C@@H](O)[C@H](O)[C@H]3O)[C@@H](O)[C@H](O)[C@H]2O)[C@@H](O)[C@H](O)[C@H]1O]

The oligosaccharide mixture from Example 4 is dissolved in either minimal amounts of water or DMSO. The sample is introduced to the Waters Xbridge Amide 5 μm column (19×250 mm) The purified oligosaccharide is eluted from the column utilizing a gradient of 80% Acetonitrile w/ 0.1% triethylamine:20% water w/ 0.1% triethylamine to 35% Acetonitrile w/ 0.1% triethylamine:65% water w/ 0.1% triethylamine. Alternatively, 0.1% ammonium hydroxide may be utilized in place of triethyl amine. The individual oligomeric β-1,6-D-glucans appeared as pairs of α- and β-OMe anomers with the α-anomer as the predominant isomer. The title compound is obtained by evaporation of the appropriate eluent. m/z=1005 (M+H$^+$), 1022 (M+NH$_4^+$), 1027 (M+Na$^+$).

Similarly prepared by the method of Example 4 were:
a. Compounds of Formula 5

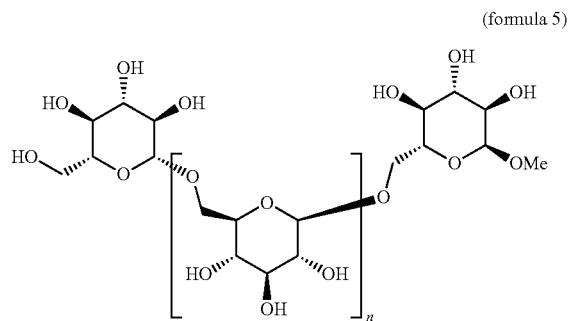

(formula 5)

5a. a 3-mer (n=1), methyl [O-β-D-glucopyranosyl-1,6]$_2$-D-glucopyranoside: m/z=519 (M+H$^+$), 541 (M+NH$_4^+$), 546 (M+Na$^+$);

5b. a 4-mer (n=2), methyl [O-β-D-glucopyranosyl-1,6]$_3$-D-glucopyranoside: m/z=681 (M+H$^+$), 698 (M+NH$_4^+$), 703 (M+Na$^+$);

5c. a 5-mer (n=3), methyl [O-β-D-glucopyranosyl-1,6-]$_4$-D-glucopyranoside: m/z=843 (M+H$^+$), 860 (M+NH$_4^+$), 865 (M+Na$^+$);

5d. a 7-mer (n=5), methyl [O-β-D-glucopyranosyl-1,6]$_6$-D-glucopyranoside: m/z=1167 (M+H$^+$), 1184 (M+NH$_4^+$), 1189 (M+Na$^+$);

5e. an 8-mer (n=6), methyl [O-β-D-glucopyranosyl-1,6]$_7$-D-glucopyranoside: m/z=1329 (M+H$^+$), 1346 (M+NH$_4^+$), 1351 (M+Na$^+$);

5f. a 9-mer (n=7), methyl [O-β-D-glucopyranosyl-1,6]$_8$-D-glucopyranoside: m/z=1491 (M+H$^+$), 1508 (M+NH$_4^+$), 1513 (M+Na$^+$);

5g. a 10-mer (n=8), methyl [O-β-D-glucopyranosyl-1,6]$_9$-D-glucopyranoside: m/z=1654 (M+H$^+$), 1671 (M+NH$_4^+$), 1676 (M+Na$^+$);

5h. an 11-mer (n=9), methyl [O-β-D-glucopyranosyl-1,6]$_{10}$-D-glucopyranoside: m/z=1816 (M+H$^+$), 1833 (M+NH$_4^+$), 1838 (M+Na$^+$);

5i. a 12-mer (n=10), methyl [O-β-D-glucopyranosyl-1,6]$_{11}$-D-glucopyranoside: m/z=1978 (M+H$^+$), 1995 (M+NH$_4^+$), 2000 (M+Na$^+$);

5j. a 13-mer (n=11), methyl [O-β-D-glucopyranosyl-1,6]$_{12}$-D-glucopyranoside: m/z=2140 (M+H$^+$);

5k. a 14-mer (n=12), methyl [O-β-D-glucopyranosyl-1,6]$_{13}$-D-glucopyranoside: m/z=2302 (M+H$^+$);

5l. a 15 mer (n=13), methyl [O-β-D-glucopyranosyl-1,6]$_{14}$-D-glucopyranoside: m/z=2464 (M+H$^+$);

5m. a 16-mer (n=14), methyl [O-β-D-glucopyranosyl-1,6]$_{15}$-D-glucopyranoside: m/z=2626 (M+H$^+$);

5n. a 17-mer (n=15), methyl [O-β-D-glucopyranosyl-1,6]$_{16}$-D-glucopyranoside: m/z=2788 (M+H$^+$);

5o. an 18-mer (n=16), methyl [O-β-D-glucopyranosyl-1,6]$_{17}$-D-glucopyranoside: m/z=2950 (M+H$^+$);

5p. a 19-mer (n=17), methyl [O-β-D-glucopyranosyl-1,6]$_{18}$-D-glucopyranoside: m/z=3112 (M+H$^+$);

and 5q. a 20-mer (n=18), methyl [O-β-D-glucopyranosyl-1,6]$_{19}$-D-glucopyranoside: m/z=3274 (M+H$^+$).

b. Compounds of Formula 6

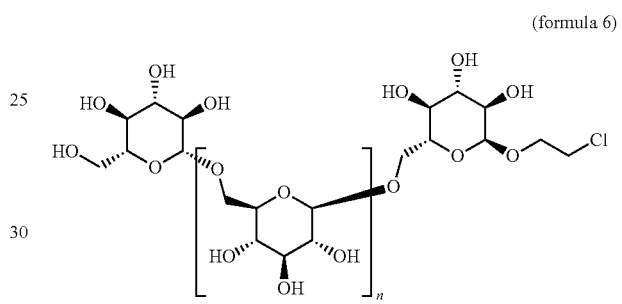

(formula 6)

6a. a 3-mer (n=1), 2-chloroethyl [O-β-D-glucopyranosyl-1,6]$_2$-D-glucopyranoside: m/z=567 (M+H$^+$), 584 (M+NH$_4^+$), 589 (M+Na$^+$);

6b. a 4-mer (n=2), 2-chloroethyl [O-β-D-glucopyranosyl-1,6]$_3$-D-glucopyranoside: m/z=729 (M+H$^+$), 746 (M+NH$_4^+$), 751 (M+Na$^+$);

6c. a 5-mer (n=3), 2-chloroethyl [O-β-D-glucopyranosyl-1,6]$_4$-D-glucopyranoside: m/z=891 (M+H$^+$), 908 (M+NH$_4^+$), 913 (M+Na$^+$);

6d. a 6-mer (n=4), 2-chloroethyl [O-β-D-glucopyranosyl-1,6]$_5$-D-glucopyranoside: m/z=1053 (M+H$^+$), 1070 (M+NH$_4^+$), 1075 (M+Na$^+$);

6e. a 7-mer (n=5), 2-chloroethyl [O-β-D-glucopyranosyl-1,6]$_6$-D-glucopyranoside: m/z=1215 (M+H$^+$), 1232 (M+NH$_4^+$), 1237 (M+Na$^+$);

6f. an 8-mer (n=6), 2-chloroethyl [O-β-D-glucopyranosyl-1,6]$_7$-D-glucopyranoside: m/z=1377 (M+H$^+$), 1394 (M+NH$_4^+$), 1399 (M+Na$^+$); and 6g. a 9-mer (n=7), 2-chloroethyl [O-β-D-glucopyranosyl-1,6]$_8$-D-glucopyranoside: m/z=1539 (M+H$^+$), 1556 (M+NH$_4^+$), 1561 (M+Na$^+$).

Example 6

Preparation of methyl O-β-D-glucopyranurosyl-1,6-[O-β-D-glucopyranosyl-1,6]$_4$-D-glucopyranoside

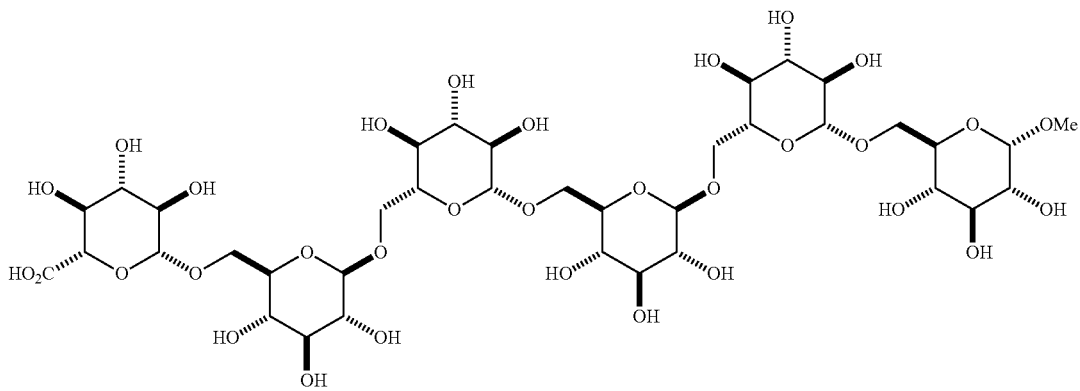

(formula 7)

A solution of the product from Example 5 (1.8 mg, 1.8 μmole) in satd. aq. NaHCO$_3$ (10 μL) was cooled to 0° C. and was successively treated with TEMPO (10 mg/mL in satd. aq. NaHCO$_3$) (2.8 μL, 0.2 μmole, 0.1 equiv.), Ca(OCl)$_2$ (0.6 mg, 3.9 μmol, 2.2 equiv.) and tert-butylhypochlorite (70 wt % in water) (0.6 μL, 3.9 μmol, 2.2 equiv.). After stirring for 4 hrs, solution was desalted by passage through a centrifuge column of P2 (0.5 g, 6×100 uL) and the combined elute was freeze dried and was then further purified by HPLC purification on a HILIC column (4.6×250 mm, 80-35% acetonitrile/water w/ 0.1% ammonium hydroxide, λ=220 nm). The title compound was obtained by evaporation of the appropriate eluent. m/z=1019 (M+H$^+$), 1041 (M+Na$^+$).

Similarly prepared by the method of this example were:

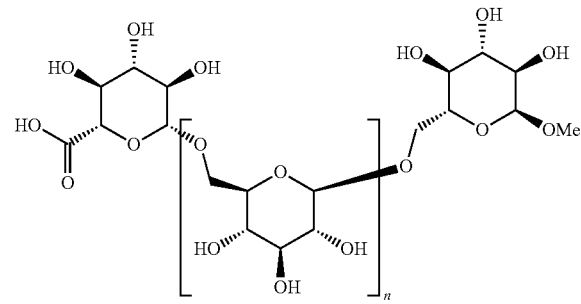

(formula 8)

8a. a 4-mer (n=2), methyl O-β-D-glucopyranurosyl-1,6-[O-β-D-glucopyranosyl-1,6]$_2$-D-glucopyranoside; m/z=695 (M+H$^+$);

8b. a 5-mer (n=3), methyl O-β-D-glucopyranurosyl-1,6-[O-β-D-glucopyranosyl-1,6]$_3$-D-glucopyranoside m/z=857 (M+H$^+$);

8c. a 7-mer (n=5), methyl O-β-D-glucopyranurosyl-1,6-[O-β-D-glucopyranosyl-1,6]$_5$-D-glucopyranoside; m/z=1181 (M+H$^+$);

8d. an 8-mer (n=6), methyl O-β-D-glucopyranurosyl-1,6-[O-β-D-glucopyranosyl-1,6]$_6$-D-glucopyranoside: m/z=1343 (M+H$^+$); and 8e. a 9-mer (n=7), methyl O-β-D-glucopyranurosyl-1,6-[O-β-D-glucopyranosyl-1,6]$_7$-D-glucopyranoside: m/z=1505 (M+H$^+$).

Example 7

Preparation of methyl O-β-D-gluco hexodialdo-1,5-pyranosyl-1,6-[O-β-D-glucopyranosyl-1,6]₄-D-glucopyranoside

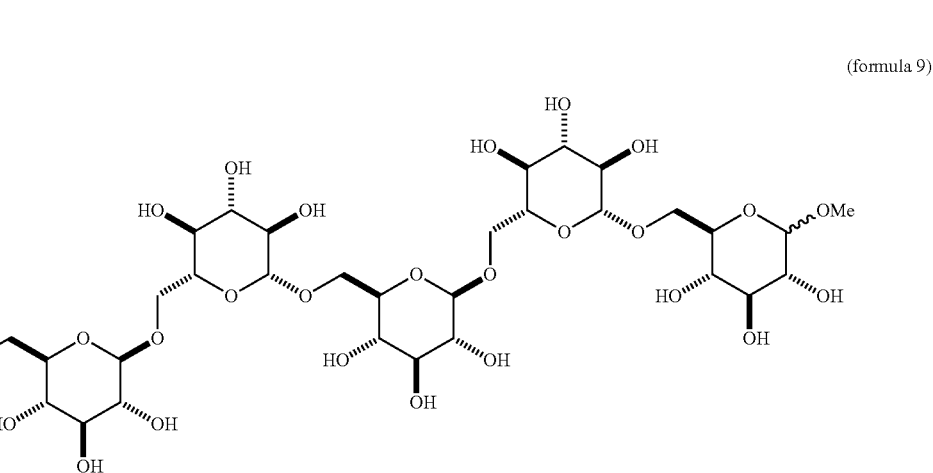

(formula 9)

A solution of the product from example 5 (2.0 mg, 2.0 μmole) in DMF (15 μL) is cooled to 0° C. and is treated with NaHCO₃ (1.7 mg, 20 μmole, 10 equiv), TEMPO (10 mg/mL in DMF) (3.1 μL, 0.2 mmole, 0.1 equiv.), and Ca(OCl)₂ (0.6 mg, 4.4 mmol, 2.2 equiv.). After stirring for 8 hrs, the solution is desalted by passage through a centrifuge column of P2 (0.5 g, 6×100 μL) and the combined elute is freeze dried and then is further purified by HPLC purification on a HILIC column (4.6×250 mm, 80-35% acetonitrile/water w/ 0.1% ammonium hydroxide, λ=220 nm). The title compound is obtained by evaporation of the appropriate eluent. m/z=1003 (M+H⁺), 1025 (M+Na⁺)

Example 8

Ethyl [O-β-D-glucopyranosyl-1,6]₅-1-thio-D-glucopyranoside

A solution of pustulan (1.4 g, 0.038 mmole) in ethyl thiol (10 mL) and DMSO (37.8 mL) was treated with TfOH (47.0 mL, 14 equiv). The reaction mixture is warmed to 80° C. After 6 hrs, TLC analysis shows conversion of the pustulan to a ladder of oligomers ranging from 3mer and higher. The products are precipitated out with acetonitrile (300 mL) and a pellet is formed via centrifugation (3000 rpm×5 min). The supernatant is removed and the pellet is suspended in water (10 mL) and warmed to 50° C. to obtain solution. The mixture is then centrifuged (3000 rpm×5 min) and the supernatant is separated from the pellet. The solution of oligosaccharide ladder is purified by P2 size exclusion chromatography.

(compound 10)

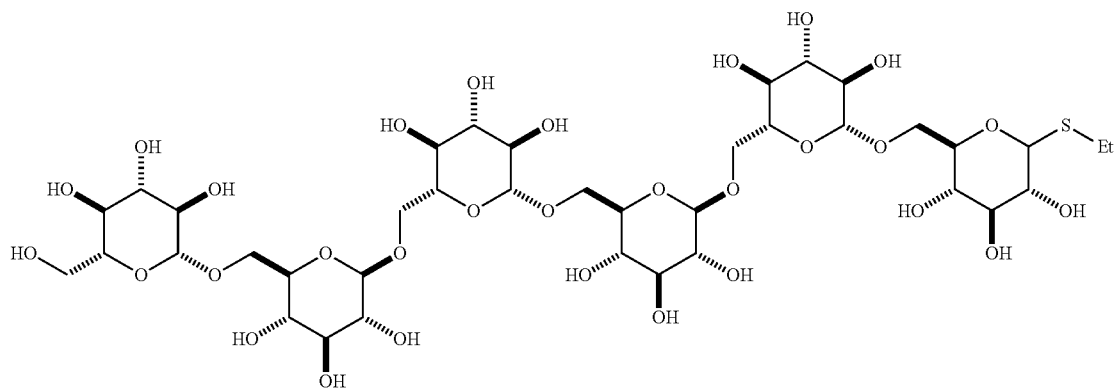

Similarly prepared by the method of this example are were:

a. Compounds of Formula 11:

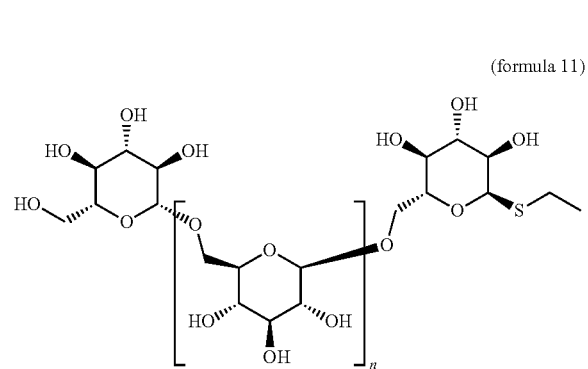

(formula 11)

11a. a 3-mer (n=1), Ethyl [O-β-D-glucopyranosyl-1,6]$_2$-1-thio-D-glucopyranoside: m/z=549 (M+H$^+$);

11b. a 4-mer (n=2), Ethyl [O-β-D-glucopyranosyl-1,6]$_3$-1-thio-D-glucopyranoside: m/z=711 (M+H$^+$);

11c. a 5-mer (n=3), Ethyl [O-β-D-glucopyranosyl-1,6]$_4$-1-thio-D-glucopyranoside: m/z=873 (M+H$^+$);

11d. a 7-mer (n=5), Ethyl [O-β-D-glucopyranosyl-1,6]$_6$-1-thio-D-glucopyranoside: m/z=1197 (M+H$^+$);

11e. an 8-mer (n=6), Ethyl [O-β-D-glucopyranosyl-1,6]$_7$-1-thio-D-glucopyranoside: m/z=1359 (M+H$^+$);

11f. a 9-mer (n=7), Ethyl [O-β-D-glucopyranosyl-1,6]$_8$-1-thio-D-glucopyranoside: m/z=1521 (M+H$^+$);

11g. a 10-mer (n=8), Ethyl [O-β-D-glucopyranosyl-1,6]$_9$-1-thio-D-glucopyranoside: m/z=1683 (M+H$^+$);

11h. a 11-mer (n=9), Ethyl [O-β-D-glucopyranosyl-1,6]$_{10}$-1-thio-D-glucopyranoside: m/z=1845 (M+H$^+$);

11i. a 12-mer (n=10), Ethyl [O-β-D-glucopyranosyl-1,6]$_{11}$-1-thio-D-glucopyranoside: m/z=2007 (M+H$^+$);

11j. a 13-mer (n=11), Ethyl [O-β-D-glucopyranosyl-1,6]$_{12}$-1-thio-D-glucopyranoside: m/z=2169 (M+H$^+$);

11k. a 14-mer (n=12), Ethyl [O-β-D-glucopyranosyl-1,6]$_{13}$-1-thio-D-glucopyranoside: m/z=2331 (M+H$^+$);

11l. a 15-mer (n=13), Ethyl [O-β-D-glucopyranosyl-1,6]$_{14}$-1-thio-D-glucopyranoside: m/z=2493 (M+H$^+$);

11m. a 16-mer (n=14), Ethyl [O-β-D-glucopyranosyl-1,6]$_{15}$-1-thio-D-glucopyranoside: m/z=2655 (M+H$^+$);

11n. a 17-mer (n=15), Ethyl [O-β-D-glucopyranosyl-1,6]$_{16}$-1-thio-D-glucopyranoside: m/z=2817 (M+H$^+$);

11o. a 18-mer (n=16), Ethyl [O-β-D-glucopyranosyl-1,6]$_{17}$-1-thio-D-glucopyranoside: m/z=2979 (M+H$^+$);

11p. a 19-mer (n=17), Ethyl [O-β-D-glucopyranosyl-1,6]$_{18}$-1-thio-D-glucopyranoside: m/z=3141 (M+H$^+$); and 11q. a 20-mer (n=18), Ethyl [O-β-D-glucopyranosyl-1,6]$_{19}$-1-thio-D-glucopyranoside: m/z=3303 (M+H$^+$).

b. Compounds of Formula 12:

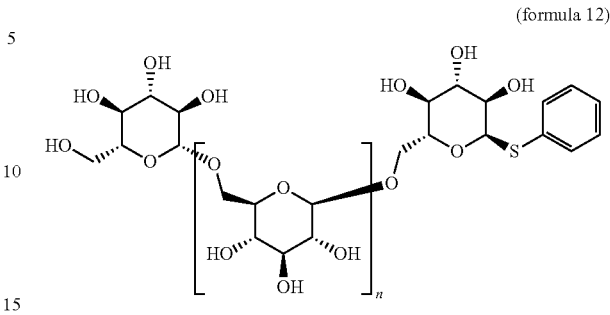

(formula 12)

12a. a 3-mer (n=1), Phenyl [O-β-D-glucopyranosyl-1,6]$_2$-1-thio-D-glucopyranoside: m/z=597 (M+H$^+$);

12b. a 4-mer (n=2), Phenyl [O-β-D-glucopyranosyl-1,6]$_3$-1-thio-D-glucopyranoside: m/z=759 (M+H$^+$);

12c. a 5-mer (n=3), Phenyl [O-β-D-glucopyranosyl-1,6]$_4$-1-thio-D-glucopyranoside: m/z=921 (M+H$^+$);

12d. a 6-mer (n=4), Phenyl [O-β-D-glucopyranosyl-1,6]$_5$-1-thio-D-glucopyranoside: m/z=1083 (M+H$^+$);

12e. a 7-mer (n=5), Phenyl [O-β-D-glucopyranosyl-1,6]$_6$-1-thio-D-glucopyranoside: m/z=1245 (M+H$^+$);

12f. an 8-mer (n=6), Phenyl [O-β-D-glucopyranosyl-1,6]$_7$-1-thio-D-glucopyranoside: m/z=1407 (M+H$^+$);

12g. a 9-mer (n=7), Phenyl [O-β-D-glucopyranosyl-1,6]$_8$-1-thio-D-glucopyranoside: m/z=1569 (M+H$^+$);

12h. a 10-mer (n=8), Phenyl [O-β-D-glucopyranosyl-1,6]$_9$-1-thio-D-glucopyranoside: m/z=1731 (M+H$^+$);

12i. a 11-mer (n=9), Phenyl [O-β-D-glucopyranosyl-1,6]$_{10}$-1-thio-D-glucopyranoside: m/z=1893 (M+H$^+$);

12j. a 12-mer (n=10), Phenyl [O-β-D-glucopyranosyl-1,6]$_{11}$-1-thio-D-glucopyranoside: m/z=2055 (M+H$^+$);

12k. a 13-mer (n=11), Phenyl [O-β-D-glucopyranosyl-1,6]$_{12}$-1-thio-D-glucopyranoside: m/z=2217 (M+H$^+$);

12l. a 14-mer (n=12), Phenyl [O-β-D-glucopyranosyl-1,6]$_{13}$-1-thio-D-glucopyranoside: m/z=2379 (M+H$^+$);

12m. a 15-mer (n=13), Phenyl [O-β-D-glucopyranosyl-1,6]$_{14}$-1-thio-D-glucopyranoside: m/z=2541 (M+H$^+$);

12n. a 16-mer (n=14), Phenyl [O-β-D-glucopyranosyl-1,6]$_{15}$-1-thio-D-glucopyranoside: m/z=2703 (M+H$^+$);

12o. a 17-mer (n=15), Phenyl [O-β-D-glucopyranosyl-1,6]$_{16}$-1-thio-D-glucopyranoside: m/z=2865 (M+H$^+$);

12p. a 18-mer (n=16), Phenyl [O-β-D-glucopyranosyl-1,6]$_{17}$-1-thio-D-glucopyranoside: m/z=3027 (M+H$^+$);

12q. a 19-mer (n=17), Phenyl [O-β-D-glucopyranosyl-1,6]$_{18}$-1-thio-D-glucopyranoside: m/z=3189 (M+H$^+$); and 12r. a 20-mer (n=18), Phenyl [O-β-D-glucopyranosyl-1,6]$_{19}$-1-thio-D-glucopyranoside: m/z=3351 (M+H$^+$).

Example 9

[(2R,3R,4R,5RS)-2,3,4,5-tetrahydroxy-6-(N-methyl-N-(2-azidoethyl)amino]hexyl [O-β-D-glucopyranosyl-1,6]₄-β-D-glucopyranoside

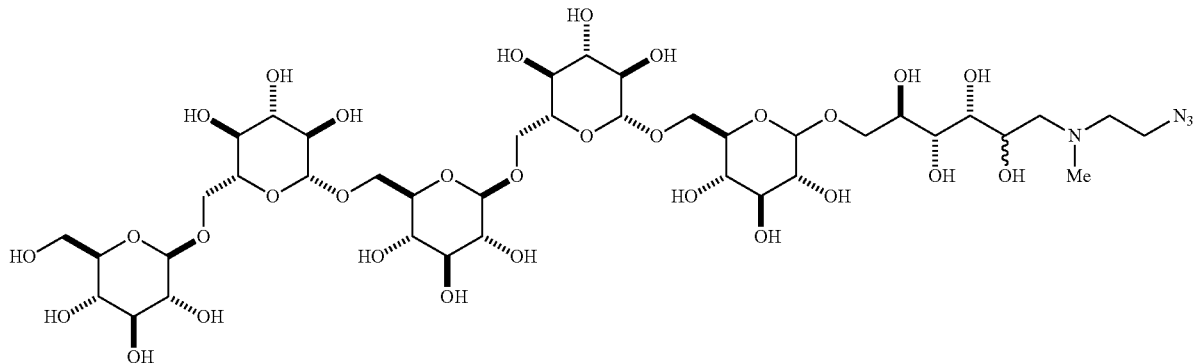

(formula 13)

A solution of [O-β-D-glucopyranosyl-1,6]₅-D-glucopyranoside (16 mg, 16 µmole) in 100 mM sodium acetate buffer pH=4.0 (150 µL) was successively treated with 2-azidoethylamine HCl (5.9 mg, 48 µmole, 3 equiv) and then sodium cyanoborohydride (6.1 mg, 97 µmole, 6 equiv) and then was warmed to 40° C. After stirring for 24 h, LC/MS analysis showed clean conversion to the desired product. The reaction mixture was then cooled to room temperature and was then subjected to 37% aqueous formaldehyde (13 µL, 160 µmole, 10 equiv) and then additional sodium cyanoborohydride (10.1 mg, 160 µmole, 10 equiv). After stirring for 3h, LC/MS analysis showed clean conversion to the desired product. The mixture was desalted by passage through a centrifuge column of P2 (5 g, 6×300 uL) and the combined elutes were freeze dried and then further purified by HPLC purification on a HILIC column (4.6×250 mm, 80-35% acetonitrile/water w/ 0.1% ammonium hydroxide, λ=220 nm) to yield the desired product: m/z=1075 (M+H⁺), 1092 (M+NH₄⁺), 1097 (M+Na⁺).

Similarly prepared by the method of this example were:
a. Compounds of Formula 14

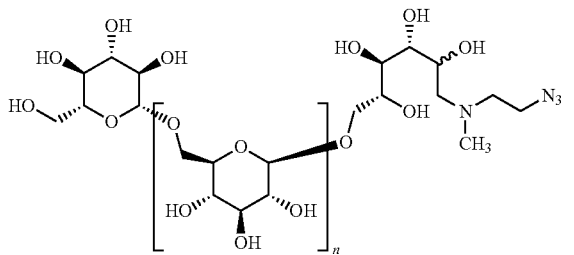

(formula 14)

14a. 4-mer (n=3), [(2R,3R,4R,5RS)-2,3,4,5-tetrahydroxy-6-(N-methyl-N-(2-azido ethyl))amino]hexyl [O-β-D-glucopyranosyl-1,6]₃-β-D-glucopyranoside: m/z=913 (M+H⁺), 930 (M+NH₄⁺), 935 (M+Na⁺);

14b. a 6-mer (n=5), [(2R,3R,4R,5RS)-2,3,4,5-tetrahydroxy-6-(N-methyl-N-(2-azidoethyl))amino]hexyl [O-β-D-glucopyranosyl-1,6]₅-β-D-glucopyranoside: m/z=1237 (M+H⁺), 1254 (M+NH₄⁺), 1259 (M+Na⁺);

14c. a 7-mer (n=6), [(2R,3R,4R,5RS)-2,3,4,5-tetrahydroxy-6-(N-methyl-N-(2-azido ethyl))amino]hexyl [O-β-D-glucopyranosyl-1,6]₆-β-D-glucopyranoside: m/z=1400 (M+H⁺), 1417 (M+NH₄⁺), 1422 (M+Na⁺)

14d. an 8-mer (n=7), [(2R,3R,4R,5RS)-2,3,4,5-tetrahydroxy-6-(N-methyl-N-(2-azidoethyl))amino]hexyl [O-β-D-glucopyranosyl-1,6]₇-β-D-glucopyranoside: m/z=1562 (M+H⁺), 1579 (M+NH₄⁺), 1584 (M+Na⁺); and 14e. a 9-mer (n=8), [(2R,3R,4R,5RS)-2,3,4,5-tetrahydroxy-6-(N-methyl-N-(2-azidoethyl))amino]hexyl [O-β-D-glucopyranosyl-1,6]₈-β-D-glucopyranoside: m/z=1724 (M+H⁺), 1741 (M+NH₄⁺), 1746 (M+Na⁺).

b. Compounds of Formula 15

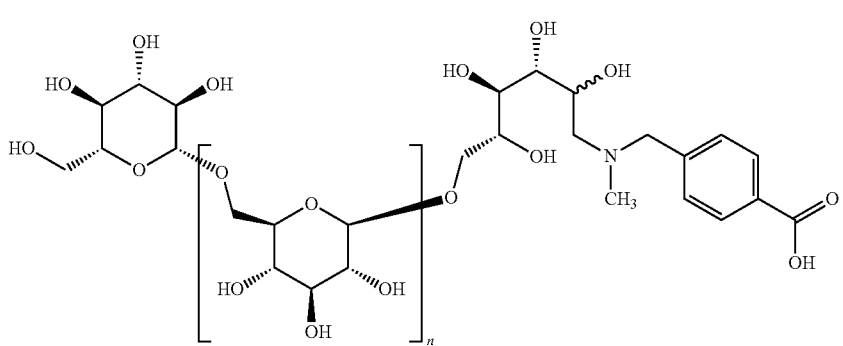

(formula 15)

15a. a 3-mer (n=2), N-[6-[O-β-D-glucopyranosyl-(1→6)]₃oxy-(2RS,3R,4R,5R)-2,3,4,5-tetrahydroxyhexyl)-4-N-(methyl)amino)methylbenzoic acid: m/z=816 (M+H⁺);

15b. a 4-mer (n=3), —N-[6-[O-β-D-glucopyranosyl-(1→6)]₄ oxy-(2RS,3R,4R,5R)-2,3,4,5-tetrahydroxyhexyl)-4-N-(methyl)amino)methylbenzoic acid: m/z=978 (M+H⁺);

15c. a 5-mer (n=4), 4-N-[6-[O-β-D-glucopyranosyl-(1→6)]₅ oxy-(2RS,3R,4R,5R)-2,3,4,5-tetrahydroxyhexyl)-4-N-(methyl)amino)methylbenzoic acid: m/z=1140 (M+H⁺);

15d. a 6-mer (n=5), 4-N-[6-[O-β-D-glucopyranosyl-(1→6)]₆ oxy-(2RS,3R,4R,5R)-2,3,4,5-tetrahydroxyhexyl)-4-N-(methyl)amino)methylbenzoic acid: m/z=1302 (M+H⁺);

15e. a 7-mer (n=6), 4-N-[6-[O-β-D-glucopyranosyl-(1→6)]₇ oxy-(2RS,3R,4R,5R)-2,3,4,5-tetrahydroxyhexyl)-4-N-(methyl)amino)methylbenzoic acid: m/z=1464 (M+H⁺);
and 15f. an 8-mer (n=7), 4-N-[6-[O-β-D-glucopyranosyl-(1→6)]₈oxy-(2RS,3R,4R,5R)-2,3,4,5-tetrahydroxyhexyl)-4-N-(methyl)amino)methylbenzoic acid: m/z=1626 (M+H⁺).

c. Compounds of Formula 16

16a. a 3-mer (n=2), [(2R,3R,4R,5RS)-2,3,4,5-tetrahydroxy-6-(N-methyl-N-(5-tert-butylpentylcarbamoyl))amino] hexyl [O-β-D-glucopyranosyl-1,6]₂-β-D-glucopyranoside: m/z=705 (M+H⁺);

16b. a 4-mer (n=3), [(2R,3R,4R,5RS)-2,3,4,5-tetrahydroxy-6-(N-methyl-N-(5-tert-butylpentylcarbamoyl))amino] hexyl [O-β-D-glucopyranosyl-1,6]₃-β-D-glucopyranoside: m/z=867 (M+H⁺);

16c. a 5-mer (n=4), [(2R,3R,4R,5RS)-2,3,4,5-tetrahydroxy-6-(N-methyl-N-(5-tert-butylpentylcarbamoyl))amino] hexyl [O-β-D-glucopyranosyl-1,6]₄-β-D-glucopyranoside: m/z=1029 (M+H⁺);

16d. a 6-mer (n=5), [(2R,3R,4R,5RS)-2,3,4,5-tetrahydroxy-6-(N-methyl-N-(5-tert-butylpentylcarbamoyl))amino] hexyl [O-β-D-glucopyranosyl-1,6]₅-β-D-glucopyranoside: m/z=1191 (M+H⁺); and 16e. a 7-mer (n=6), [(2R,3R,4R,5RS)-2,3,4,5-tetrahydroxy-6-(N-methyl-N-(5-tert-butylpentylcarbamoyl))amino] hexyl [O-β-D-glucopyranosyl-1,6]₆-β-D-glucopyranoside: m/z=1353 (M+H⁺).

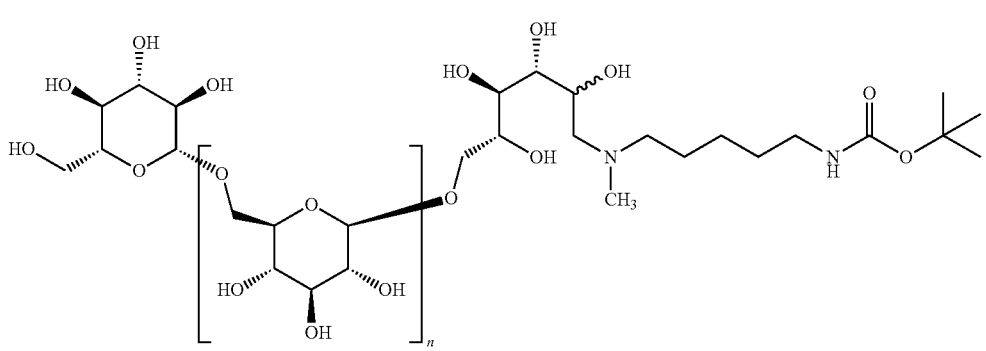

(formula 16)

Example 10

[(2R,3R,4R,5RS)-2,3,4,5-tetrahydroxy-6-(N-methyl-N-(2-carboxymethyl)amino]hexyl [O-β-D-glucopyranosyl-1,6]$_4$-β-D-glucopyranoside

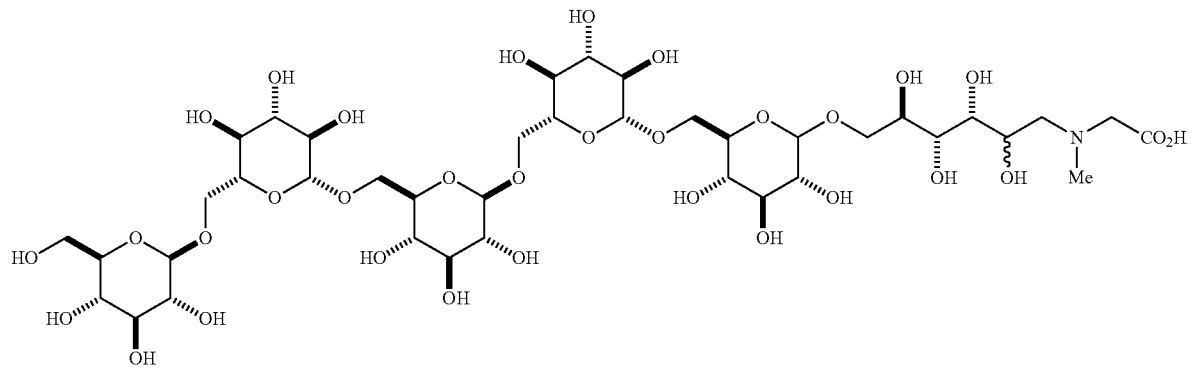

(formula 17)

A solution of 6-mer (10 mg, 10 μmol) in 100 mM sodium acetate buffer pH=4.0 (100 uL) was treated with sarcosine (2.7 mg, 30 μmole, 3 equiv) and then sodium cyanoborohydride (1.9 mg, 30 μmole, 3 equiv) and was then warmed to 40° C. After stirring for 24 h, LC/MS analysis showed clean conversion to the desired product. The reaction mixture was then cooled to room temperature and was desalted by passage through a centrifuge column of P2 (5 g, 6×300 uL) and the combined elute was freeze dried and was then further purified by HPLC purification on a HILIC column (4.6×250 mm, 80-35% acetonitrile/water w/ 0.1% ammonium hydroxide, λ=220 nm) to yield the desired product: m/z=1064 (M+H$^+$), 1081 (M+NH$_4^+$), 1086 (M+Na$^+$).

Similarly prepared by the method of this example were:
a. Compounds of Formula 18

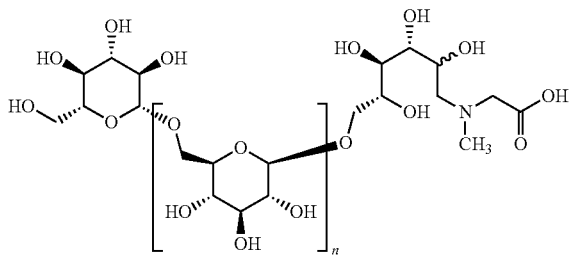

(formula 18)

18a. a 4-mer (n=3), [(2R,3R,4R,5RS)-2,3,4,5-tetrahydroxy-6-(N-methyl-N-(2-carboxymethyl)amino]hexyl [O-β-D-glucopyranosyl-1,6]$_3$-β-D-glucopyranoside: m/z=902 (M+H$^+$), 919 (M+NH$_4^+$), 924 (M+Na$^+$);

18b. a 6-mer (n=5), [(2R,3R,4R,5RS)-2,3,4,5-tetrahydroxy-6-(N-methyl-N-(2-carboxymethyl)amino]hexyl [O-β-D-glucopyranosyl-1,6]$_5$-β-D-glucopyranoside: m/z=1226 (M+H$^+$), 1243 (M+NH$_4^+$), 1248 (M+Na$^+$);

18c. a 7-mer (n=6), [(2R,3R,4R,5RS)-2,3,4,5-tetrahydroxy-6-(N-methyl-N-(2-carboxymethyl)amino]hexyl [O-β-D-glucopyranosyl-1,6]$_6$-β-D-glucopyranoside: m/z=1388 (M+H$^+$), 1405 (M+NH$_4^+$), 1410 (M+Na$^+$);

18d. an 8-mer (n=7), [(2R,3R,4R,5RS)-2,3,4,5-tetrahydroxy-6-(N-methyl-N-(2-carboxymethyl)amino]hexyl [O-β-D-glucopyranosyl-1,6]$_7$-β-D-glucopyranoside: m/z=1551 (M+H$^+$), 1568 (M+NH$_4^+$), 1573 (M+Na$^+$); and 18e. a 9-mer (n=8), [(2R,3R,4R,5RS)-2,3,4,5-tetrahydroxy-6-(N-methyl-N-(2-carboxymethyl)amino]hexyl [O-β-D-glucopyranosyl-1,6]$_8$-β-D-glucopyranoside: m/z=1713 (M+H$^+$), 1730 (M+NH$_4^+$), 1735 (M+Na$^+$).

b. Compounds of Formula 19

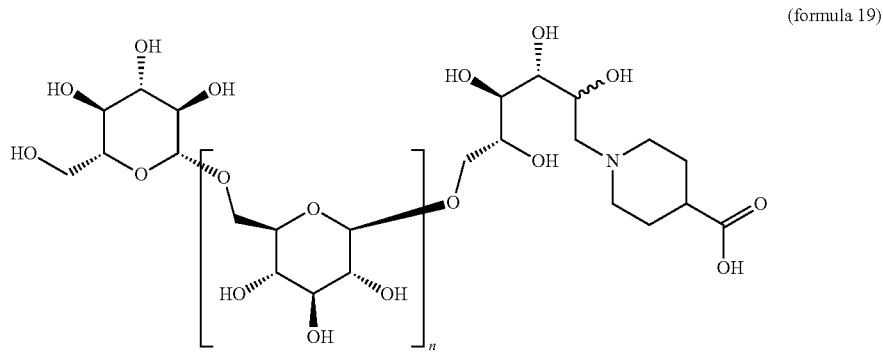
(formula 19)

19a. a 3-mer (n=2), N-[6-[(O-β-D-glucopyranosyl-(1,6))$_2$-β-D-glucopyranosyl](2RS,3R,4R,5R)-2,3,4,5-tetrahydroxyhexyl]piperidine-4-carboxylic acid: m/z=780 (M+H$^+$);

19b. a 4-mer (n=3), N-[6-[(O-(β-D-glucopyranosyl-(1,6))$_3$-β-D-glucopyranosyl](2RS,3R,4R,5R)-2,3,4,5-tetrahydroxyhexyl]piperidine-4-carboxylic acid: m/z=942 (M+H$^+$);

19c. a 5-mer (n=4), N-[6-[(O-(β-D-glucopyranosyl-(1,6))$_4$-β-D-glucopyranosyl](2RS,3R,4R,5R)-2,3,4,5-tetrahydroxyhexyl]piperidine-4-carboxylic acid: m/z=1104 (M+H$^+$);

19d. a 6-mer (n=5), N-[6-[(O-β-D-glucopyranosyl-(1,6))$_5$-β-D-glucopyranosyl](2RS,3R,4R,5R)-2,3,4,5-tetrahydroxyhexyl]piperidine-4-carboxylic acid: m/z=1266 (M+H$^+$);

19e. a 7-mer (n=6), N-[6-[(O-(β-D-glucopyranosyl-(1,6))$_6$-β-D-glucopyranosyl](2RS,3R,4R,5R)-2,3,4,5-tetrahydroxyhexyl]piperidine-4-carboxylic acid: m/z=1428 (M+H$^+$); and 19f. an 8-mer (n=7), N-[6-[(O-β-D-glucopyranosyl-(1,6))$_7$-β-D-glucopyranosyl](2RS,3R,4R,5R)-2,3,4,5-tetrahydroxyhexyl]piperidine-4-carboxylic acid: m/z=1590 (M+H$^+$).

c. Compounds of Formula 20

20a. a 3-mer (n=2), N-[6-[(O-(β-D-glucopyranosyl-(1,6))$_2$-β-D-glucopyranosyl](2RS,3R,4R,5R)-2,3,4,5-tetrahydroxyhexyl]piperidine-4-carboxylic acid: m/z=794 (M+H$^+$);

20b. a 4-mer (n=3), N-[6-[(O-(β-D-glucopyranosyl-(1,6))$_3$-β-D-glucopyranosyl](2RS,3R,4R,5R)-2,3,4,5-tetrahydroxyhexyl]-4-piperidylacetic acid: m/z=956 (M+H$^+$);

20c. a 5-mer (n=4), N-[6-[(O-(β-D-glucopyranosyl-(1,6))$_4$-β-D-glucopyranosyl](2RS,3R,4R,5R)-2,3,4,5-tetrahydroxyhexyl]-4-piperidylacetic acid: m/z=1118 (M+H$^+$);

20d. a 6-mer (n=5), N-[6-[(O-(β-D-glucopyranosyl-(1,6))$_5$-β-D-glucopyranosyl](2RS,3R,4R,5R)-2,3,4,5-tetrahydroxyhexyl]-4-piperidylacetic acid: m/z=1280 (M+H$^+$);

20e. a 7-mer (n=6), N-[6-[(O-(β-D-glucopyranosyl-(1,6))$_6$-β-D-glucopyranosyl](2RS,3R,4R,5R)-2,3,4,5-tetrahydroxyhexyl]-4-piperidylacetic acid: m/z=1442 (M+H$^+$); and 20f. an 8-mer (n=7), N-[6-[(O-(β-D-glucopyranosyl-(1,6))$_7$-β-D-glucopyranosyl](2RS,3R,4R,5R)-2,3,4,5-tetrahydroxyhexyl]-4-piperidylacetic acid: m/z=1604 (M+H$^+$).

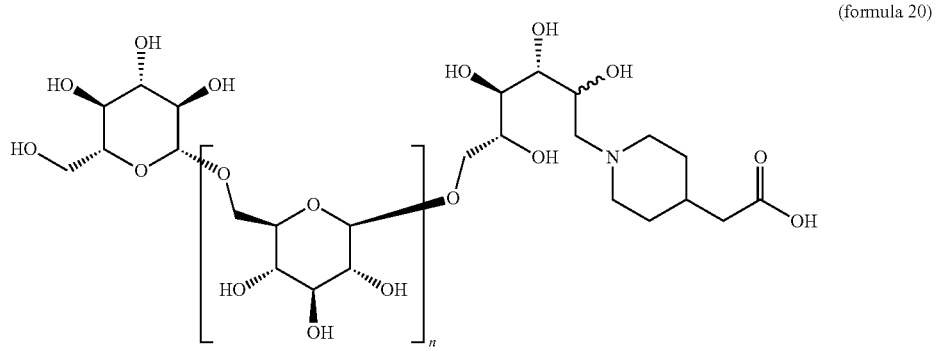
(formula 20)

d. Compounds of Formula 21

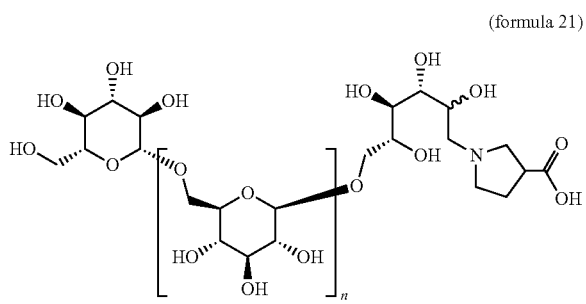

(formula 21)

21a. a 3-mer (n=2), N-[6-[(O-(β-D-glucopyranosyl-1,6)$_2$-β-D-glucopyranosyl](2RS,3R,4R,5R)-2,3,4,5-tetrahydroxyhexyl]pyrrolidine-3-carboxylic acid: m/z=766 (M+H$^+$);
21b. a 4-mer (n=3), N-[6-[(O-(β-D-glucopyranosyl-1,6)$_3$-β-D-glucopyranosyl](2RS,3R,4R,5R)-2,3,4,5-tetrahydroxyhexyl]pyrrolidine-3-carboxylic acid: m/z=928 (M+H$^+$);
21c. a 5-mer (n=4), N-[6-[(O-(β-D-glucopyranosyl-(1,6))$_4$-β-D-glucopyranosyl](2RS,3R,4R,5R)-2,3,4,5-tetrahydroxyhexyl]pyrrolidine-3-carboxylic acid: m/z=1090 (M+H$^+$);
21d. a 6-mer (n=5), N-[6-[(O-(β-D-glucopyranosyl-(1,6))$_5$-β-D-glucopyranosyl](2RS,3R,4R,5R)-2,3,4,5-tetrahydroxyhexyl]pyrrolidine-3-carboxylic acid: m/z=1252 (M+H$^+$);
21e. a 7-mer (n=6), N-[6-[(O-(β-D-glucopyranosyl-(1,6))$_6$-β-D-glucopyranosyl](2RS,3R,4R,5R)-2,3,4,5-tetrahydroxyhexyl]pyrrolidine-3-carboxylic acid: m/z=1414 (M+H$^+$); and
21f. an 8-mer (n=7), N-[6-[(O-(β-D-glucopyranosyl-(1,6))$_7$-β-D-glucopyranosyl](2RS,3R,4R,5R)-2,3,4,5-tetrahydroxyhexyl]pyrrolidine-3-carboxylic acid: m/z=1576 (M+H$^+$).

Example 11

Per-acetylation of a Mixture of β-1,6-D-glucan Oligosaccharides

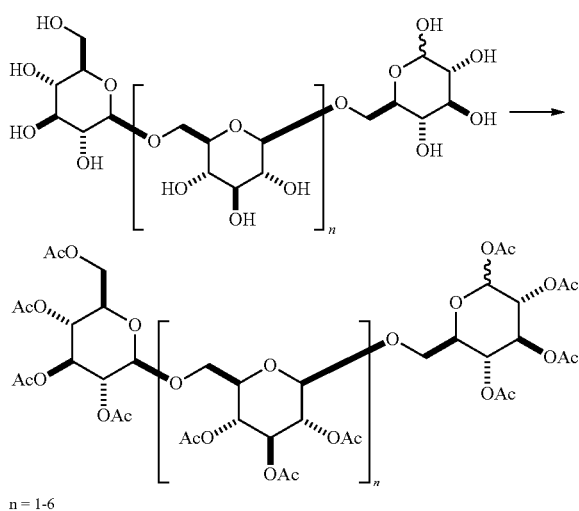

n = 1-6

Into a microwave reaction vial was placed a mixture of β-1,6-D-glucan oligosaccharides (177 mg, grey powder, size range ~3-8). To this was added acetic anhydride (1.0 mL, 10.6 mmol) and sodium acetate (97 mg, 1.2 mmol). The mixture was treated to microwave irradiation (CEM Discover) at 125° C. (200 W) for the following time cycles: 10 min, 4×5 min. Additional portions of acetic anhydride (500 µL) and sodium acetate (2×50 mg) were added after cycles 1 and 3, and 4 and 5, respectively. Analysis by LC/MS was conducted on an aliquot of the reaction mixture after each cycle to assay the extent of acetylation. Additional cycles of microwave irradiation were applied, as necessary, until full conversion was achieved, as indicated by LC/MS.

At the end of the reaction, the mixture was filtered off on a Hirsch funnel, solids rinsed with ethyl acetate, and the filtrate concentrated in vacuo to yield a brown oil. The oil was taken up in ethyl acetate (20 mL) followed by washing with water and brine (10 and 5 mL, resp.), was dried (MgSO$_4$), was filtered and was concentrated in vacuo to give the crude product as a light brown foam. Purification by RP-LC (ProStar/Dynamax, Hypersil 5 µ, 10 mm×50 mm, ACN/H$_2$O+0.1% formic acid, 5→95% B, 30 minutes) yielded the individual per-acetylated oligosaccharides:

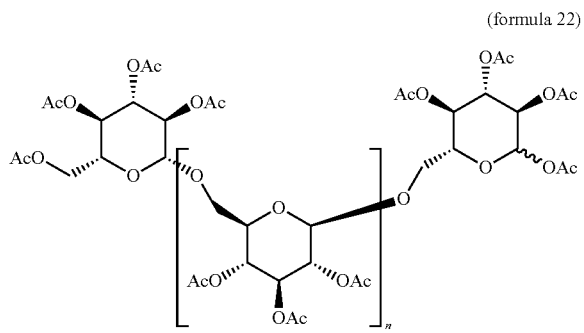

(formula 22)

22a. a 4-mer (n=2): O-2,3,4,6-tetra-O-acetyl-D-glucopyranosyl-1,6-O-2,3,4-tri-O-acetyl-D-glucopyranosyl-1,6-O-2,3,4-tri-O-acetyl-D-glucopyranosyl-1,6-D-glucopyranose tetraacetate, m/z=1272 (M+NH$_4^+$);
22b. a 5-mer (n=3): O-2,3,4,6-tetra-O-acetyl-D-glucopyranosyl-1,6-O-2,3,4-tri-O-acetyl-D-glucopyranosyl-1,6-O-2,3,4-tri-O-acetyl-D-glucopyranosyl-1,6-O-2,3,4-tri-O-acetyl-D-glucopyranosyl-1,6-D-glucopyranose tetraacetate, m/z=1560 (M+NH$_4^+$);
22c. a 6-mer (n=4): O-2,3,4,6-tetra-O-acetyl-D-glucopyranosyl-1,6-O-2,3,4-tri-O-acetyl-D-glucopyranosyl-1,6-O-2,3,4-tri-O-acetyl-D-glucopyranosyl-1,6-O-2,3,4-tri-O-acetyl-D-glucopyranosyl-1,6-O-2,3,4-tri-O-acetyl-D-glucopyranosyl-1,6-D-glucopyranose tetraacetate, m/z=1848 (M+NH$_4^+$);
22d. a 7-mer (n=5): O-2,3,4,6-tetra-O-acetyl-D-glucopyranosyl-1,6-O-2,3,4-tri-O-acetyl-D-glucopyranosyl-1,6-O-2,3,4-tri-O-acetyl-D-glucopyranosyl-1,6-O-2,3,4-tri-O-acetyl-D-glucopyranosyl-1,6-O-2,3,4-tri-O-acetyl-D-glucopyranosyl-1,6-O-2,3,4-tri-O-acetyl-D-glucopyranosyl-1,6-D-glucopyranose tetraacetate, m/z=2136 (M+NH$_4^+$);
22e. an 8-mer (n=6): O-2,3,4,6-tetra-O-acetyl-D-glucopyranosyl-1,6-O-2,3,4-tri-O-acetyl-D-glucopyranosyl-1,6-O-2,3,4-tri-O-acetyl-D-glucopyranosyl-1,6-O-2,3,4-tri-O-acetyl-D-glucopyranosyl-1,6-O-2,3,4-tri-O-acetyl-D-glucopyranosyl-1,6-O-2,3,4-tri-O-acetyl-D-glucopyranosyl-1,6-O-2,3,4-tri-O-acetyl-D- glucopyranosyl-1,6-O-2,3,4-tri-O-acetyl-D-glucopyranosyl-1,6-D-glucopyranose tetraacetate, m/z=2424 (M+NH$_4^+$);

22f. a 9-mer (n=7): O-2,3,4,6-tetra-O-acetyl-D-glucopyranosyl-1,6-O-2,3,4-tri-O-acetyl-D-glucopyranosyl-1,6-O-2,3,4-tri-O-acetyl-D-glucopyranosyl-1,6-O-2,3,4-tri-O-acetyl-D-glucopyranosyl-1,6-O-2,3,4-tri-O-acetyl-D-glucopyranosyl-1,6-O-2,3,4-tri-O-acetyl-D-glucopyranosyl-1,6-O-2,3,4-tri-O-acetyl-D-glucopyranosyl-1,6-O-2,3,4-tri-O-acetyl-D-glucopyranosyl-1,6-D-glucopyranose tetraacetate, m/z=2712 (M+NH$_4^+$);

22g. a 10-mer (n=8): O-2,3,4,6-tetra-O-acetyl-D-glucopyranosyl-1,6-O-2,3,4-tri-O-acetyl-D-glucopyranosyl-1,6-O-2,3,4-tri-O-acetyl-D-glucopyranosyl-1,6-O-2,3,4-tri-O-acetyl-D-glucopyranosyl-1,6-O-2,3,4-tri-O-acetyl-D-glucopyranosyl-1,6-O-2,3,4-tri-O-acetyl-D-glucopyranosyl-1,6-O-2,3,4-tri-O-acetyl-D-glucopyranosyl-1,6-O-2,3,4-tri-O-acetyl-D-glucopyranosyl-1,6-O-2,3,4-tri-O-acetyl-D-glucopyranosyl-1,6-D-glucopyranose tetraacetate, m/z=3001 (M+NH$_4^+$);

22h. an 11-mer (n=9): O-2,3,4,6-tetra-O-acetyl-D-glucopyranosyl-1,6-O-2,3,4-tri-O-acetyl-D-glucopyranosyl-1,6-O-2,3,4-tri-O-acetyl-D-glucopyranosyl-1,6-O-2,3,4-tri-O-acetyl-D-glucopyranosyl-1,6-O-2,3,4-tri-O-acetyl-D-glucopyranosyl-1,6-O-2,3,4-tri-O-acetyl-D-glucopyranosyl-1,6-O-2,3,4-tri-O-acetyl-D-glucopyranosyl-1,6-O-2,3,4-tri-O-acetyl-D-glucopyranosyl-1,6-O-2,3,4-tri-O-acetyl-D-glucopyranosyl-1,6-O-2,3,4-tri-O-acetyl-D-glucopyranosyl-1,6-D-glucopyranose tetraacetate, m/z=3288 (M+NH$_4^+$);

22i. a 12-mer (n=10): O-2,3,4,6-tetra-O-acetyl-D-glucopyranosyl-1,6-O-2,3,4-tri-O-acetyl-D-glucopyranosyl-1,6-O-2,3,4-tri-O-acetyl-D-glucopyranosyl-1,6-O-2,3,4-tri-O-acetyl-D-glucopyranosyl-1,6-O-2,3,4-tri-O-acetyl-D-glucopyranosyl-1,6-O-2,3,4-tri-O-acetyl-D-glucopyranosyl-1,6-O-2,3,4-tri-O-acetyl-D-glucopyranosyl-1,6-O-2,3,4-tri-O-acetyl-D-glucopyranosyl-1,6-O-2,3,4-tri-O-acetyl-D-glucopyranosyl-1,6-O-2,3,4-tri-O-acetyl-D-glucopyranosyl-1,6-O-2,3,4-tri-O-acetyl-D-glucopyranosyl-1,6-D-glucopyranose tetraacetate, m/z=3577 (M+NH$_4^+$).

Example 12

2-Chloroethyl O-2,3,4,6-tetra-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-β-D-glucopyranose 2,3,4-triacetate (formula 23)

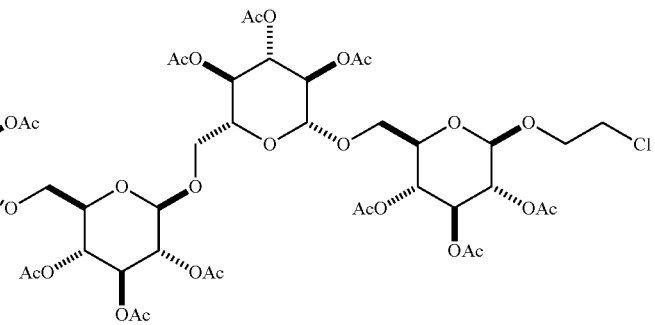

A solution of the 6-mer per-acetate (29 mg, 0.016 mmol) from Example 11 and 2-chloroethanol (2.1 μL, 0.032 mmol, 2.0 equiv) in anhydrous toluene (158 μL) was heated at 45° C. for 5 min. Iron trichloride (2.6 mg, 0.016 mmol, 1.0 equiv) was then added at room temperature, and the resultant mixture was heated at 45° C. for 2.25 h. The mixture was diluted with ethyl acetate, was washed with water and brine, was dried (MgSO$_4$), filtered and concentrated in vacuo to provide 38 mg of the crude product as a brown paste. LC-MS: 9.1 min, m/z 1869 [M+NH$_4^+$].

Similarly prepared by the method of this example were:

23a. a 4-mer: 2-chloroethyl O-2,3,4,6-tetra-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-β-D-glucopyranose 2,3,4-triacetate; m/z=1293 (M+NH$_4^+$);

23b. a 5-mer: 2-chloroethyl O-2,3,4,6-tetra-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-β-D-glucopyranose 2,3,4-triacetate; m/z=1581 (M+NH$_4^+$); and 23c. a 7-mer: 2-chloroethyl O-2,3,4,6-tetra-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-β-D-glucopyranose 2,3,4-triacetate; m/z=2157 (M+NH$_4^+$).

Similarly prepared by the method of this example are:

23d. an 8-mer: 2-chloroethyl O-2,3,4,6-tetra-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-β-D-glucopyranose 2,3,4-triacetate; theoretical m/z=2445;

23e. a 9-mer: 2-chloroethyl O-2,3,4,6-tetra-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-β-D-glucopyranose 2,3,4-triacetate; theoretical m/z=2733;

23f. a 10-mer: 2-chloroethyl O-2,3,4,6-tetra-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-β-D-glucopyranose 2,3,4-triacetate; theoretical m/z=3022;

23g. an 11-mer: 2-chloroethyl O-2,3,4,6-tetra-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-β-D-glucopyranose 2,3,4-triacetate; theoretical m/z=3310; and 23h. A 12-mer: 2-chloroethyl O-2,3,4,6-tetra-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-β-D-glucopyranose 2,3,4-triacetate; theoretical m/z=3598.

Compounds according to formula 24 can also be prepared.

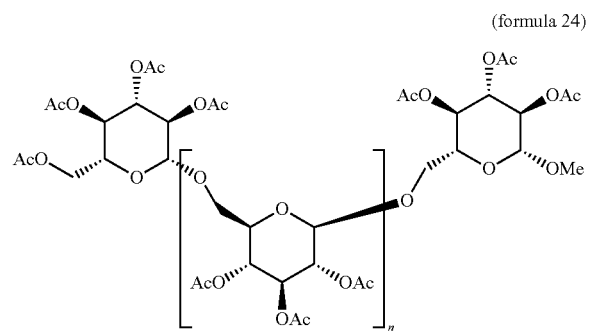

(formula 24)

24a. a 4-mer (n=2): methyl O-2,3,4,6-tetra-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-β-D-glucopyranose 2,3,4-triacetate; theoretical m/z=1227 (M+H$^+$);

24b. a 5-mer (n=3): methyl O-2,3,4,6-tetra-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-β-D-glucopyranose 2,3,4-triacetate; theoretical m/z=1515 (M+H$^+$);

24c. a 6-mer (n=4): methyl O-2,3,4,6-tetra-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-β-D-glucopyranose 2,3,4-triacetate; theoretical m/z=1803 (M+H$^+$);

24d. a 7-mer (n=5): methyl O-2,3,4,6-tetra-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-β-D-glucopyranose 2,3,4-triacetate; theoretical m/z=2091 (M+H$^+$);

24e. an 8-mer (n=6): methyl O-2,3,4,6-tetra-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-β-D-glucopyranose 2,3,4-triacetate; theoretical m/z=2379 (M+H$^+$);

24f. a 9-mer (n=7): methyl O-2,3,4,6-tetra-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-β-D-glucopyranose 2,3,4-triacetate; theoretical m/z=2667 (M+H$^+$);

24g. a 10-mer (n=8): methyl O-2,3,4,6-tetra-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-β-D-glucopyranose 2,3,4-triacetate; theoretical m/z=2955 (M+H$^+$);

24h. an 11-mer (n=9): methyl O-2,3,4,6-tetra-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-β-D-glucopyranose 2,3,4-triacetate; theoretical m/z=3243 (M+H$^+$); and 24i. a 12-mer (n=10): methyl O-2,3,4,6-tetra-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D- glucopyranosyl-β-1,6-β-D-glucopyranose 2,3,4-triacetate; theoretical m/z=3531 (M+H⁺).

Example 13

2-Azidooethyl O-2,3,4,6-tetra-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-β-D-glucopyranose tetraacetate

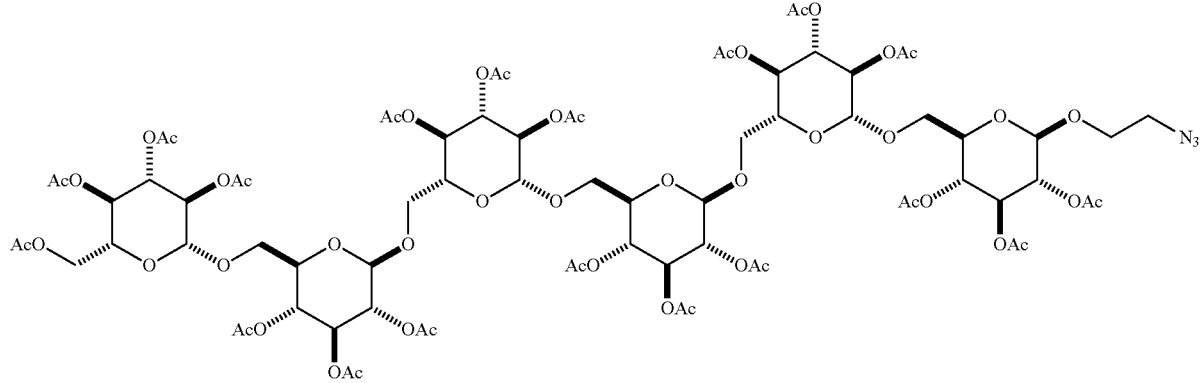

(formula 25)

To a solution of the 6-mer 2-chloroethyl compound from Example 12 (29.6 mg, 0.016 mmol) in anhydrous DMF (158 µL) was added sodium azide (5.2 mg, 0.080 mmol, 5.0 equiv) and tetra-n-butyl ammonium iodide (5.9 mg, 0.016 mmol, 1.0 equiv). The resultant mixture was heated at 80° C. for 16 hours after which the volatiles were removed in vacuo. The remaining oily residue was taken up in ethyl acetate and washed with water and brine, then dried over MgSO₄, filtered and solvent removed under reduced pressure to provide 23.2 mg (78% theoretical mass recovery) of the azide as a tan solid. LC/MS: $R_t$=8.29 min, m/z 1891 [M+NH₄⁺].

Similarly prepared by the method of this example were:
25a. a 4-mer: 2-azidoethyl O-2,3,4,6-tetra-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-β-D-glucopyranose 2,3,4-triacetate; m/z=1315 (M+NH₄⁺);
25b. a 5-mer: 2-azidoethyl O-2,3,4,6-tetra-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-β-D-glucopyranose 2,3,4-triacetate; m/z=1603 (M+NH₄⁺); and
25c. a 7-mer: 2-azidoethyl O-2,3,4,6-tetra-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-β-D-glucopyranose 2,3,4-triacetate; m/z=2179 (M+NH₄⁺).

Similarly prepared by the method of this example are:
25d. an 8-mer: 2-azidoethyl O-2,3,4,6-tetra-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-β-D-glucopyranose 2,3,4-triacetate; theoretical m/z=2467 (M+NH₄⁺);
25e. a 9-mer: 2-azidoethyl O-2,3,4,6-tetra-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-β-D-glucopyranose 2,3,4-triacetate; theoretical m/z=2755 (M+NH₄⁺);
25f. a 10-mer: 2-azidoethyl O-2,3,4,6-tetra-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-β-D-glucopyranose 2,3,4-triacetate; theoretical m/z=3044 (M+NH₄⁺);
25g. an 11-mer: 2-azidoethyl O-2,3,4,6-tetra-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-β-D-glucopyranose 2,3,4-triacetate; theoretical m/z=3332 (M+NH₄⁺); and
25h. a 12-mer: 2-azidoethyl O-2,3,4,6-tetra-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-β-D-glucopyranose 2,3,4-triacetate; theoretical m/z=3620 (M+NH₄⁺).

Example 14

2-Azidoethyl [O-β-D-glucopyranosyl-1,6]₅-β-D-glucopyranoside

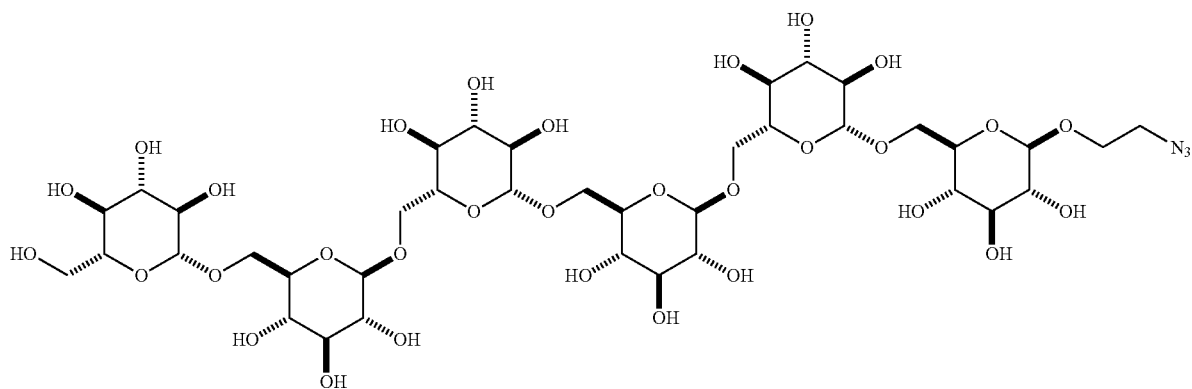

(formula 26)

To a solution of the 6-mer 2-chloroethyl compound from Example 13 (29.6 mg, 0.016 mmol) in anhydrous DMF (158 μL) was added sodium azide (5.2 mg, 0.080 mmol, 5.0 equiv) and tetra-n-butyl ammonium iodide (5.9 mg, 0.016 mmol, 1.0 equiv). The resultant mixture was heated at 80° C. for 16 hours after which the volatiles were removed in vacuo. The remaining oily residue was taken up in ethyl acetate and washed with water and brine, then dried over MgSO₄, filtered and solvent removed under reduced pressure to provide 23.2 mg (78% theoretical mass recovery) of the azide as a tan solid. LC/MS: $R_f$=8.29 min, m/z 1875 [M+NH₄⁺].

The product of Example 14 (23.2 mg) is dissolved in a mixture of methanol (4 ml) and DCM (1 mL). A solution of sodium methoxide in methanol (0.2 mL of 25% wt/v solution) is added and the mixture is stirred at RT overnight. The mixture is neutralized with acid resin (Dowex 50) and the resin is removed by filtration. The filtrate is concentrated in vacuo and the crude product is purified by silica gel chromatography using HPLC grade water/IPA (1:9) to obtain the title compound as an off-white solid: m/z=1077 (M+NH₄⁺).

Similarly prepared by the method of this example were:

26a. a 4-mer: 2-azidoethyl [O-β-D-glucopyranosyl-1,6]₃-β-D-glucopyranoside, m/z=753 (M+NH₄⁺);

26b. a 5-mer: 2-azidoethyl [O-β-D-glucopyranosyl-1,6]₄-β-D-glucopyranoside, m/z=915 (M+NH₄⁺); and 26c. a 7-mer: 2-azidoethyl [O-β-D-glucopyranosyl-1,6]₆-β-D-glucopyranoside, m/z=1239 (M+NH₄⁺).

Similarly prepared by the method of this example are:

26d. an 8-mer: 2-azidoethyl [O-β-D-glucopyranosyl-1,6]₇-β-D-glucopyranoside, theoretical m/z=1401 (M+NH₄⁺);

26e. a 9-mer: 2-azidoethyl [O-β-D-glucopyranosyl-1,6]₈-β-D-glucopyranoside, theoretical m/z=1563 (M+NH₄⁺);

26f. a 10-mer: 2-azidoethyl [O-β-D-glucopyranosyl-1,6]₉-β-D-glucopyranoside, theoretical m/z=1726 (M+NH₄⁺);

26g. an 11-mer: 2-azidoethyl [O-β-D-glucopyranosyl-1,6]₁₀-β-D-glucopyranoside, theoretical m/z=1888 (M+NH₄⁺); and 26h. a 12 mer: 2-azidoethyl [O-β-D-glucopyranosyl-1,6]₁₁-β-D-glucopyranoside, theoretical m/z=2050 (M+NH₄⁺).

Example 15

[(2R,3R,4R,5RS)-2,3,4,5-tetrahydroxy-6-(N-methyl-N-(2-carboxymethyloxy)amino]hexyl [O-β-D-glucopyranosyl-1,6]₅-β-D-glucopyranoside

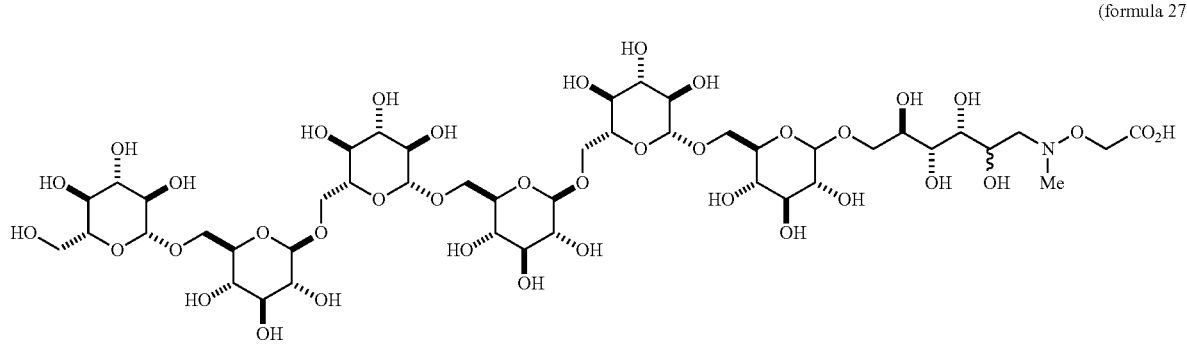

(formula 27)

A solution of [O-β-D-glucopyranosyl-1,6]$_6$-D-glucopyranoside (23 mg, 20 µmole) in 100 mM sodium acetate buffer pH=4.0 (150 µL) is treated with 2-aminooxyacetic acid HCl (7.7 mg, 60 µmole, 3 equiv) and then sodium cyanoborohydride (7.3 mg, 120 µmole, 6 equiv) and then is warmed to 40° C. After stirring for 24 h, the reaction mixture is cooled to room temperature and then subjected to 37% aqueous formaldehyde (13 µL, 200 µmole, 10 equiv.) and then additional sodium cyanoborohydride (12.2 mg, 200 µmole, 10 equiv). After stirring for 3 h, the mixture is desalted by passage through a centrifuge column of P2 (5 g, 6×300 uL) and the combined eluate is freeze dried and then further purified by HPLC purification on a HILIC column (4.6×250 mm, 80-35% acetonitrile/water w/ 0.1% ammonium hydroxide, λ=220 nm) to yield the desired product: m/z=1242 (M+H$^+$).

Example 16

6-O-[2,3,4-tri-O-benzoyl-6-O-[tert-butyldiphenylsilyl]-D-glucopyranosyl-β-D-glucopyranose 2,3,4-tribenzoate 1-(2,2,2-trichloroethanimidate)

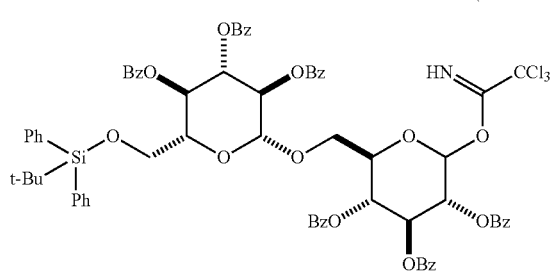

(formula 28)

To a stirred solution of amygdalin (10 g, 0.022 mol) in anhydrous DMF (100 mL) was added imidazole (3.27 g, 0.048 mol) followed by t-butyldiphenylchlorosilane (6.25 mL, 0.024 mol) at RT. The reaction mixture was stirred at RT. Monitoring by TLC showed the reaction to be complete after 18 h. The reaction was poured on ice water and was extracted with DCM (5×100 mL). The combined extract was dried over sodium sulfate, was decanted and was concentrated in vacuo to give 13.5 g of a thick, brown syrup, which was used in the next step without further purification (TLC: Rf ca. 0.6. DCM:MeOH (5:1)).

To a solution of this product in dry pyridine (60 mL) was added benzoyl chloride (15.8 mL, 0.136 mol), and this mixture was stirred at RT for one day. The reaction mixture was poured into water (500 mL) and was extracted with ethyl acetate (2×50 mL). The combined extract was washed with 1N HCl (2×100 mL), saturated sodium bicarbonate solution (2×50 mL), and brine solution (50 mL). The crude product was purified by silica gel column chromatography using (7:3) hexanes:ethyl acetate to give 13.2 g of product: Rf=0.65 (hexanes:ethyl acetate=7:3).

A portion of this product (9.0 g, 6.8 mmol) was dissolved in acetone (100 mL) and to this solution was added ammonium formate (2.15 g 34.1 mmol) followed by 10% palladium on carbon (9 g). The resulting suspension was heated at reflux for 24 h. The reaction mixture was cooled to RT and was filtered through a plug of celite. The filtrate was concentrated in vacuo to a crude residue, which was purified by chromatography on a silica gel column using 7:3 hexanes:ethyl acetate giving 6.0 g of a glossy solid: Rf=0.5 (7:3 hexanes:ethyl acetate).

A portion of this product (2.0 g, 1.7 mmol) was dissolved in DCM (20 mL) and to this solution was added CCl$_3$CN (0.34 mL, 3.3 mmol) followed by sodium hydride (4 mg, 0.17 mmol). This mixture was stirred at RT for 1 h and was quenched by pouring onto ice water. The organic layer was separated, was dried over sodium sulfate, was decanted and was concentrated in vacuo to obtain 1.2 g of the title compound as a white foam: Rf=0.5 (hexanes:ethyl acetate=8:2).

Example 17

2-Azidoethyl 6-O-[2,3,4-tri-O-benzoyl]-D-glucopranosyl-β-D-glucopyranose 2,3,4-tribenzoate

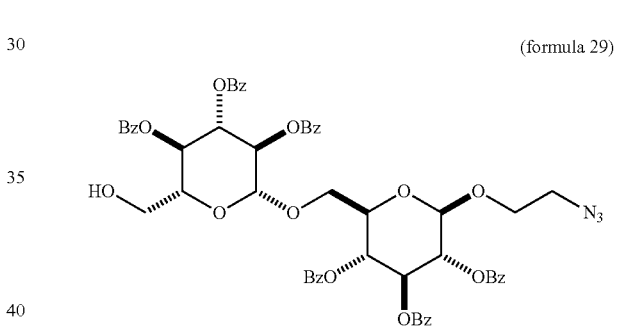

(formula 29)

To a stirred solution of the product Example 16 (2.5 g, 1.9 mmol) and 2-azidoethanol (485 mg, 5.56 mmol) in anhydrous DCM (50 mL) was added TMSOTf (0.55 mmol) at 0° C. After stirring at 0° C. for 30 min the temperature was raised slowly to RT and stirring was continued for 1 h. To this mixture was added saturated sodium bicarbonate solution (20 mL) and the organic layer was separated, was dried over sodium sulfate, was decanted and was concentrated in vacuo.

The crude product was purified by silica gel chromatography to give 1.7 g of a foamy solid: Rf=0.5 (hexanes:ethyl acetate=7:3. A portion of this compound (600 mg, 0.47 mmol) was dissolved in THF (20 mL) and HF-TEA (1.5 mL, 9.4 mmol) was added. The mixture was stirred at RT for 4 days at which time the THF was removed under reduced pressure. The residue was dissolved in ethyl acetate (50 mL) and was washed with saturated sodium bicarbonate solution. After drying over sodium sulfate, decantation and concentration in vacuo there was obtained a crude product. This was purified by silica gel column chromatography to give 450 mg of the title compound: Rf=0.3 (hexanes:ethyl acetate=6:4).

Example 18

2-Azidoethyl [O-β-D-glucopyranosyl-1,6]₃-D-glucopyranoside 2,2',2'',2''',3,3',3'',3''',4,4',4'',4'''-duodeca-O-benzoate

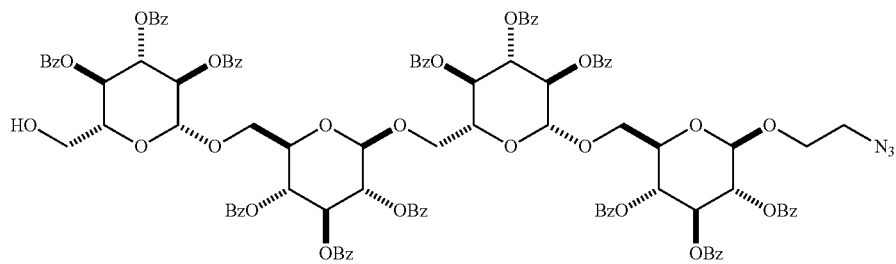

(formula 30)

A mixture of the product from Example 16 (2.38 g, 1.76 mmol) and that from Example 17 (610 mg, 0.59 mmol) was co-evaporated with toluene (2×10 mL) and kept under high vacuum for 1 h. This mixture was dissolved in DCM (20 mL) and was cooled to 0° C. TMSOTf (0.02 mL, 0.12 mmol) was added and stirring was continued for 30 min. The reaction mixture was poured onto saturated sodium bicarbonate solution (20 mL) and the organic layer was separated and was dried over sodium sulfate. A crude product was obtained after filtration and concentration in vacuo. This was purified by silica gel column chromatography to get 450 mg of a glossy syrup: Rf=0.4 (hexanes:ethyl acetate=6:4).

To a solution of this material (450 mg, 0.202 mmol) in tetrahydrofuran (8 mL) was added HF-Et₃N (0.66 mL, 4.05 mmol). This mixture was stirred at RT for 3 h, and then was mixed with cold saturated sodium bicarbonate solution (20 mL). This mixture was extracted with ethyl acetate (2×20 mL). The combined extract was dried over sodium sulfate, was filtered and was concentrated in vacuo. Purification by silica gel column chromatography using hexanes:ethyl acetate (1:1) gave 321 mg of the title compound: Rf=0.2 (ethyl acetate:hexanes=1:1)

Example 19

2-Azido ethyl [O-β-D-glucopyranosyl-1,6]₃-β-D-glucopyranoside

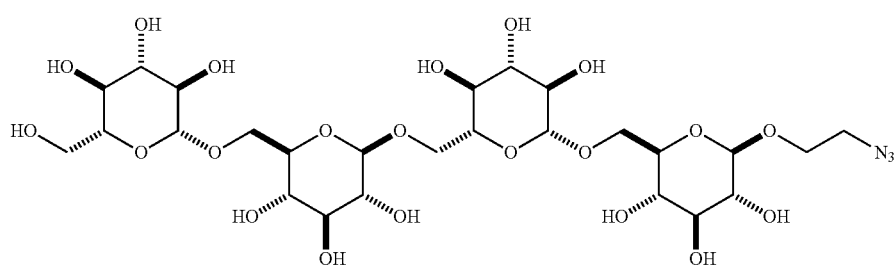

(formula 31)

The product of Example 18 (400 mg, 0.2 mmol) was dissolved in a mixture of methanol (8 ml) and DCM (2 mL). A solution of sodium methoxide in methanol (0.5 mL of 25% wt/v solution) was added and the mixture was stirred at RT overnight. The mixture was neutralized with acid resin (Dowex 50) and the resin was removed by filtration. The filtrate was concentrated in vacuo and the crude product was purified by silica gel chromatography using HPLC grade water/IPA (1:9) to obtain 103 mg of the title compound as an off-white solid: Rf=0.65 (water:IPA=1:9); $^{13}$C NMR (DMSO-d6) δ ppm=103.3, 103.2, 102.9, 76.8, 76.7, 76.6, 76.5, 75.6, 75.5, 73.5, 73.4, 73.3, 70.0, 69.8, 69.7, 68.7, 68.4, 67.6, 61.0, 50.4; m/z=736 (M+H⁺), 758 (M+Na⁺).

Example 20

6-O-[2,3,4-tri-O-benzoyl-6-O-[triethylsilyl]-D-glucopyranosyl-β-D-glucopyranose 2,3,4-tribenzoate 1-(2,2,2-trichloroethanimidate)

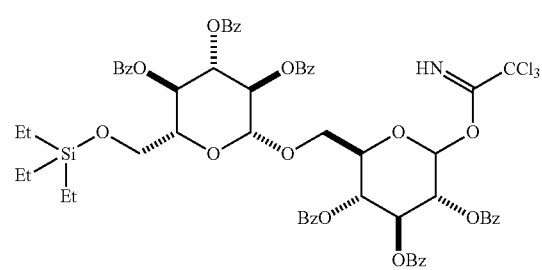

(formula 32)

To a stirred solution of amygdalin (10 g, 0.022 mol) in anhydrous DMF (100 mL) was added imidazole (3.27 g, 0.048 mol) followed by t-butyldiphenylchlorosilane (6.25 mL, 0.024 mol) at RT. The reaction mixture was stirred at RT. Monitoring by TLC showed the reaction to be complete after 18 h. The reaction was poured on ice water and was extracted with DCM (5×100 mL). The combined extract was dried over sodium sulfate, was decanted and was concentrated in vacuo to give 13.5 g of a thick, brown syrup, which was used in the next step without further purification (TLC: Rf ca. 0.6. DCM:MeOH (5:1)).

To a solution of this product in dry pyridine (60 mL) was added benzoyl chloride (15.8 mL, 0.136 mol), and this mixture was stirred at RT for one day. The reaction mixture was poured into water (500 mL) and was extracted with ethyl acetate (2×50 mL). The combined extract was washed with 1N HCl (2×100 mL), saturated sodium bicarbonate solution (2×50 mL), and brine solution (50 mL). The crude product was purified by silica gel column chromatography using (7:3) hexanes:ethyl acetate to give 13.2 g of product: Rf=0.65 (hexanes:ethyl acetate=7:3). A portion of this material was used in the next step.

To a stirred solution of this compound (450 mg, 0.34 mmol) in tetrahydrofuran (8 mL0 was added HF-Et₃N (0.66 mL, 4.1 mmol) and the mixture was stirred at RT for 3 h. The mixture was poured onto ice cold saturated NaHCO₃ solution (20 mL) and this mixture was extracted with ethyl acetate (2×20 mL). The combined extract was dried over sodium sulfate, was filtered and was concentrated in vacuo. This crude product was dissolved in anhydrous pyridine (10 mL) and triethylchlorosilane (62 mg, 0.41 mmol) and catalytic 4-dimethylaminopyridine was added. The resulting solution was stirred at RT overnight. The solvent was removed under reduced pressure and the crude product was dissolved in ethyl acetate and was washed with water and brine. The organic layer was dried over sodium sulfate, was filtered and was concentrated under reduced pressure. This material was purified by silica gel column chromatography using ethyl acetate:hexanes (1:1) to give 321 mg of a white solid.

To a stirred solution of this product (2 g in a mixture of toluene (60 mL) and acetone (20 mL) was added Pd(OH)₂/C (700 mg). The suspension was stirred for 5 hours at RT under hydrogen (balloon pressure). The mixture was filtered through celite and the filtrated was concentrated under reduced pressure to give 2 g of crude material that was used without further purification.

The crude material (2 g, 1.85 mmol) was dissolved in DCM (20 mL). Trichloroacetonitrile (0.64, 3.7 mmol) and sodium hydride (75 mg, 3.1 mmol) were added and the mixture was stirred at RT for 1 h. The reaction mixture was poured onto ice water (20 mL) and was extracted with DCM (2×20 mL). The combined extract was dried over sodium sulfate, was filtered and was concentrated to a residue that was purified by silica gel column chromatography using hexanes:ethyl acetate (7:3) to give 920 mg of the title compound.

Example 21

2-Azido ethyl [O-β-D-glucopyranosyl-1,6]₅-β-D-glucopyranoside (formula 33)

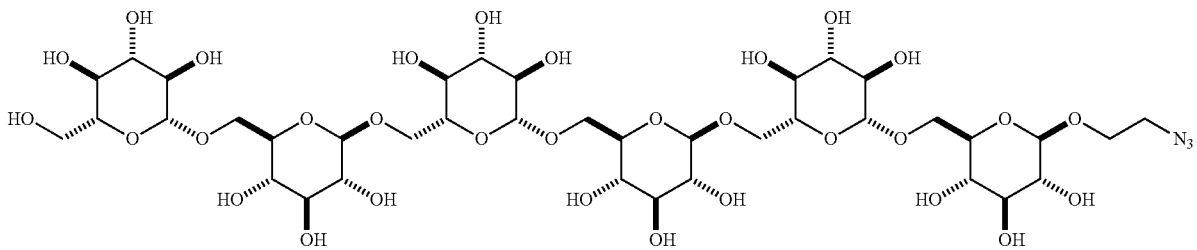

A mixture of the product from Example 18 (280 mg, 0.14 mmol) and the product from Example 20 (518 mg, 0.42 mmol) was co-evaporated with toluene (2×5 mL) and was kept under high vacuum for 1 h. This mixture was dissolved in DCM (16 ml) and was cooled to 0° C. TMSOTf ((8 mg, 0.036 mmol) was added and stirring was continued for 30 min at RT. The reaction mixture was poured onto saturated sodium bicarbonate solution (10 mL) and the organic layer was separated. The organic layer was dried over sodium sulfate, was filtered and was concentrated in vacuo. The crude product was purified by silica gel column chromatography using hexane:ethyl acetate (2:3) to give 140 mg of a white foam.

This material was dissolved in a mixture of methanol (5 mL) and DCM (5 mL). A solution of sodium methoxide in methanol (0.2 mL, 25% wt/v) was added and stirring continued overnight at RT. The mixture was neutralized with acid resin (Dowex 50) and was filtered away from the resin. The filtrated was concentrated and the crude product was purified by silica gel column chromatography using methanol/IPA (4:1) to obtain 41 mg of the title compound: m/z=1060 (M+H⁺), 1082 (M+Na⁺).

Example 22

Phenyl [O-β-D-glucopyranosyl-1,6]₅-1-thio-D-glucopyranoside

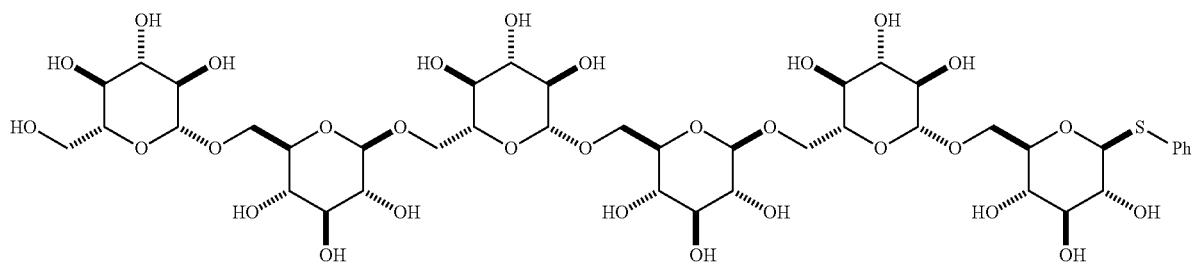

(formula 34)

To a solution of [O-β-D-glucopyranosyl-1,6-]₅-D-glucose (29.1 mg, 0.029 mmol) from Example 2 in H$_2$O (240 μL) and ACN (60 μL) was added thiophenol (15.0 μL, 0.145 mmol) and triethylamine (10.0 μL, 0.290 mmol). The resultant solution was cooled to 0° C., and to this was added a solution of DMC (5.0 mg, 0.029 mmol) in water (10 μL). Stirring was maintained at 0° C. for 1.5 hours, after which an additional portion of DMC (5.0 mg in 10 μL) was added. The reaction allowed to warm slowly to room temperature over the next hour. Two further additions of DMC (5.0 mg in 10 μL H$_2$O) were made at 1 hour intervals (fresh solutions were prepared each time) at 0° C. with subsequent warming to room temperature. At the end of that time, the reaction mixture was concentrated in vacuo to remove volatiles, providing a white pasty solid. Purification by flash column chromatography [n-BuOH/EtOH/H$_2$O, 3:2:2] yielded 13.5 mg of the target compound as a white solid. LC/MS: Rt 4.36 min; m/z=1104.3 [M+Na$^+$].

Similarly prepared by this method are:

34a. a 4-mer: phenyl [O-β-D-glucopyranosyl-1,6]₃-1-thio-D-glucopyranoside, m/z=761 [M+Na$^+$];

34b. A 5-mer: phenyl [O-β-D-glucopyranosyl-1,6]₄-1-thio-D-glucopyranoside, m/z=943 [M+Na$^+$];

34c. A 7-mer: phenyl [O-β-D-glucopyranosyl-1,6]₆-1-thio-D-glucopyranoside, m/z=1267 [M+Na$^+$];

34d. An 8 mer: phenyl [O-β-D-glucopyranosyl-1,6]₇-1-thio-D-glucopyranoside, m/z=1429 [M+Na$^+$];

34e. A 9-mer: phenyl [O-D-glucopyranosyl-1,6]₈-1-thio-D-glucopyranoside, m/z=1591 [M+Na$^+$]; and 34f. a 10-mer: phenyl [O-β-D-glucopyranosyl-1,6]₉-1-thio-D-glucopyranoside, m/z=1753 [M+Na$^+$].

Example 23

Ethylthio-O-2,3,4,6-tetra-O-acetyl-D-glucopyranosyl-β-1,6-O-2,3,4-tri-O-acetyl-D-glucopyranosyl-O-1,6-O-2,3,4-tri-O-acetyl-D-glucopyranosyl-β-1,6-O-2,3,4-tri-O-acetyl-D-glucopyranosyl-β-1,6-O-2,3,4-tri-O-acetyl-D-glucopyranosyl-β-1,6-β-D-glucopyranose tetraacetate

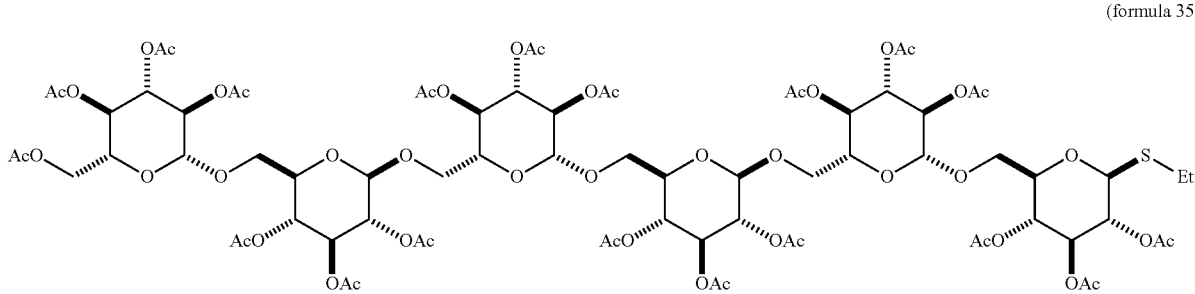

(formula 35)

To a solution of the hexasaccharide peracetate (5.0 mg, 0.0027 mmol) from Example 11 in anhydrous DCM (91 μL) at −10° C. under argon was added ethanethiol (4.0 μL, 0.054 mmol, 20 equiv) followed by boron trifluoride diethyl etherate (10% v/v in DCM, 17 μL, 0.0135 mmol). The resultant solution was stirred at that temperature for 2.5 hours, and then was quenched at 0° C. by addition of sat aqueous NaHCO$_3$. The mixture was warmed to room temperature followed by extractive work-up (H$_2$O/3×DCM). The combined organic extract was washed with brine, dried (MgSO$_4$), filtered and concentrated in vacuo to provide 5 mg (>95%) of the crude product as a clear residue: m/z=1856 [M+Na$^+$].

Example 24

Synthesis of [(2R,3R,4S,5R,6R)-4,5-dibenzoyloxy-6-hydroxy-2-[[(2R,3R,4S,5R,6R)-3,4,5-tribenzoyloxy-6-(benzoyloxymethyl)tetrahydropyran-2-yl]oxymethyl]tetrahydropyran-3-yl]methyl benzoate

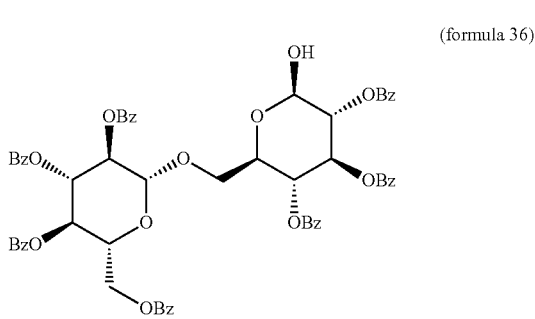

(formula 36)

A solution of amygdalin (10 g, 22 mmol) in pyridine (80 mL) was cooled to 0° C. and then successively treated with DMAP (0.27 g, 2.2 mmol, 0.1 equiv.) and dropwise with benzoyl chloride (23 mL, 164 mmol, 9 equiv.). After addition of the benzoyl chloride was completed, the reaction mixture was kept stirring at 0° C. and then after 2 hours, warmed to room temperature. The mixture was left stirring for an additional 16 hours. The reaction mixture was poured onto water (200 mL) and extracted with methylene chloride (2×200 mL). The combined organic extract was then successively washed with 2N HCl (2×75 mL) and then saturated aqueous NaHCO$_3$ (3×75 mL), and then dried (NaSO$_4$). The solvent was removed in vacuo and the residue was purified by recrystallization via ethanol or acetone/hexanes to afford [(2R,3R,4S,5R,6R)-3,4,5-tribenzoyloxy-6-[[(2R,3R,4S,5R,6R)-3,4,5-tribenzoyloxy-6-[cyano(phenyl)methoxy]tetrahydro-pyran-2-yl]methoxy]tetrahydropyran-2-yl]methyl benzoate (20.9 g, yield 81%).

A solution of [(2R,3R,4S,5R,6R)-3,4,5-tribenzoyloxy-6-[[(2R,3R,4S,5R,6R)-3,4,5-tribenzoyl-oxy-6-[cyano(phenyl)methoxy]tetrahydropyran-2-yl]methoxy]tetrahydropyran-2-yl]methyl benzoate (20 g, 17 mmol) in toluene (440 mL) and acetone (350 mL) was degassed in vacuo and then placed under an atmosphere of hydrogen. The solution was then treated with 50% wetted 20% Pd(OH)$_2$ on carbon (8.7 g, 6.2 mmol, 0.4 equiv). After stirring overnight under a balloon atmosphere of hydrogen, TLC and LC/MS analysis indicated complete consumption of starting material and conversion to the desired product. The reaction mixture was filtered through Celite 545 and solvent was removed in vacuo. The residue was passed through a plug of silica prior to purification via crystallization from ethanol to afford [(2R,3R,4S,5R,6R)-4,5-dibenzoyloxy-6-hydroxy-2-[[(2R,3R,4S,5R,6R)-3,4,5-tribenzoyloxy-6-(benzoyloxymethyl)tetrahydropyran-2-yl]oxymethyl]tetrahydropyran-3-yl]methyl benzoate (16.8 g, yield 93%).

Example 25

Synthesis of [(2R,3R,4S,5R,6R)-4,5-dibenzoyloxy-6-hydroxy-2-[[(2R,3R,4S,5R,6R)-3,4,5-tribenzoyloxy-6-[[dimethyl(1,1,2-trimethylpropyl)silyl]oxymethyl]tetrahydropyran-2-yl]oxymethyl]tetrahydropyran-3-yl] benzoate

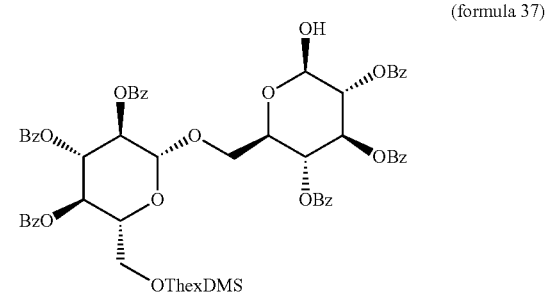

(formula 37)

A solution of amygdalin (60 g, 0.13 mol) in DMF (330 mL) was successively treated with imidazole (19.6 g, 0.29 mol, 2.2 equiv) and then dimethylthexylchlorosilane (42.2 mL, 0.24 mole, 1.80 equiv). After stirring for 16 hrs., TLC and LC/MS analysis indicated the clean conversion of the starting material to desired product. The reaction mixture was quenched with ice/water (1500 mL) and filtered after 1 h, washing with cold water, to afford a white solid product. The crude product was dried at 45° C. under high vacuum overnight, treated with hexane (300 mL), and then filtered to afford product 2-[(2R,3R,4S,5S,6R)-6-[[(2R,3R,4S,5S,6R)-6-[[dimethyl(1,1,2-trimethylpropyl)silyl]oxymethyl]-3,4,5-trihydroxy-tetrahydropyran-2-yl]oxymethyl]-3,4,5-trihydroxy-tetrahydropyran-2-yl]oxy-2-phenyl-acetonitrile as a white powder (62.0 g, 79 yield %), which was used directly for the next step.

Benzoyl chloride (64 mL, 0.55 mol) was added with stirring at 0° C. to a solution of product 2-[(2R,3R,4S,5S,6R)-6-[[(2R,3R,4S,5S,6R)-6-[[dimethyl(1,1,2-trimethylpropyl)silyl]oxymethyl]-3,4,5-trihydroxy-tetrahydropyran-2-yl]oxymethyl]-3,4,5-trihydroxy-tetrahydropyran-2-yl]oxy-2-phenyl-acetonitrile (30.0 g, 0.05 mol) in pyridine (300 mL) and the mixture was stirred overnight at room temperature. Water (250 mL) and ethyl acetate (250 mL) was added, and the organic lawyer was washed with 1N HCl (150 mL), aqueous saturated NaHCO$_3$ (2×150 mL) and aqueous saturated NaCl (2×150 mL), dried over anhydrous Na$_2$SO$_4$. After concentration, the residue was treated with a large amount of hexane and stirred till a white solid powder formed. After filtration, the desired product [(2R,3R,4S,5R,6R)-4,5-dibenzoyloxy-6-[cyano(phenyl)methoxy]-2-[[(2R,3R,4S,5R,6R)-3,4,5-tribenzoyloxy-6-[[dimethyl(1,1,2-trimethylpropyl)silyl]oxymethyl]tetrahydropyran-2-yl]oxymethyl]tetrahydropyran-3-yl] benzoate was obtained as white solid powder (49.0 g, yield 80%).

The mixture of [(2R,3R,4S,5R,6R)-4,5-dibenzoyloxy-6-[cyano(phenyl)methoxy]-2-[[(2R,3R,4S,5R,6R)-3,4,5-tribenzoyloxy-6-[[dimethyl(1,1,2-trimethylpropyl)silyl]oxymethyl]tetrahydropyran-2-yl]oxymethyl]tetrahydropyran-3-yl] benzoate (30.0 g, 20 mmol) in toluene (610 mL) and acetone (500 mL) was degassed with H$_2$ for 30 min. Then 50% wetted 20% Pd(OH)$_2$ on carbon (4.5 g, 3.2 mmol, 15 mol %) was added carefully and the whole reaction system was degassed with H$_2$ again for 15 min. The reaction was stirred under balloon pressure of H₂ at room temperature for 24 h. The reaction mixture was passed through a Celite 545 pad and washed with ethyl acetate. The filtrate was concentrated with rotary evaporator to afford a crude product as oil. The residue was purified by passing through a short silica gel pad washing with ethyl acetate/hexane (0-20%). After evaporation of solvent, product [(2R,3R,4S,5R,6R)-4,5-dibenzoyloxy-6-hydroxy-2-[[(2R,3R,4S,5R,6R)-3,4,5-tribenzoyloxy-6-[[dimethyl(1,1,2-trimethylpropyl)silyl]oxymethyl]tetrahydropyran-2-yl]oxymethyl]tetrahydropyran-3-yl] benzoate was obtained as a white form (26.1 g, yield 96%).

Example 26

Synthesis of [(2R,3R,4S,5R)-6-allyloxy-4,5-dibenzoyloxy-2-(hydroxymethyl)tetrahydropyran-3-yl] benzoate

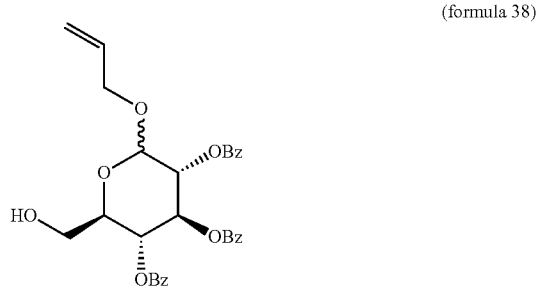

(formula 38)

Allyl alcohol (28.0 mL, 0.411 mol) was cooled to 0° C. and acetyl chloride (4.3 mL, 0.0611 mol) was added slowly at 0-5° C. D-glucose (10.0 g, 56 mmol) was added slowly at the same temperature and then warmed to room temperature in about 0.5-1 hour. The reaction mixture was stirred at 40° C. for 24 hours. The reaction was cooled by ice-water bath and then neutralized with free base resin Amberlite IRA-67 (30 g, prewashed with acetonitrile) to pH=7. After filtration, the filtrate was concentrated under vacuum to afford an oil. After co-evaporating with toluene (50 mL) twice and the residue was purified by passing through a short silica gel pad (eluent: DCM/MeOH, 0-15%). A white foam was obtained consistent with the product (3R,4S,5S,6R)-2-allyloxy-6-(hydroxymethyl)tetrahydropyran-3,4,5-triol (7.4 g, yield 61%) and it was carried forward without any further purification.

A solution of (3R,4S,5S,6R)-2-allyloxy-6-(hydroxymethyl)tetrahydropyran-3,4,5-triol (5.0 g, 22.7 mmol) in anhydrous pyridine was successively treated with chlorotriphenylmethane (6.97 g, 25.0 mmol) and then DMAP (0.28 g, 2.27 mmol). The reaction was warmed to 80° C. and stirred till the reaction was completed (about 3h). The reaction solvent was evaporated and ethyl acetate was added. The organic phase was washed with aqueous saturated NaHCO₃ and brine, dried over anhydrous Na₂SO₄. The solvent was concentrated and the residue was purified by passing through a short silica gel pad (eluent: ethyl acetate/hexane 0-100%) to afford desired product (3R,4S,5S,6R)-2-allyloxy-6-(trityloxymethyl)tetrahydropyran-3,4,5-triol (9.5 g, yield 91%).

Benzoyl chloride (7.5 mL, 64.1 mmol) was added to a 0° C. solution of (3R,4S,5S,6R)-2-allyloxy-6-(trityloxymethyl)tetrahydropyran-3,4,5-triol (5.0 g, 10.8 mmol) in anhydrous pyridine (70 mL) followed by addition of DMAP (0.4 g, 3.2 mmol). The reaction mixture was warmed to room temperature and stirred till the reaction was completed (about 5 hours). The reaction solvent was evaporated and ethyl acetate and saturated aqueous NaHCO₃ was added to the reaction flask. The organic layer was separated and washed with brine, dried over anhydrous Na₂SO₄. Then after concentration, the residue was purified by passing through a short silica gel pad (EtOAc/hexane, 0-10%) to afford the desired product [(2R,3R,4S,5R)-6-allyloxy-4,5-dibenzoyloxy-2-(trityloxymethyl)tetrahydropyran-3-yl] benzoate (total 8.2 g, yield 98%).

BF₃.OEt₂ (5.6 mL, 45.2 mmol) was added slowly to the solution of [(2R,3R,4S,5R)-6-allyloxy-4,5-dibenzoyloxy-2-(trityloxymethyl)tetrahydropyran-3-yl] benzoate (35.0 g, 45.2 mmol) in MeOH/DCM (75 mL/150 mL, v/v=1/2) at 0° C. The reaction mixture was warmed to room temperature in 30 min and stirred till the reaction was completed (about 6 hours). The reaction was cooled down by ice-bath and quenched with NEt₃ (6.3 mL, 45.2 mmol). After concentration, the residue was purified on a plug of silica gel (5×SiO₂, methylene chloride, 4 plug volumes followed by 40% ethyl acetate/hexanes 4 plug volumes) to afford product [(2R,3R,4S,5R)-6-allyloxy-4,5-dibenzoyloxy-2-(hydroxymethyl)tetrahydropyran-3-yl] benzoate (23.2 g, yield 96%).

Example 27

General Procedure for Formation of Trichloroimidate

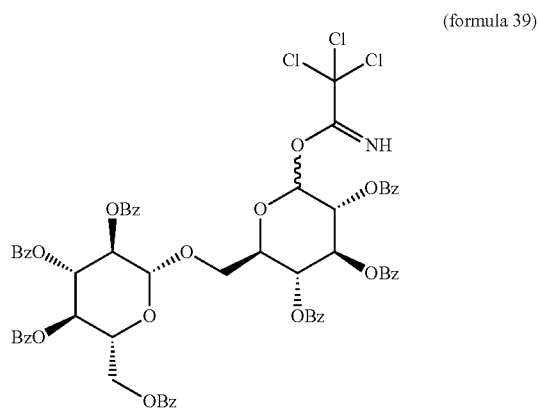

(formula 39)

A solution of [(2R,3S,4S,5R,6R)-3,4,5-trihydroxy-6-[[(2R,3S,4S,5R)-3,4,5,6-tetrahydroxytetrahydropyran-2-yl]methoxy]tetrahydropyran-2-yl]methyl benzoate (10.0 g, 9.3 mmol) in anhydrous methylene chloride (24 mL) was cooled to 0° C. and successively treated with trichloroacetonitrile (1.9 mL, 19.2 mmol, 2.1 equiv) and then DBU (0.28 mL, 1.9 mmol, 0.2 equiv.). After 10 min., the solution was warmed to room temperature and the reaction was continued for an additional 3 hrs. By TLC analysis, the starting material was fully consumed and a new higher R_f spot formed demonstrating full conversion to the trichloroimidate product. The concentrated reaction mixture was purified by passage through a plug of deactivated silica (10× weigh excess silica, deactivated by prewashing with 0.2% triethylamine in hexanes and then washing off the excess triethylamine with hexanes, elution with 40% ethyl acetate/hexanes) to elute the product as an pale yellow solid (10.3 g).

Similarly prepared by the method of this example were:

a.

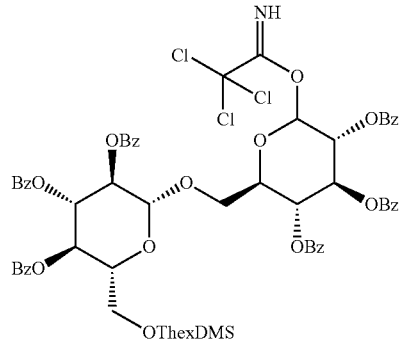

(formula 40)

1-O-(2,2,2-trichloro ethanimidoyl)-6-O—[O-β-(2,3,4-tri-O-benzoyl)-6-O-[dimethyl(1,1,2-trimethylpropyl)silyl]-D-glucopranosyl-(1,6)]-D-glucopyranose 2,3,4-tri-O-benzoate;

b.

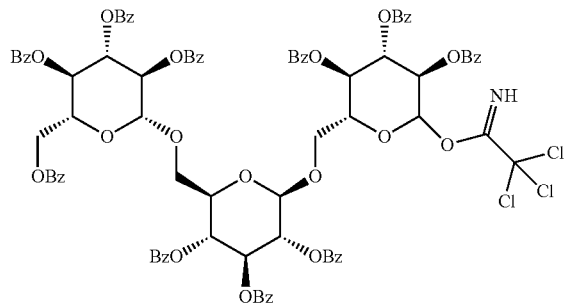

(formula 41)

1-O-(2,2,2-trichloroethanimidoyl)-6-O-[1-O-β-[O-β-(2,3,4-tri-O-benzoyl)-D-glucopranosyl-(1,6)]-(2,3,4,6-tetra-O-benzoyl)-D-glucopranosyl]-D-glucopyranose 2,3,4-tri-O-benzoate;

c.

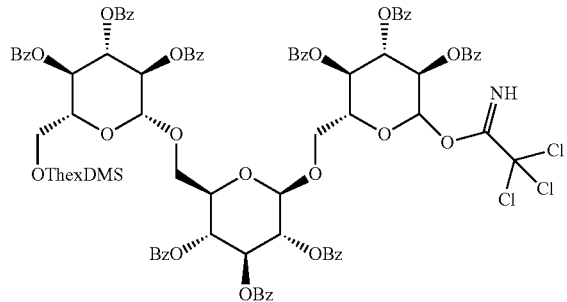

(formula 42)

1-O-(2,2,2-bichloroethanimidoyl)-6-O-[1-O-β-[O-β-(2,3,4-tri-O-benzoyl)-D-glucopranosyl-(1,6)]-(2,3,4-tri-O-benzoyl)-6-O-[dimethyl(1,1,2-trimethylpropyl)silyl]-D-glucopranosyl]-D-glucopyranose 2,3,4-tri-O-benzoate;

d.

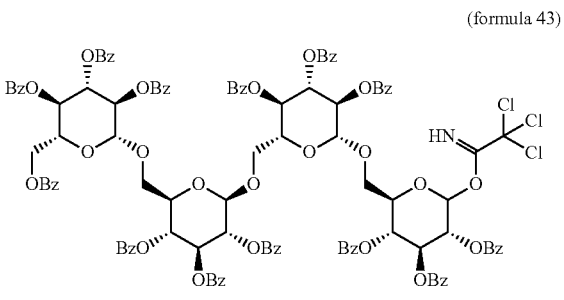

(formula 43)

1-O-(2,2,2-bichloroethanimidoyl)-6-O-[1-O-β-[O-β-(2,3,4-tri-O-benzoyl)-D-glucopranosyl-(1,6)]₂-(2,3,4,6-tetra-O-benzoyl)-D-glucopranosyl]-D-glucopyranose 2,3,4-tri-O-benzoate;

e.

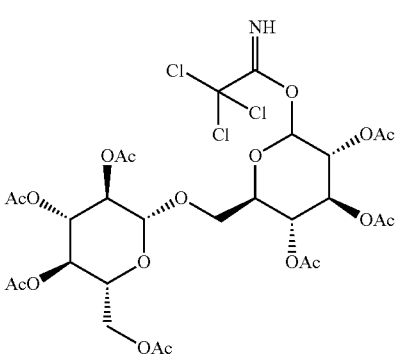

(formula 44)

1-O-(2,2,2-trichloroethanimidoyl)-6-O—[O-β-(2,3,4,6-tetra-O-acetyl)-D-glucopranosyl-(1,6)]-D-glucopyranose 2,3,4-tri-O-acetate;

f.

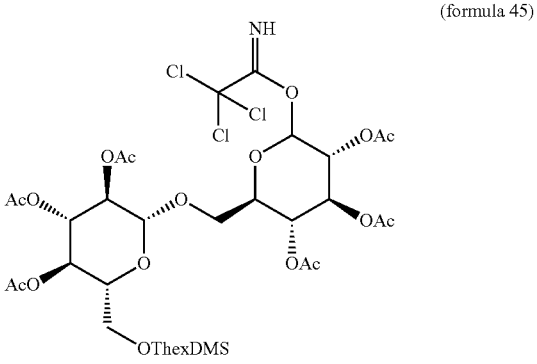

(formula 45)

1-O-(2,2,2-trichloroethanimidoyl)-6-O—[O-β-(2,3,4,6-tri-O-acetyl)-6-O-[dimethyl(1,1,2-trimethylpropyl)silyl]-D-glucopranosyl-(1,6)]-D-glucopyranose 2,3,4-tri-O-acetate;

g.

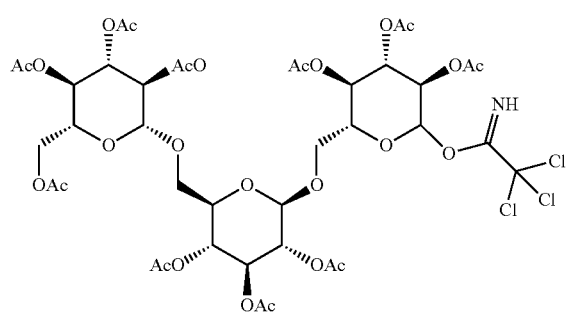
(formula 46)

1-O-(2,2,2-trichloroethanimidoyl)-6-O—[1-O-β-[O-β-(2,3,4-tri-O-acetyl)-D-glucopranosyl-(1,6)]-(2,3,4,6-tetra-O-acetyl)-D-glucopranosyl]-D-glucopyranose 2,3,4-tri-O-acetate;

h.

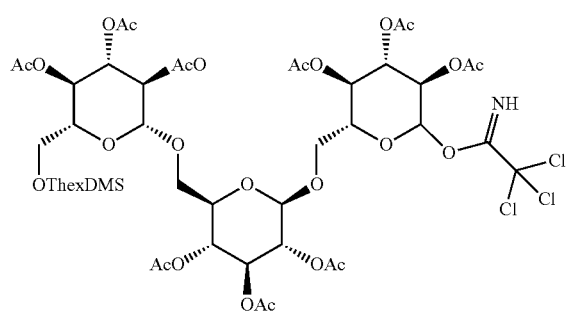
(formula 47)

1-O-(2,2,2-trichloroethanimidoyl)-6-O-[1-O-β-[O-β-(2,3,4-tri-O-acetyl)-D-glucopranosyl-(1,6)]-(2,3,4-tri-O-acetyl)-6-O-[dimethyl(1,1,2-trimethylpropyl)silyl]-D-glucopranosyl]-D-glucopyranose 2,3,4-tri-O-acetate; and i.

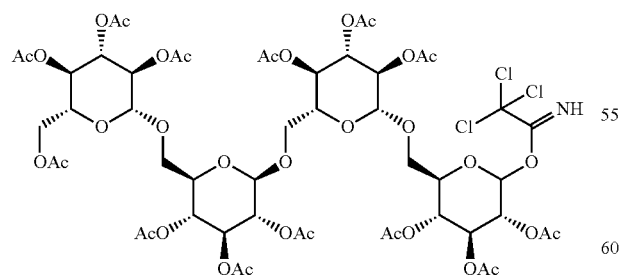
(formula 48)

1-O-(2,2,2-trichloroethanimidoyl)-6-O-[1-O-β-[O-β-(2,3,4-tri-O-acetyl)-D-glucopranosyl-(1,6)]₂-(2,3,4,6-tetra-O-acetyl)-D-glucopranosyl]-D-glucopyranose 2,3,4-tri-O-acetate.

The following compounds can also be similarly prepared by the method of this example:

j.

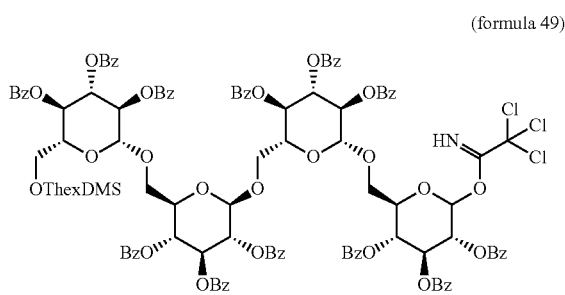
(formula 49)

1-O-(2,2,2-trichloro ethanimidoyl)-6-[[O-β-(2,3,4-tri-O-benzoyl)-D-glucopranosyl-(1,6)]₂-[O-β-(2,3,4-tri-O-benzoyl)-6-O-[dimethyl(1,1,2-trimethylpropyl)silyl]-D-glucopranosyl]]-D-glucopyranose 2,3,4-tri-O-benzoate;

k.

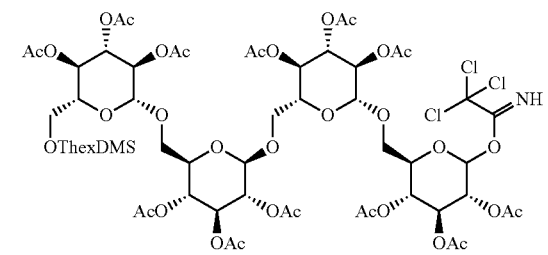
(formula 50)

1-O-(2,2,2-trichloro ethanimidoyl)-6-[[O-β-(2,3,4-tri-O-acetyl)-D-glucopranosyl-(1,6)]₂-[O-β-(2,3,4-tri-O-acetyl)-6-O-[dimethyl(1,1,2-trimethylpropyl)silyl]-D-glucopranosyl]]-D-glucopyranose 2,3,4-tri-O-acetate;

l.
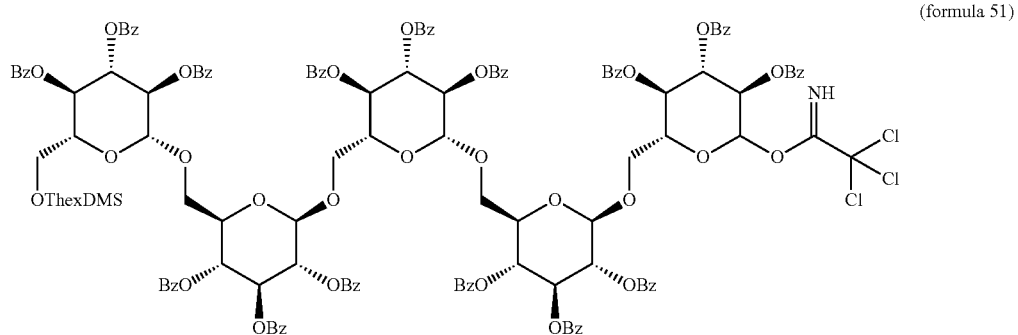
(formula 51)
1-O-(2,2,2-trichloroethanimidoyl)-6-O-[[O-β-(2,3,4-tri-O-benzoyl)-D-glucopranosyl-(1,6)]$_3$-[O-β-(2,3,4-tri-O-benzoyl)-6-O-[dimethyl(1,1,2-trimethylpropyl)silyl]-D-glucopranosyl]]-D-glucopyranose 2,3,4-tri-O-benzoate; and
m.
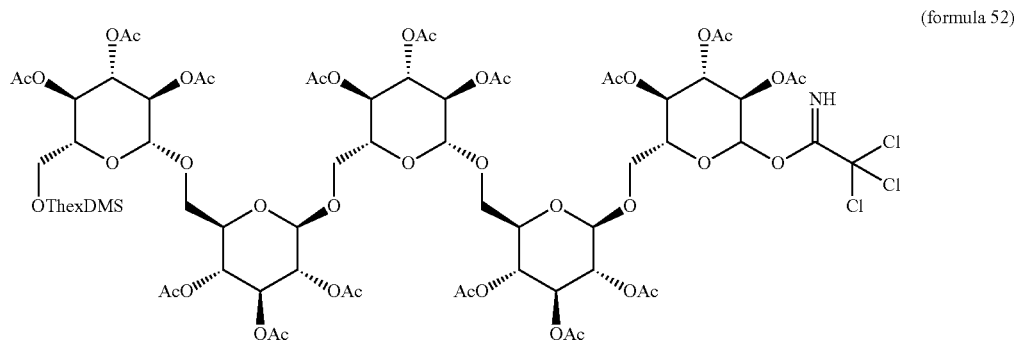
(formula 52)
1-O-(2,2,2-trichloroethanimidoyl)-6-O-[[O-β-(2,3,4-tri-O-acetyl)-D-glucopranosyl-(1,6)]$_3$-[O-β-(2,3,4-tri-O-acetyl)-6-O-[dimethyl(1,1,2-trimethylpropyl)silyl]-D-glucopranosyl]]-D-glucopyranose 2,3,4-tri-O-acetate.

Example 28

General Glycosylation Conditions (formula 53)

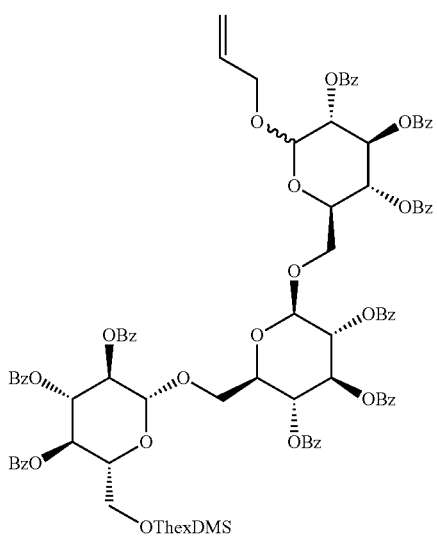

A solution of 1-O-(2,2,2-trichloroethanimidoyl)-6-O-[1-O-β-[O-β-(2,3,4-tri-O-benzoyl)-D-glucopranosyl]-(2,3,4-tri-O-benzoyl)-6-O-[dimethyl(1,1,2-trimethylpropyl)silyl]-D-glucopranosyl]-D-glucopyranose 2,3,4-tri-O-benzoate (11.4 g, 9.1 mmol) and 1-O-(2-propeny-1-yl)-D-glucopyranose 2,3,4-tri-O-benzoate (5.30 g, 9.96 mmol, 1.1 equiv) were added to an oven dried (150° C., >24 hrs) flask that was pre-cooled under an argon atmosphere. The mixture was placed under high vacuum for 1 hr and then the vessel was back-filled with Ar. The mixture was then dissolved with methylene chloride (45 mL) and then treated with pre-dried molecular sieves (powder). The mixture was then cooled to −40° C. (acetonitrile/dry ice bath) and after 1 hr treated dropwise with TMSOTf (0.33 mL, 1.8 mmol, 0.2 equiv.). After stirring for 4 hrs, the reaction mixture was quenched with triethylamine (0.4 mL, 3.6 mmol, 2.0 equiv) and then warmed to room temperature. The reaction mixture was filtered through Celite 545 and pad was washed with methylene chloride (2×50 mL). The combined filtrates were washed with saturated aqueous $NaHCO_3$ (25 mL) and then saturated aqueous NaCl (25 mL). The organic layer was dried ($NaSO_4$) and the solvent was removed in vacuo. The product was purified by flash chromatography (10× silica, 0-40% ethyl acetate/hexanes) to afford the product as a white solid (12.5 g): m/z=1624 (M+H$^+$); 1641 (M+NH$_4^+$); 1646 (M+Na$^+$).

Similarly prepared by the method of this example were:

a. Compounds of Formula 54

(formula 54)

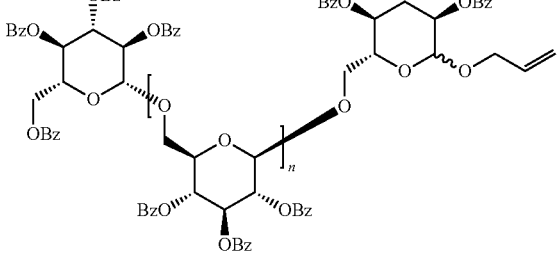

54a. a 3-mer (n=1): 1-O-(2-propen-1-yl)-6-O-[1-O-β[O-β-(2,3,4-tri-O-benzoyl)-D-glucopranosyl-(1,6)]-(2,3,4,6-tetra-O-benzoyl)-D-glucopranosyl]-D-glucopyranose 2,3,4-tri-O-benzoate: m/z=1585 (M+H$^+$); 1602 (M+NH$_4^+$); 1607 (M+Na$^+$);

54b. a 5-mer (n=3): 1-O-(2-propen-1-yl)-6-O-[1-O-β-[O-β-(2,3,4-tri-O-benzoyl)-D-glucopranosyl-(1,6)]$_3$-(2,3,4,6-tetra-O-benzoyl)-D-glucopranosyl]-D-glucopyranose 2,3,4-tri-O-benzoate: m/z=1268 ((M+2H$^+$)/2); 1276 ((M+NH$_4$+H$^+$)/2); 1279 ((M+Na$^+$+H$^+$)/2); and 54c. a timer (n=4): 1-O-(2-propen-1-yl)-6-O-[1-O-β-[O-β-(2,3,4-tri-O-benzoyl)-D-glucopranosyl-(1,6)]$_4$-(2,3,4,6-tetra-O-benzoyl)-D-glucopranosyl]-D-glucopyranose 2,3,4-tri-O-benzoate: m/z=1505 ((M+2H$^+$)/2); 1513 ((M+NH$_4$+H$^+$)/2); 1516 ((M+Na$^+$+H$^+$)/2).

b. Compounds of Formula 55

(formula 55)

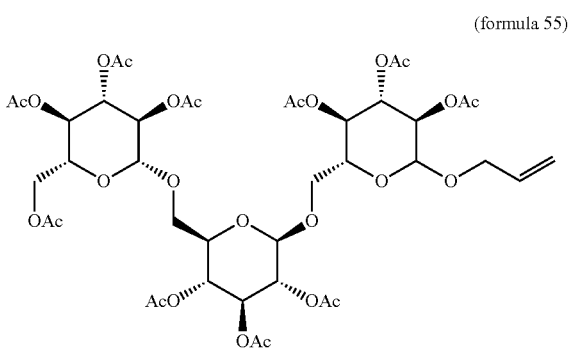 [SMILES: C=CCOC1O[C@H](CO[C@@H]2O[C@H](CO[C@@H]3O[C@H](COC(C)=O)[C@@H](OC(C)=O)[C@H](OC(C)=O)[C@H]3OC(C)=O)[C@@H](OC(C)=O)[C@H](OC(C)=O)[C@H]2OC(C)=O)[C@@H](OC(C)=O)[C@H](OC(C)=O)[C@H]1OC(C)=O]

1-O-(2-propen-1-yl)-6-O-[1-O-β-[O-β-(2,3,4-tri-O-acetyl)-D-glucopranosyl-(1,6)]-(2,3,4,6-tetra-O-acetyl)-D-glucopranosyl]-D-glucopyranose 2,3,4-tri-O-acetate: m/z=965 (M+H$^+$); 982 (M+NH$_4^+$); 987 (M+Na$^+$).

c. Compounds of Formula 56

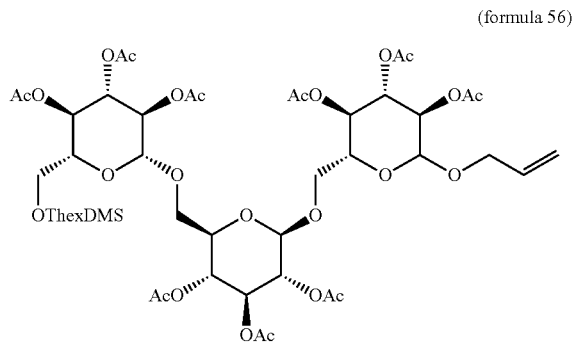

(formula 56)

1-O-(2-propen-1-yl)-6-O-[1-O-β-[O-β-(2,3,4-tri-O-acetyl)-D-glucopranosyl]-(2,3,4-tri-O-acetyl)-6-O-[dimethyl(1,1,2-trimethylpropyl)silyl]-D-glucopranosyl]-D-glucopyranose 2,3,4-tri-O-acetate: m/z=1065 (M+H$^+$); 1082 (M+NH$_4^+$); 1087 (M+Na$^+$).

d. Compounds of Formula 57

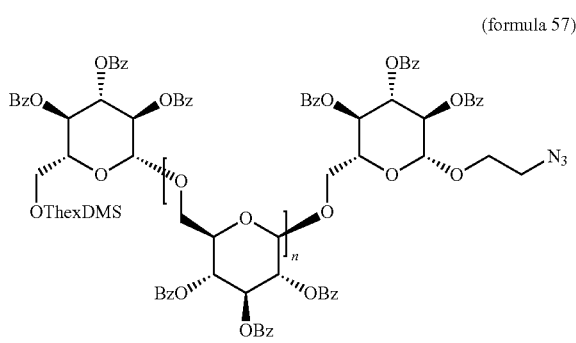

(formula 57)

a 4mer (n=2): 1-O-β-(2-azidoethyl)-6-O-[1-O-β-[O-β (2,3,4-tri-O-benzoyl)-D-glucopranosyl-(1,6)]$_2$(2,3,4-tri-O-benzoyl)-6-O-[dimethyl(1,1,2-trimethylpropyl)silyl]-D-glucopranosyl]-D-glucopyranose-2,3,4-tri-O-benzoate: m/z=1065 ((M+2H$^+$)/2); 1073 ((M+NH$_4$+H$^+$)/2); 1076 ((M+Na$^+$+H$^+$)/2).

e. Compounds of Formula 58

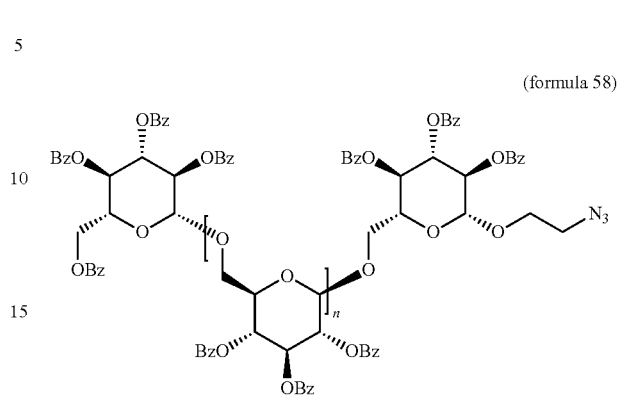

(formula 58)

n=2, 3, or 4

58a. a 4mer (n=2): 1-O-β-(2-azidoethyl)-6-O-[1-[O-β (2,3,4-tri-O-benzoyl)-D-glucopranosyl]$_2$-O-β-(2,3,4,6-tetra-O-benzoyl)-D-glucopranosyl]-D-glucopyranose 2,3,4-tri-O-benzoate: m/z=1046 ((M+2H$^+$)/2); 1054 ((M+NH$_4$+H$^+$)/2); 1057 ((M+Na$^+$+H$^+$)/2);

58b. a 5mer (n=3): 1-O-β(2-azidoethyl)-6-O-[1-[O-β (2,3,4-tri-O-benzoyl)-D-glucopranosyl]$_3$-O-β-(2,3,4,6-tetra-O-benzoyl)-D-glucopranosyl-(1,6)]-D-glucopyranose-2,3,4-tri-O-benzoate: m/z=1283 ((M+2H$^+$)/2); 1291 ((M+NH$_4$+H$^+$)/2); 1294 ((M+Na$^+$+H$^+$)/2); and 58c. a timer (n=4): 1-O-β-(2-azidoethyl)-6-O-[1-[O-β (2,3,4-tri-O-benzoyl)-D-glucopranosyl]$_4$-O-β-(2,3,4,6-tetra-O-benzoyl)-D-glucopranosyl]-D-glucopyranose-2,3,4-tri-O-benzoate: m/z=1520 ((M+2H$^+$)/2); 1528 ((M+NH$_4$+H$^+$)/2); 1531 ((M+Na$^+$+H$^+$)/2).

f. Compounds of Formula 59

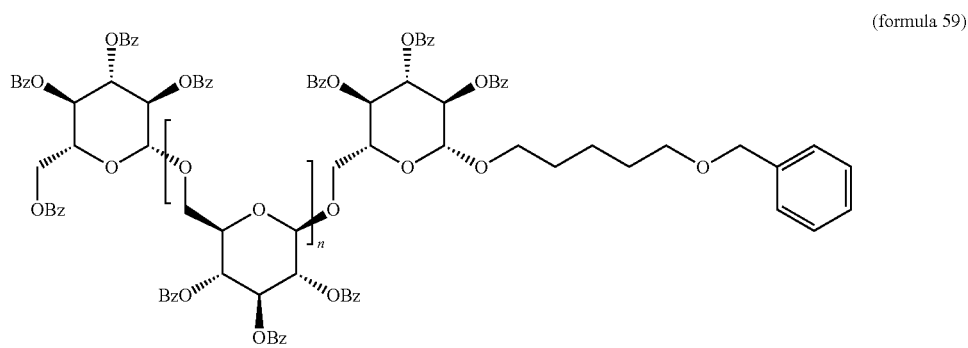

(formula 59)

59a. A 4mer (n=2): 1-O-β-(5-benzyloxypentoxy)-6-O-[1-[O-β (2,3,4-tri-O-benzoyl)-D-glucopranosyl-(1,6)]$_2$-O-β-(2,3,4,6-tetra-O-benzoyl)-D-glucopranosyl]-D-glucopyranose-2,3,4-tri-O-benzoate: m/z=1099 ((M+2H$^+$)/2); 1107 ((M+NH$_4$+H$^+$)/2); 1110 ((M+Na$^+$+H$^+$)/2).

g. Compounds of Formula 60

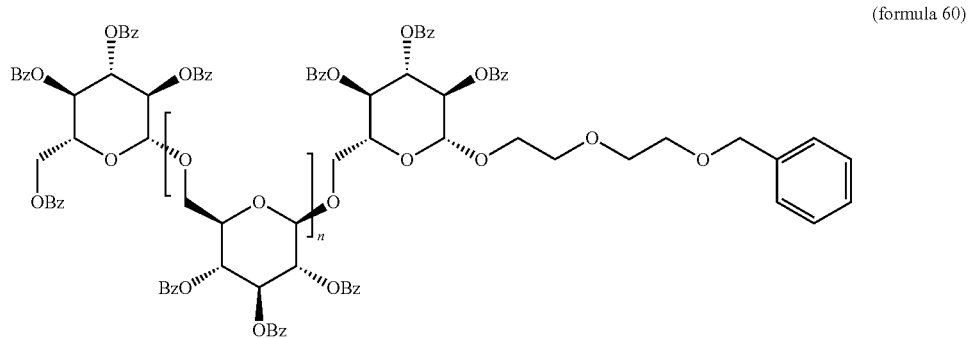
(formula 60)

60a. a 4-mer (n=2): 1-O-β-[2-(2-benzyloxyethoxy)ethoxy]-6-O-[1-[O-β (2,3,4-tri-O-benzoyl)-D-glucopranosyl-(1, 6)]$_2$-O-β-(2,3,4,6-tetra-O-benzoyl)-D-glucopranosyl]-D-glucopyranose-2,3,4-tri-O-benzoate: m/z=1100 ((M+2H$^+$)/2); 1108 ((M+NH$_4$+H$^+$)/2); 1111 ((M+Na$^+$+H$^+$)/2).

The following compounds can also be similarly prepared by the method of this example.

a. Compounds of Formula 61

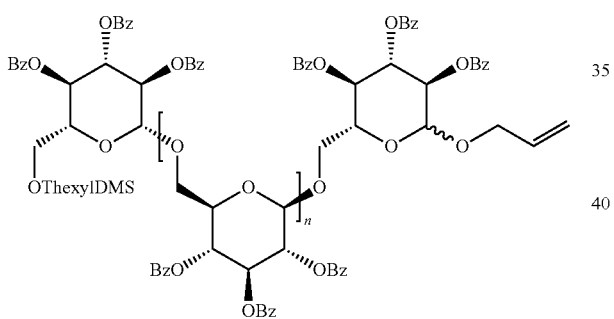
(formula 61)

61a. a 5mer (n=3): 1-O-(2-propen-1-yl)-6-O-[1-β-[O-β-(2,3,4-tri-O-benzoyl)-D-glucopranosyl-(1,6)]$_3$-O-(2,3,4-tri-O-benzoyl)-6-O-[dimethyl(1,1,2-trimethylpropyl)silyl]-D-glucopranosyl]-D-glucopyranose 2,3,4-tri-O-benzoate: theoretical m/z=2572 (M+H$^+$).

b. Compounds of Formula 62

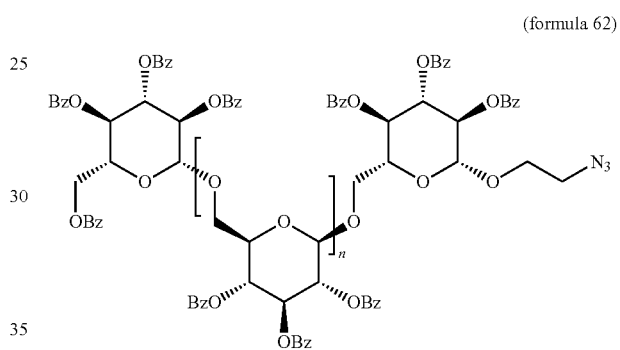
(formula 62)

62a. A 7mer (n=5): 1-O-β-(2-azidoethyl)-6-O-[1-[O-β (2,3,4-tri-O-benzoyl)-D-glucopranosyl]$_5$-O-β-(2,3,4,6-tetra-O-benzoyl)-D-glucopranosyl]-D-glucopyranose-2,3,4-tri-O-benzoate theoretical m/z=3511 (M+H$^+$);

62b. an 8mer (n=6): 1-O-β-(2-azidoethyl)-6-O-[1-[O-β (2,3,4-tri-O-benzoyl)-D-glucopranosyl]$_6$-O-β-(2,3,4,6-tetra-O-benzoyl)-D-glucopranosyl]-D-glucopyranose-2,3,4-tri-O-benzoate theoretical m/z=3995 (M+H$^+$);

62c. a 9mer (n=7): 1-O-β-(2-azidoethyl)-6-O-[1-[O-β (2,3,4-tri-O-benzoyl)-D-glucopranosyl]$_7$-O-β-(2,3,4,6-tetra-O-benzoyl)-D-glucopranosyl]-D-glucopyranose-2,3,4-tri-O-benzoate: theoretical m/z=4479 (M+H$^+$);

c. Compounds of Formula 63

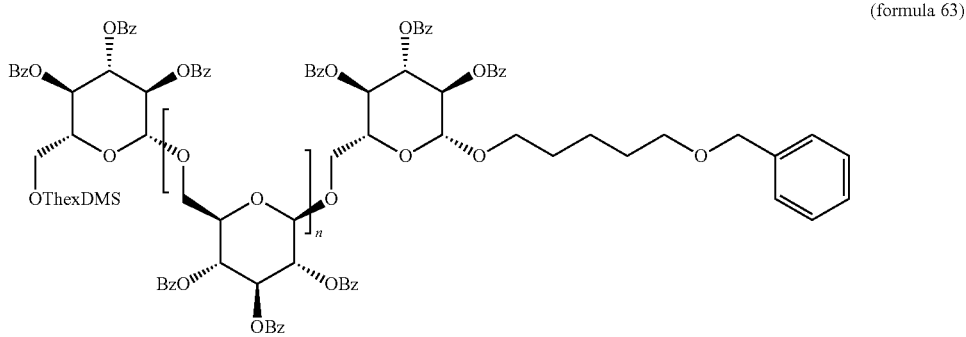
(formula 63)

63a. a 4mer (n=2): 1-O-β-(5-benzyloxypentoxy)-6-O[1-O-β[O-β (2,3,4-tri-O-benzoyl)-D-glucopranosyl-(1,6)]₂(2,3,4-tri-O-benzoyl)-6-O-[dimethyl(1,1,2-trimethylpropyl)si- lyl]-D-glucopranosyl]-D-glucopyranose-2,3,4-tri-O-benzoate: theoretical m/z=2235 (M+H⁺).

d. Compounds of Formula 64

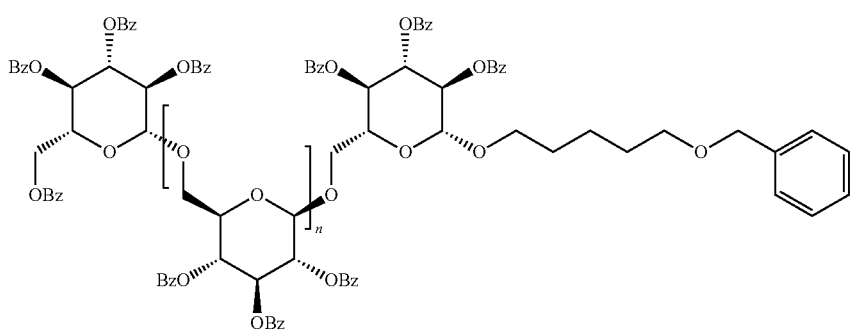

(formula 64)

64a. A 5mer (n=3): 1-O-β-(5-benzyloxypentoxy)-6-O-[1-[O-β (2,3,4-tri-O-benzoyl)-D-glucopranosyl-(1,6)]₃-O-β-(2,3,4,6-tetra-O-benzoyl)-D-glucopranosyl]-D-glucopyranose-2,3,4-tri-O-benzoate: theoretical m/z=2660 (M+H⁺);

64b. a 6mer (n=4): 1-O-β(5-benzyloxypentoxy)-6-O-[1-[O-β (2,3,4-tri-O-benzoyl)-D-glucopranosyl-(1,6)]₄-O-β-(2,3,4,6-tetra-O-benzoyl)-D-glucopranosyl]-D-glucopyranose-2,3,4-tri-O-benzoate: theoretical m/z=3144 (M+H⁺);

64c. a 7mer (n=5): 1-O-β-(5-benzyloxypentoxy)-6-O-[1-[O-β (2,3,4-tri-O-benzoyl)-D-glucopranosyl-(1,6)]₅-O-β-(2,3,4,6-tetra-O-benzoyl)-D-glucopranosyl]-D-glucopyranose-2,3,4-tri-O-benzoate: theoretical m/z=3628 (M+H⁺);

64d. an 8mer (n=6): 1-O-β-(5-benzyloxypentoxy)-6-O-[1-[O-β (2,3,4-tri-O-benzoyl)-D-glucopranosyl-(1,6)]₆-O-β-(2,3,4,6-tetra-O-benzoyl)-D-glucopranosyl]-D-glucopyranose-2,3,4-tri-O-benzoate: theoretical m/z=4112 (M+H⁺); and 64e. a 9mer (n=7): 1-O-β(5-benzyloxypentoxy)-6-O-[1-[O-β (2,3,4-tri-O-benzoyl)-D-glucopranosyl-(1,6)]₇-O-β-(2,3,4,6-tetra-O-benzoyl)-D-glucopranosyl]-D-glucopyranose-2,3,4-tri-O-benzoate: theoretical m/z=4596 (M+H⁺).

e. Compounds of Formula 65

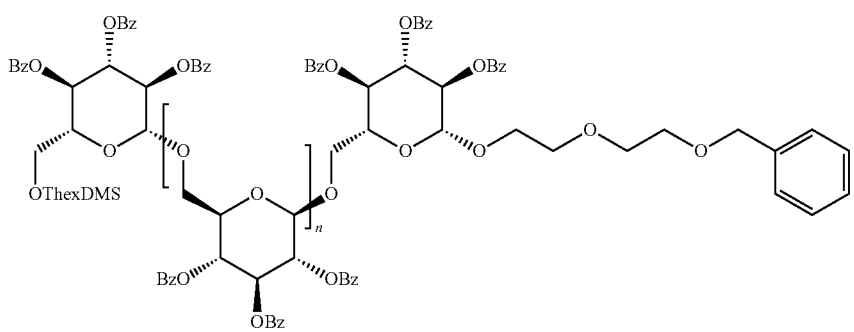

(formula 65)

65a. a 4mer (n=2): 1-O-β-[2-(2-benzyloxyethoxy)ethoxy]-6-O-[1-O-β-[O-β (2,3,4-tri-O-benzoyl)-D-glucopranosyl-(1,6)]₂(2,3,4-tri-O-benzoyl)-6-O-[dimethyl(1,1,2-trimethylpropyl)silyl]-D-glucopranosyl-(1,6)]-D-glucopyranose-2,3,4-tri-O-benzoate: theoretical m/z=2237 (M+H⁺);

And f. Compounds of Formula 66

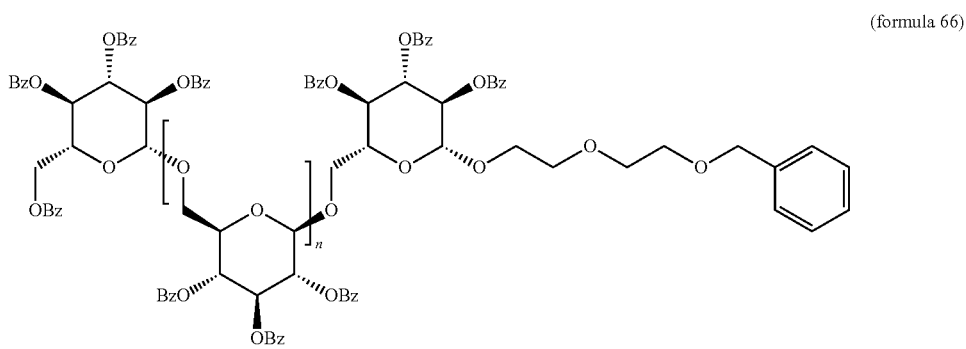

(formula 66)

66a. a 5mer (n=3): 1-O-β-[2-(2-benzyloxyethoxy)ethoxy]-6-O-[1-[O-β (2,3,4-tri-O-benzoyl)-D-glucopranosyl-(1,6)]₃-O-β-(2,3,4,6-tetra-O-benzoyl)-D-glucopranosyl]-D-glucopyranose-2,3,4-tri-O-benzoate: theoretical m/z=2662 (M+H⁺);

66b. a 6mer (n=4): 1-O-β-[2-(2-benzyloxyethoxy)ethoxy]-6-O-[1-[O-β (2,3,4-tri-O-benzoyl)-D-glucopranosyl-(1,6)]₄-O-β-(2,3,4,6-tetra-O-benzoyl)-D-glucopranosyl]-D-glucopyranose-2,3,4-tri-O-benzoate: theoretical m/z=3146 (M+H⁺);

66c. a 7mer (n=5): 1-O-β-[2-(2-benzyloxyethoxy)ethoxy]-6-O-[1-[O-β (2,3,4-tri-O-benzoyl)-D-glucopranosyl-(1,6)]₅-O-β-(2,3,4,6-tetra-O-benzoyl)-D-glucopranosyl]-D-glucopyranose-2,3,4-tri-O-benzoate: theoretical m/z=3630 (M+H⁺);

66d. an 8mer (n=6): 1-O-β-[2-(2-benzyloxyethoxy)ethoxy]-6-O-[1-[O-β (2,3,4-tri-O-benzoyl)-D-glucopranosyl-(1,6)]₆-O-β-(2,3,4,6-tetra-O-benzoyl)-D-glucopranosyl]-D-glucopyranose-2,3,4-tri-O-benzoate: theoretical m/z=4114 (M+H⁺); and 66e. a 9mer (n=7): 1-O-β-[2-(2-benzyloxyethoxy)ethoxy]-6-O-[1-[O-β (2,3,4-tri-O-benzoyl)-D-glucopranosyl-(1,6)]₇-O-β-(2,3,4,6-tetra-O-benzoyl)-D-glucopranosyl]-D-glucopyranose-2,3,4-tri-O-benzoate: theoretical m/z=4598 (M+H⁺).

Example 29

General Conditions for Addition of Alcohol

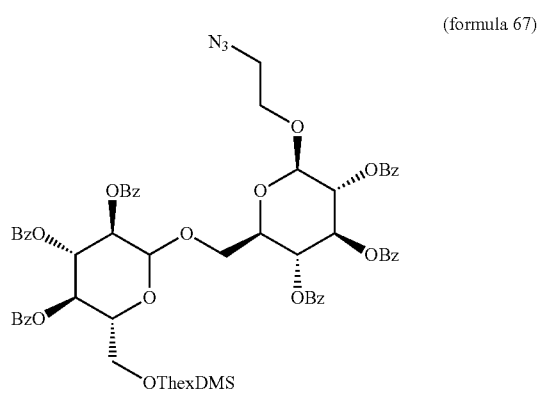

(formula 67)

1-O-(2,2,2-trichloroethanimidoyl)-6-O—[O-β-(2,3,4-tri-O-benzoyl)-6-O-[dimethyl(1,1,2-trimethylpropyl)silyl]-D-glucopranosyl]-D-glucopyranose-2,3,4-tri-O-benzoate (6.8 g, 5.4 mmol) and azidoethanol (0.95 mL, 10.8 mmol, 2.0 equiv) were added to an oven dried (150° C., >24 hrs) flask that was pre-cooled under an argon atmosphere. The mixture was then dissolved with methylene chloride (45 mL) and then treated with pre-dried molecular sieves (powder). The mixture was then cooled to −40° C. (acetonitrile/dry ice) and after 1 hr treated dropwise with TMSOTf (0.20 mL, 1.1 mmol, 0.2 equiv.). After stirring for 4 hrs, the reaction mixture was quenched with triethylamine (0.4 mL, 3.6 mmol, 2.0 equiv) and then warmed to room temperature. The reaction mixture was filtered through Celite 545, and the pad was washed with methylene chloride (2×50 mL). The combined filtrates were washed with saturated aqueous $NaHCO_3$ (25 mL) and then saturated aqueous NaCl (25 mL). The organic layer was dried ($NaSO_4$) and the solvent was removed in vacuo. The product was purified via flash chromatography (10× silica gel, 0-40% ethyl acetate/hexanes) to afford the (5.8 g) as an off-white solid.

Similarly prepared by the method of this example were the following compounds.

a. Compounds of Formula 68

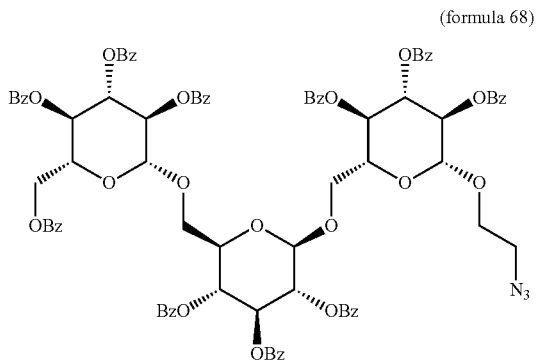

(formula 68)

68a. a 3mer: 1-O-β-(2-azidoethyl)-6-O-[1-β-[O-β (2,3,4-tri-O-benzoyl)-D-glucopranosyl]-O-(2,3,4,6-tetra-O-benzoyl)-D-glucopranosyl]-D-glucopyranose-2,3,4-tri-O-benzoate: m/z=1724 (M+H$^+$); 1742 (M+NH$_4^+$); 1747 (M+Na$^+$).

b. Compounds of Formula 69

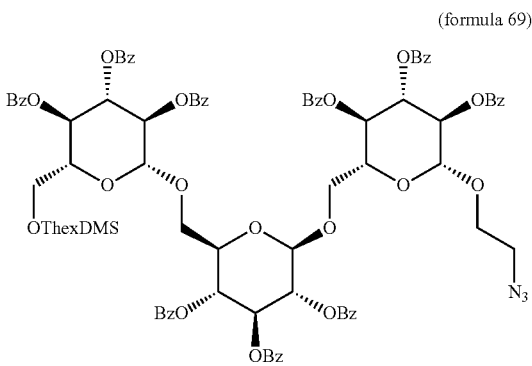

(formula 69)

69a. a 3mer: 1-O-β-(2-azidoethyl)-6-O-[(2,3,4-tri-O-benzoyl)-1-[O-β-(2,3,4-tri-O-benzoyl)-D-glucopranosyl-(1,6)]-6-[dimethyl(1,1,2-trimethylpropyl)silyl]-D-glucopranosyl]-D-glucopyranose 2,3,4-tri-O-benzoate: m/z=1653 (M+H$^+$); 1671 (M+NH$_4^+$); 1676 (M+Na$^+$).

c. Compounds of Formula 70

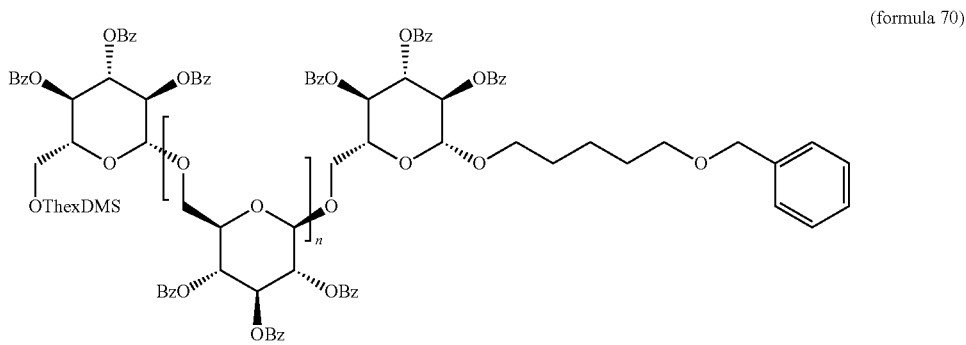

(formula 70)

70a. a 2mer (n=0): 1-O-β-(5-benzyloxypentoxy)-6-[O-β-(2,3,4-tri-O-benzoyl)-6-O-[dimethyl(1,1,2-trimethylpropyl)silyl]-D-glucopranosyl-(1,6)]-D-glucopyranose 2,3,4-tri-O-benzoate: m/z=1286 (M+H$^+$); 1303 (M+NH$_4^+$); 1308 (M+Na$^+$); and d. Compounds of Formula 7a

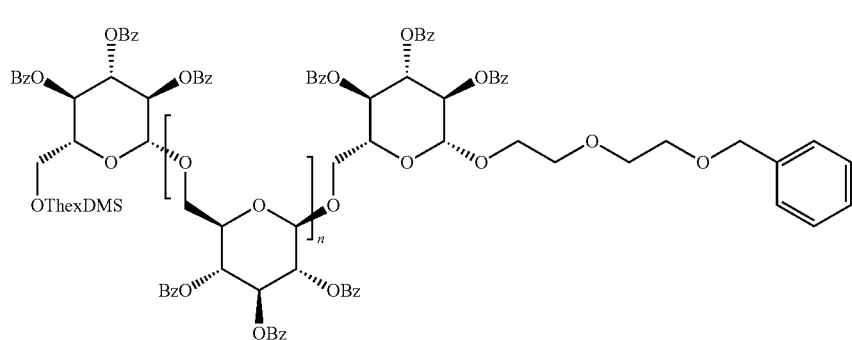
(formula 71)

71a. a 2mer (n=0) 1-O-β-[2-(2-benzyloxyethoxy)ethoxy]-6-O—[O-β-(2,3,4-tri-O-benzoyl)-6-O-[dimethyl(1,1,2-trimethylpropyl)silyl]-D-glucopranosyl]-D-glucopyranose 2,3,4-tri-O-benzoate: m/z=1287 (M+H$^+$); 1304 (M+NH$_4^+$); 1309 (M+Na$^+$).

The following compounds can also be similarly prepared by the method of this example.

a. Compounds of Formula 72

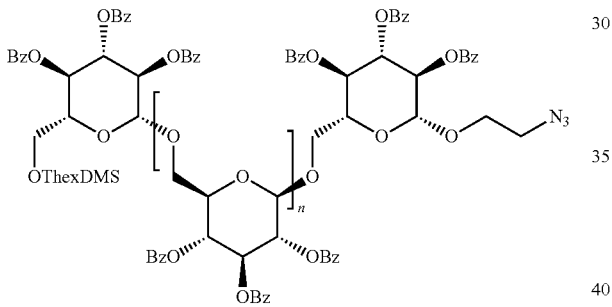
(formula 72)

72a. a 5mer (n=3): 1-O-β-(2-azidoethyl)-6-O-[(2,3,4-tri-O-benzoyl)-1-[O-β-(2,3,4-tri-O-benzoyl)-D-glucopranosyl-(1,6)]$_3$-6-[dimethyl(1,1,2-trimethylpropyl)silyl]-D-glucopranosyl]-D-glucopyranose 2,3,4-tri-O-benzoate: theoretical m/z=2621 (M+H$^+$);

b. Compounds of Formula 73

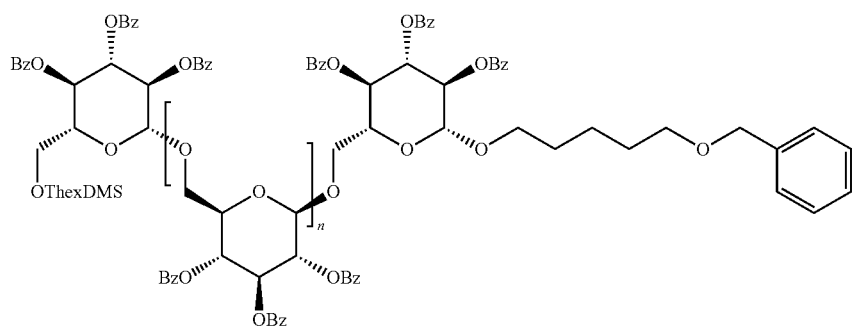
(formula 73)

73a. a 3mer (n=1): 1-O-β-(5-benzyloxypentoxy)-6-O—[O-β-(2,3,4-tri-O-benzoyl)-6-[O-β-(2,3,4-tri-O-benzoyl)-6-O-[dimethyl(1,1,2-trimethylpropyl)silyl]-D-glucopranosyl-(1,6)]-D-glucopyranose 2,3,4-tri-O-benzoate: theoretical m/z=1770 (M+H⁺); and 73b. a 5mer (n=3): 1-O-β-(5-benzyloxypentoxy)-6-O-[(2,3,4-tri-O-benzoyl)-1-[O-β-(2,3,4-tri-O-benzoyl)-D-glucopranosyl-(1,6)]₃-6-O-[dimethyl(1,1,2-trimethylpropyl)silyl]-D-glucopranosyl]-D-glucopyranose 2,3,4-tri-O-benzoate: theoretical m/z=2738 (M+H⁺).

c. Compounds of Formula 74

(formula 74)

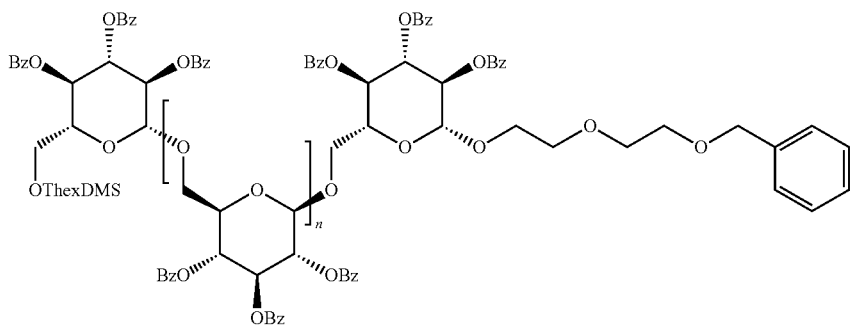

74a. a 3mer (n=1): 1-O-β-[2-(2-benzyloxyethoxy)ethoxy]-6-O—[O-(2,3,4-tri-O-benzoyl)-1-O-β-[O-β-(2,3,4-tri-O-benzoyl)-D-glucopranosyl]-6-O-[dimethyl(1,1,2-trimethylpropyl)silyl]-D-glucopranosyl]-D-glucopyranose 2,3,4-tri-O-benzoate: theoretical m/z=1762 (M+H⁺); and 74b. a 5mer (n=3): 1-O-β-[2-(2-benzyloxyethoxy)ethoxy]-6-O-[(2,3,4-tri-O-benzoyl)-1-[O-β-(2,3,4-tri-O-benzoyl)-D-glucopranosyl-(1,6)]₃-6-O-[dimethyl(1,1,2-trimethylpropyl)silyl]-D-glucopranosyl]-D-glucopyranose 2,3,4-tri-O-benzoate: theoretical m/z=2730 (M+H⁺).

Example 30

General Desilylation Procedure (formula 75)

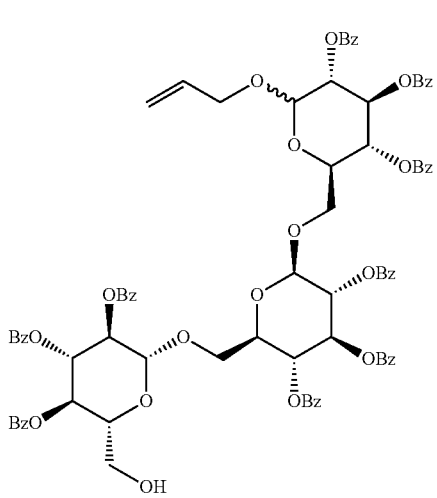

A solution of 1-O-(2-propen-1-yl)-6-O—[O-β-(2,3,4-tri-O-benzoyl)-6-O—[O-β-(2,3,4-tri-O-benzoyl)-6-[dimethyl(1,1,2-trimethylpropyl)silyl]-D-glucopranosyl]-D-glucopranosyl]-D-glucopyranose 2,3,4-tri-O-benzoate (5.3 g, 3.3 mmol) in anhydrous methylene chloride (11 mL) and anhydrous methanol (5.5 mL) was cooled to 0° C. and then treated dropwise with BF₃.OEt₂ (0.4 mL, 3.3 mmol, 1.0 equiv). After the addition was complete, the reaction mixture was warmed to room temperature. After stirring overnight the reaction mixture was quenched with triethylamine (1.3 mL, 9.9 mmol, 3.0 equiv). The reaction mixture was then washed with satd. aq. NaCl (10 mL) and the aqueous layer was washed with methylene chloride (2×20 mL). The combined organic layers were dried (NaSO₄) and the solvent was removed in vacuo. The product was purified by flash chromatography (10× silica, 0-40% ethyl acetate/hexanes) to afford the product (3.55 g) as a solid: m/z=1481 (M+H⁺); 1498 (M+NH₄⁺); 1503 (M+Na⁺).

Similarly prepared by the method of this example are:

(formula 76)

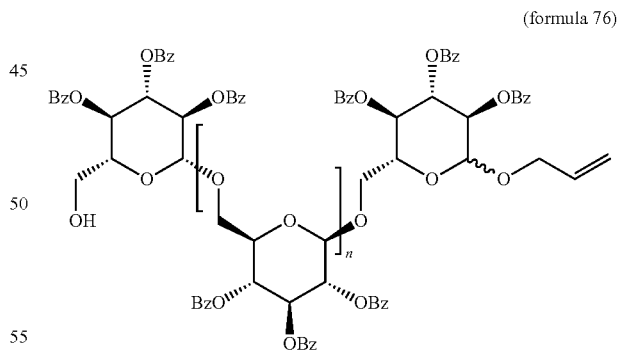

76a. 5mer (n=3): 1-O-(2-propen-1-yl)-6-O-[1-O-β-[O-β-(2,3,4-tri-O-benzoyl)-D-glucopranosyl-(1,6)]₃(2,3,4-tri-O-benzoyl)-6-hydroxy-D-glucopranosyl]-D-glucopyranose 2,3,4-tri-O-benzoate: theoretical m/z=2449 (M+H⁺).

Example 31

Deallylation of Silyl Intermediate

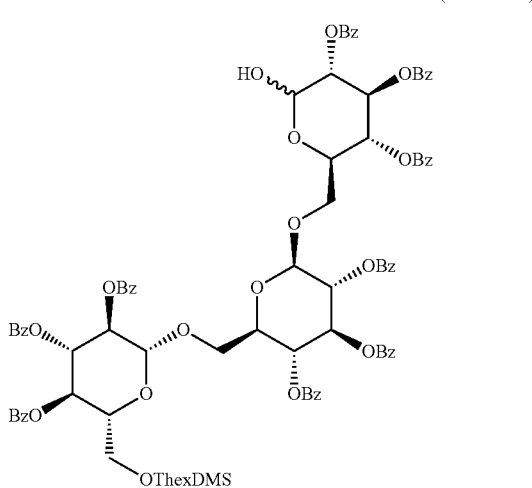
(formula 77)

The solution of 1-O-(2-propen-1-yl)-6-O-[1-O-β-[O-β-(2,3,4-tri-O-benzoyl)-D-glucopranosyl]-(2,3,4-tri-O-benzoyl)-6-O-[dimethyl(1,1,2-trimethylpropyl)silyl]-D-glucopranosyl]-D-glucopyranose 2,3,4-tri-O-benzoate (50 mg, 0.0308 mmol) in acetic acid (2 mL) was degassed with $N_2$ for 15 min. The mixture was then treated with $Pd(PPh_3)_4$ (11 mg, 0.0092 mmol) and the whole reaction system was degassed with $N_2$ for an additional 15 min. The reaction mixture was stirred under $N_2$ at 80° C. for 2 h. The reaction solvent was removed under vacuum via a rotavapor and the mixture was then co-evaporated with toluene (1 mL×2) twice. The residue was purified by silica gel (4 g) flash chromatography (eluent: Ethyl acetate/Hexane, 0 to 40%) to afford product (39 mg) as a solid: m/z=1584 (M+H$^+$); 1600 (M+NH$_4^+$); 1605 (M+Na$^+$).

Similarly prepared by the method of this example are:

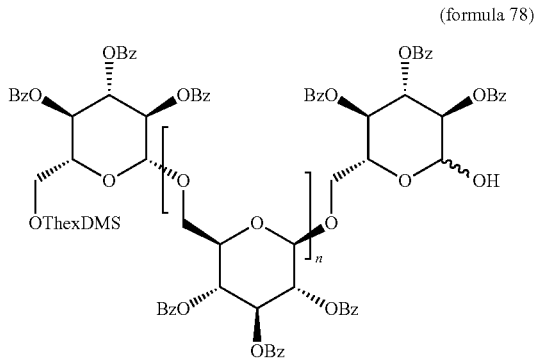
(formula 78)

68a. A 5mer (n=3): 6-O-[[1-O-β-[O-β-(2,3,4-tri-O-benzoyl)-D-glucopranosyl-(1,6)]$_3$-(2,3,4-tri-O-benzoyl)-6-O-[dimethyl(1,1,2-trimethylpropyl)silyl]-D-glucopranosyl]-D-glucopyranose 2,3,4-tri-O-benzoate: theoretical m/z=2552 (M+H$^+$);

Example 32

General Procedure for De-allylation

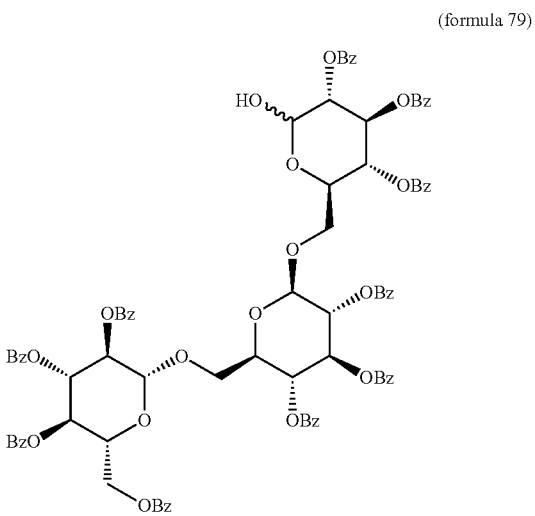
(formula 79)

A solution 1-O-(2-propen-1-yl)-6-O—[O-β-(2,3,4-tri-O-benzoyl)-6-O—[(O-β-(2,3,4,6-tetra-O-benzoyl)-D-glucopranosyl)-D-glucopranosyl]-D-glucopyranose-2,3,4-tri-O-benzoate (1.0 g, 0.63 mmol) in anhydrous degassed dioxane (6.3 mL) and anhydrous degassed methanol (6.3 mL) was treated with $PdCl_2$ (22 mg, 0.13 mmol, 0.2 equiv). After stirring overnight, the reaction mixture was filtered through celite 545 and the solvent was removed in vacuo. The product was purified by flash chromatography (10× silica, 0-40% ethyl acetate/hexanes) to afford the product (0.82 g) as a white solid: m/z=1545 (M+H$^+$); 1562 (M+NH$_4^+$); 1567 (M+Na$^+$).

Similarly prepared by the method of this example were:

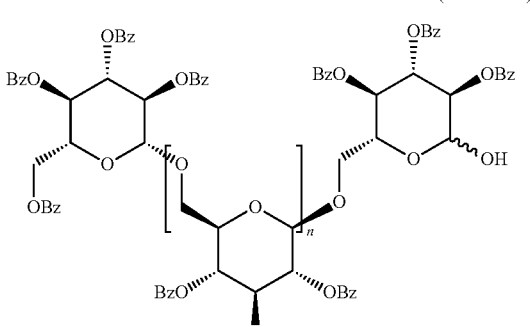
(formula 80)

n=1, 3

80a. a 3mer (n=1): 6-O-[1-[O-β (2,3,4-tri-O-benzoyl)-D-glucopranosyl]$_3$ (O-β-(2,3,4,6-tetra-O-benzoyl)-D-glucopranosyl]-D-glucopyranose-2,3,4-tri-O-benzoate:
m/z=1248 ((M+2H$^+$)/2); 1256 ((M+NH$_4$+H$^+$)/2); 1259 ((M+Na$^+$+H$^+$)/2); and 80b. a 5mer (n=3): 6-O-[1-[O-β (2,3,4-tri-O-benzoyl)-D-glucopranosyl]$_5$ (O-β-(2,3,4,6-tetra-O-benzoyl)-D-glucopranosyl]-D-glucopyranose-2,3,4-tri-O-benzoate:
m/z=1722 ((M+2H$^+$)/2); 1730 ((M+NH$_4$+H$^+$)/2); 1733 ((M+Na$^+$+H$^+$)/2).

Example 33

De-benzylation

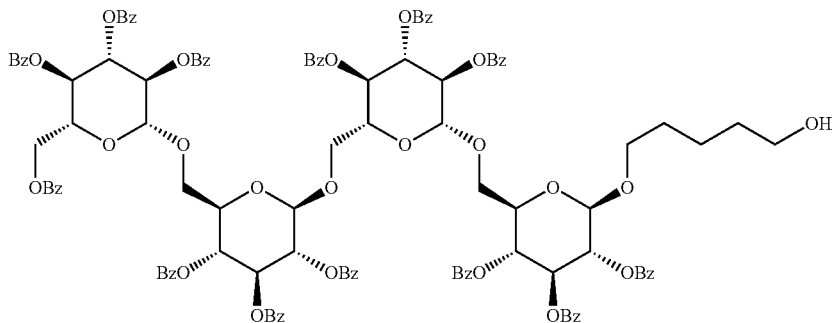

(formula 81)

A solution of 1-O-β-(5-benzyloxypentoxy)-6-O-[1-[O-β-(2,3,4-tri-O-benzoyl)-D-glucopranosyl]$_2$-O-β-(2,3,4,6-tetra-O-benzoyl)-D-glucopranosyl]-D-glucopyranose-2,3,4-tri-O-benzoate (1.0 g g, 0.4557 mmol) in ethyl acetate (4.6 mL) was degassed with H$_2$ for 15 min. The mixture was then treated with Pd/C (0.10 g, 10 wt. % loading) and the whole reaction system was degassed with H$_2$ for 15 min. The reaction mixture was stirred under H$_2$ with balloon pressure at room temperature for 20 h. The reaction was filtered through a Celite pad and washed with ethyl acetate. The filtrate was evaporated under vacuum with rotavapor and the residue was purified by silica gel (25 g) flash chromatography (0-45% ethyl acetate/hexane) to afford the product (0.71 g) as a solid: m/z=1054 ((M+2H$^+$)/2); 1062 ((M+NH$_4$+H$^+$)/2); 1065 ((M+Na$^+$+H$^+$)/2).

Similarly prepared by the method of this example were:

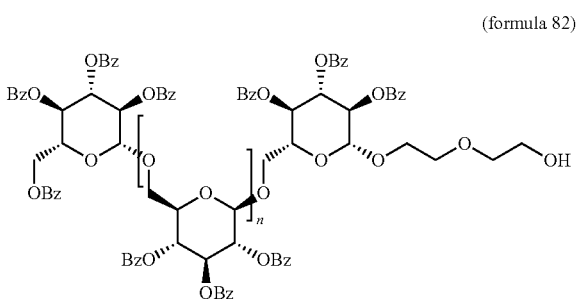

(formula 82)

82a. a 4mer (n=2): 1-O-β-[2-(2-benzyloxyethoxy)ethoxy]-6-O-[1-[O-β (2,3,4-tri-O-benzoyl)-D-glucopranosyl]$_2$-O-β-(2,3,4,6-tetra-O-benzoyl)-D-glucopranosyl]-D-glucopyranose-2,3,4-tri-O-benzoate: m/z=1055 ((M+2H$^+$)/2); 1063 ((M+NH$_4$+H$^+$)/2); 1066 ((M+Na$^+$+H$^+$)/2);

Example 34

Oxidation to Aldehyde

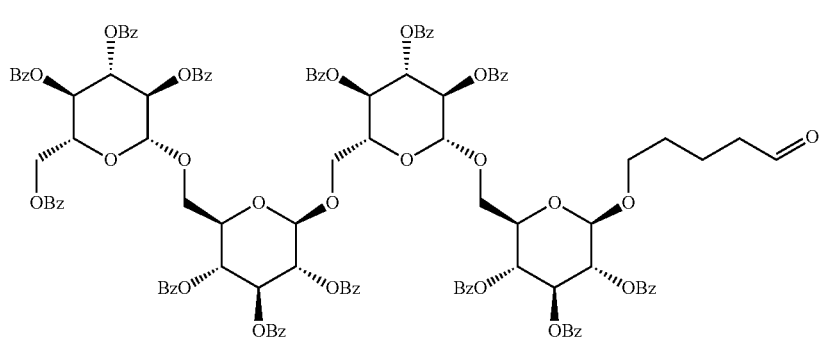

(formula 83)

A solution of 1-O-β-(5-hydroxypentoxy)-6-O-[1-[O-β-(2,3,4-tri-O-benzoyl)-D-glucopranosyl]₂-O-β-(2,3,4,6-tetra-O-benzoyl)-D-glucopranosyl]-D-glucopyranose-2,3,4-tri-O-benzoate (680 mg, 0.3229 mmol) in dichloromethane (6.0 mL). was treated with Dess-Martin Periodinane (156 mg, 0.3555 mmol) and left stirring under $N_2$ at room temperature for 5 h. The filtrate was evaporated under vacuum with rotavapor and the residue was purified by silica gel (25 g) flash chromatography (eluent: Ethyl acetate/Hexane, 0 to 30%) to afford product (490 mg) as a solid: m/z=1053 ((M+2H$^+$)/2); 1061 ((M+NH$_4$+H$^+$)/2); 1064 ((M+Na$^+$+H$^+$)/2).

Similarly prepared by the method of this example were:

A solution of 1-O-β-(4-oxybutoxy)-6-O-[1-[O-β (2,3,4-tri-O-benzoyl)-D-glucopranosyl]₂-O-β-(2,3,4,6-tetra-O-benzoyl)-D-glucopranosyl]-D-glucopyranose-2,3,4-tri-O-benzoate (200 mg, 0.0.0950 mmol in DCM (4.6 mL) was successively treated with N,N-Diphenylethylenediamine (24 mg, 0.1140 mmol) and then (+)-Camphor-10-sulfonic acid (2.2 mg, 0.0095 mmol). The reaction mixture was stirred under $N_2$ at room temperature for 12 h. The reaction solvent was evaporated under vacuum with rotavapor and the residue was purified by silica gel (25 g, deactivated by 0.1% NEt$_3$ in Hexane)) flash chromatography (eluent: Ethyl acetate/Hexane, 0 to 50%) to afford product (147 mg) as a solid: m/z=1150 ((M+2H$^+$)/2); 1158 ((M+NH$_4$+H$^+$)/2); 1161 ((M+Na$^+$+H$^+$)/2);

Similarly prepared by the method of this example were:

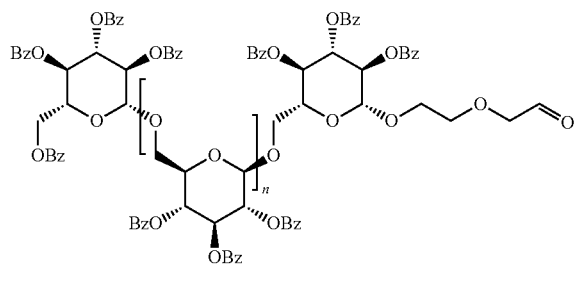

(formula 84)

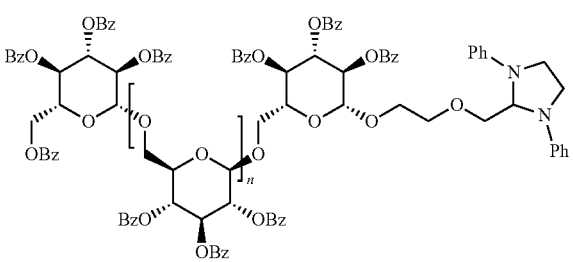

(formula 86)

84a. a 4mer (n=2): 1-O-β-[2-(2-oxymethoxy)ethoxy]-6-O-[1-[O-β-(2,3,4-tri-O-benzoyl)-D-glucopranosyl-(1,6)]₂-O-β-(2,3,4,6-tetra-O-benzoyl)-D-glucopranosyl]-D-glucopyranose-2,3,4-tri-O-benzoate: m/z=1054 ((M+2H$^+$)/2); 1062 ((M+NH$_4$+H$^+$)/2); 1065 ((M+Na$^+$+H$^+$)/2);

Example 35

Aldehyde Protection 86a. a 4mer (n=2): 1-O-β-[2-[(1,3-diphenylimidazolidin-2-yl)methoxy]ethoxy]-6-O-[1-[O-β (2,3,4-tri-O-benzoyl)-D-glucopranosyl-(1,6)]₂-O-β-(2,3,4,6-tetra-O-benzoyl)-D-glucopranosyl]-D-glucopyranose-2,3,4-tri-O-benzoate): m/z=1151 ((M+2H$^+$)/2); 1159 ((M+NH$_4$+H$^+$)/2); 1162 ((M+Na$^+$+H$^+$)/2);

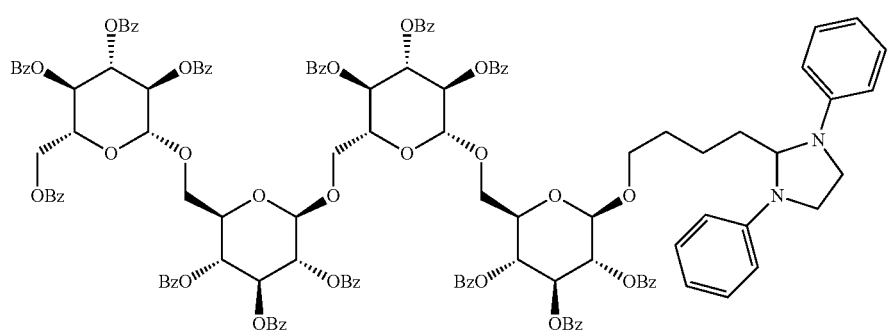

(formula 85)

Example 36

General Procedure for De-benzoylation

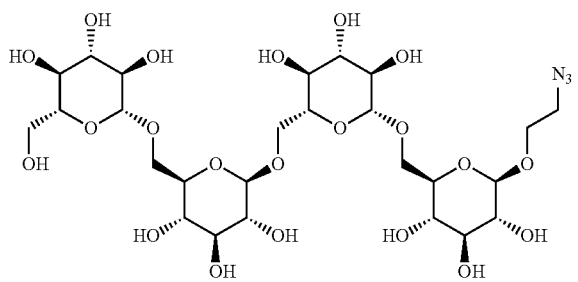

(formula 87)

A solution of 1-O-(2-azidoethyl)-6-O—[O-β (2,3,4-tri-O-benzoyl)-D-glucopranosyl-(1,6)]$_3$-β-D-glucopyranose 2,3,4,6-tetra-O-benzoate (0.7 g, 0.34 mmol) in THF (1.7 mL) and methanol (1.7 mL) was treated with NaOMe in methanol (25%, 36 µL, 0.16 mmol, 0.5 equiv). After stirring overnight, a white ppt formed indicating the formation of the sugar. The reaction mixture was dried and then triturated with ethyl acetate (2×5.0 mL) followed by purification via HPLC on an Agilent Polaris A column (10×250 mm, 1-95% Water/Acetonitrile w/ 0.1% formic acid) to afford the product, 1-O-(2-azidoethyl)-6-[O-β-D-glucopyranosyl-(1,6)]$_3$-β-D-glucopyranoside, 0.2 g: m/z=736 (M+H$^+$); 753 (M+NH$_4^+$); 758 (M+Na$^+$).

Similarly prepared by the method of this example were the following compounds.

a. Compounds of Formula 88

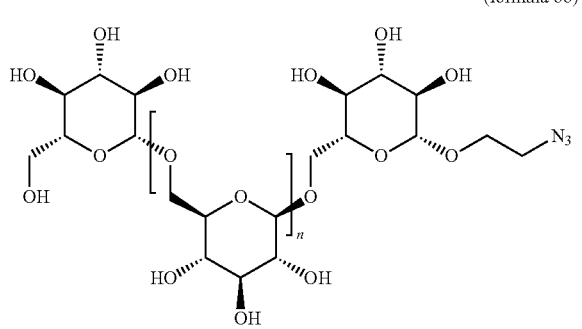

(formula 88)

88a. a 3mer (n=1): 1-O-(2-azidoethyl)-6-O—[O-β-D-glucopyranosyl-(1,6)]$_2$-β-D-glucopyranoside: m/z=574 (M+H$^+$); 591 (M+NH$_4^+$); 596 (M+Na$^+$);

88b. a 5mer (n=3): 1-O-(2-azidoethyl)-6-O—[O-β-D-glucopyranosyl-(1,6)]$_4$-β-D-glucopyranoside: m/z=898 (M+H$^+$); 915 (M+NH$_4^+$); 920 (M+Na$^+$); and 88c. a 6mer (n=4): 1-O-(2-azidoethyl)-6-O—[O-β-D-glucopyranosyl-(1,6)]$_5$-β-D-glucopyranoside: m/z=1060 (M+H$^+$); 1077 (M+NH$_4^+$); 1082 (M+Na$^+$).

b. Compounds of Formula 89

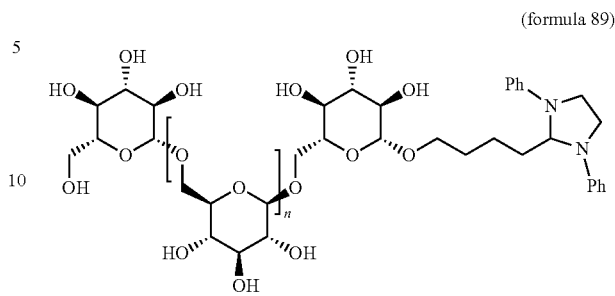

(formula 89)

89a. a 4mer (n=2): 1-O-[4-(1,3-diphenylimidazolidin-2-yl)pentoxy]-6-O—[O-β-D-glucopyranosyl-(1,6)]$_3$-β-D-glucopyranoside: m/z=944 (M+H$^+$); 961 (M+NH$_4^+$); 966 (M+Na$^+$).

and c. Compounds of Formula 90

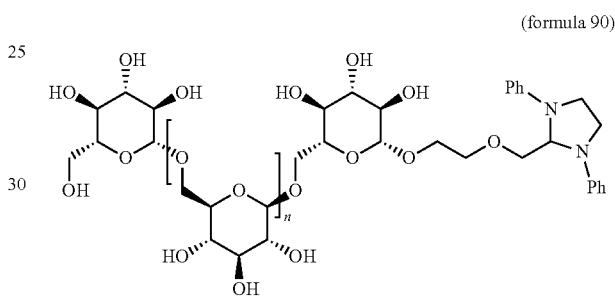

(formula 90)

90a. a 4mer (n=2): 1-O-[2-[(1,3-diphenylimidazolidin-2-yl)methoxy]ethoxy]-6-O—[O-β-D-glucopyranosyl-(1,6)]$_3$-β-D-glucopyranoside: m/z=946 (M+H$^+$); 963 (M+NH$_4^+$); 968 (M+Na$^+$).

The following compounds can be similarly prepared by the method of this example.

a. Compounds of Formula 9a

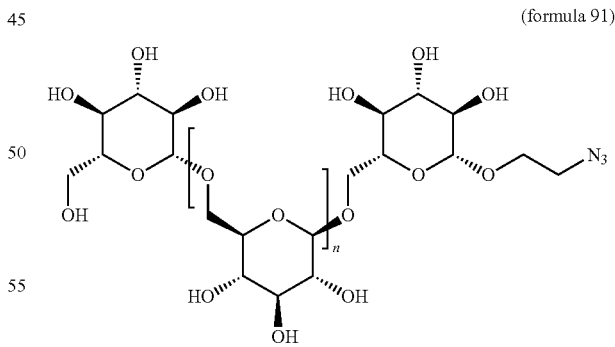

(formula 91)

91a. a 7mer (n=5): 1-O-(2-azidoethyl)-6-O—[O-β-D-glucopyranosyl-(1,6)]$_6$-β-D-glucopyranoside: theoretical m/z=1222 (M+H$^+$);

91b. an 8mer (n=6): 1-O-(2-azidoethyl)-6-O—[O-β-D-glucopyranosyl-(1,6)]$_7$-β-D-glucopyranoside theoretical m/z=1384 (M+H$^+$); and 91c. a 9mer (n=7): 1-O-(2-azidoethyl)-6-O—[O-β-D-glucopyranosyl-(1,6)]$_8$-β-D-glucopyranoside: theoretical m/z=1546 (M+H$^+$),

Example 37

Aldehyde Deprotection

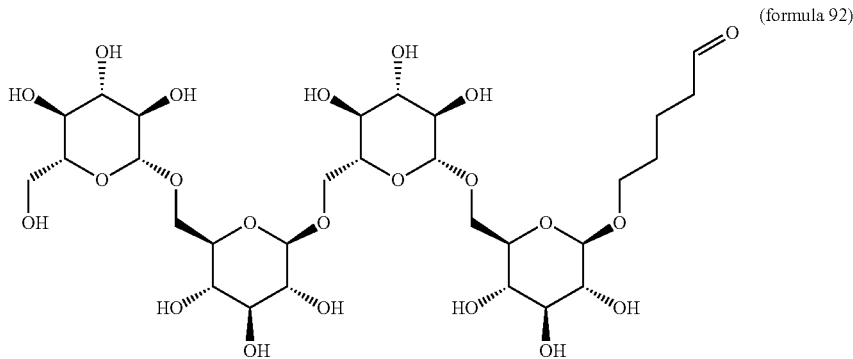 [SMILES: O=CCCCCO[C@@H]1O[C@H](CO[C@@H]2O[C@H](CO[C@@H]3O[C@H](CO[C@@H]4O[C@H](CO)[C@@H](O)[C@H](O)[C@H]4O)[C@@H](O)[C@H](O)[C@H]3O)[C@@H](O)[C@H](O)[C@H]2O)[C@@H](O)[C@H](O)[C@H]1O]
(formula 92)

A solution of 1-O-[4-(1,3-diphenylimidazolidin-2-yl)butoxy]-6-[O-β-D-glucopyranosyl-(1,6)]$_3$-β-D-glucopyranoside (10 mg, 0.0106 mmol) was dissolved in 1% of acetic acid in the mixture of water (0.2 mL)/MeCN (0.2 mL). The reaction mixture was stirred at 50° C. for 2 h. The reaction was purified via HPLC on an Agilent Polaris A column (10×250 mm, 1-95% water/acetonitrile w/ 0.1% formic acid) to afford product, 1-O-[4-oxybutoxy]-6-O—[O-β-D-glucopyranosyl-(1,6)]$_3$-β-D-glucopyranoside (4.1 mg) as a white solid: m/z=751 (M+H$^+$); 769 (M+NH$_4^+$); 774 (M+Na$^+$).

Similarly prepared by the method of this example were:

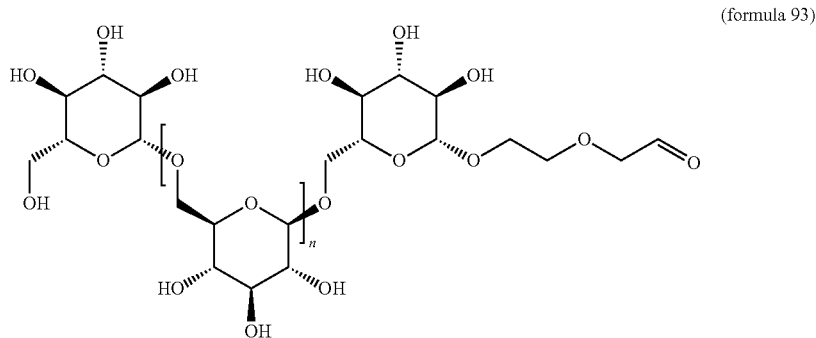
(formula 93)

93a. a 4mer (n=2): 1-O-[2-(2-oxymethoxy)ethoxy]-6-O—[O-β-D-glucopyranosyl-(1,6)]$_3$-β-D-glucopyranoside: m/z=946 (M+H$^+$); 963 (M+NH$_4^+$); 968 (M+Na$^+$)

The following compounds can be similarly prepared by the method of this example.

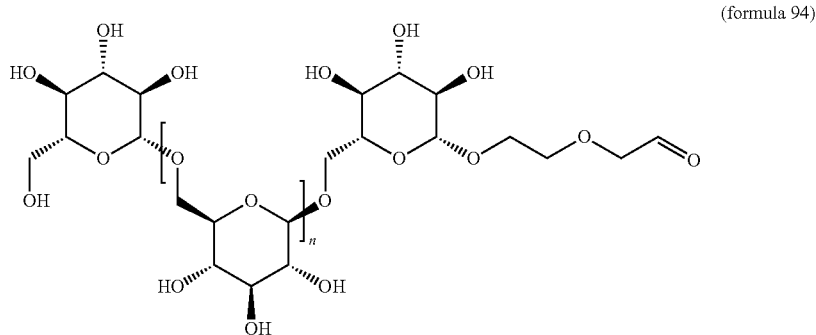
(formula 94)

94a. a 3mer (n=1): 1-O-[4-oxypentoxy]-6-O—[O-β-D-glu-copyranosyl-(1,6)]$_2$-β-D-glucopyranoside: theoretical m/z=589 (M+H$^+$);

94b. a 5mer (n=3): 1-O-[4-oxypentoxy]-6-O—[O-β-D-glu-copyranosyl-(1,6)]$_4$-β-D-glucopyranoside: theoretical m/z=913 (M+H$^+$);

94c. a timer (n=4): 1-O-[4-oxypentoxy]-6-O—[O-β-D-glu-copyranosyl-(1,6)]$_5$-β-D-glucopyranoside: theoretical m/z=1075 (M+H$^+$);

94d. a 7mer (n=5): 1-O-[4-oxypentoxy]-6-O—[O-β-D-glu-copyranosyl-(1,6)]$_6$-β-D-glucopyranoside: theoretical m/z=1237 (M+H$^+$);

94e. an 8mer (n=5): 1-O-[4-oxypentoxy]-6-O—[O-β-D-glu-copyranosyl-(1,6)]$_7$-β-D-glucopyranoside: theoretical m/z=1399 (M+H$^+$); and 94f. a 9mer (n=7): 1-O-[4-oxypentoxy]-6-O—[O-β-D-glu-copyranosyl-(1,6)]$_8$-β-D-glucopyranoside: theoretical m/z=1561 (M+H$^+$).

b. Compounds of Formula 95

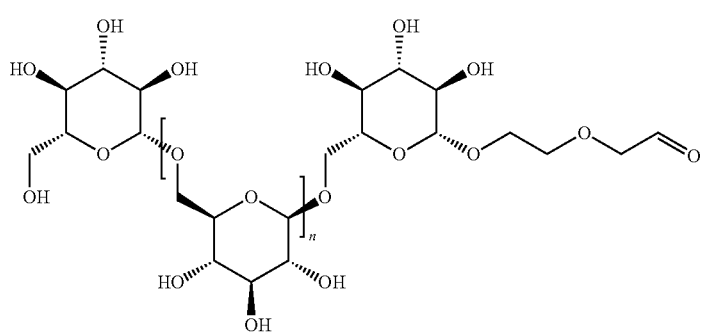

(formula 95)

95a. a 3mer (n=1): 1-O-[2-(2-oxymethoxy)ethoxy]-6-O—[O-β-D-glucopyranosyl-(1,6)]$_2$-β-D-glucopyranoside: theoretical m/z=784 (M+H$^+$);

95b. a 5mer (n=3): 1-O-[2-(2-oxymethoxy)ethoxy]-6-O—[O-β-D-glucopyranosyl-(1,6)]$_4$-β-D-glucopyranoside: theoretical m/z=1108 (M+H$^+$);

95c. a timer (n=4): 1-O-[2-(2-oxymethoxy)ethoxy]-6-O—[O-β-D-glucopyranosyl-(1,6)]$_5$-β-D-glucopyranoside: theoretical m/z=1270 (M+H$^+$);

95d. a 7mer (n=5): 1-O-[2-(2-oxymethoxy)ethoxy]-6-O—[O-β-D-glucopyranosyl-(1,6)]$_6$-β-D-glucopyranoside: theoretical m/z=1432 (M+H$^+$);

95e. an 8mer (n=6): 1-O-[2-(2-oxymethoxy)ethoxy]-6-O—[O-β-D-glucopyranosyl-(1,6)]$_7$-β-D-glucopyranoside: theoretical m/z=1594 (M+H$^+$); and 95f. a 9mer (n=7): 1-O-[2-(2-oxymethoxy)ethoxy]-6-O—[O-β-D-glucopyranosyl-(1,6)]$_8$-β-D-glucopyranoside: theoretical m/z=1756 (M+H$^+$).

Example 38

Dendrimer 3,5-bis(1-[2-[O-β-D-glucopyranosyl-(1→6)-O-β-D-glucopyranosyl-(1→6)-O-β-D-glucopyranosyl-(1→6)-α-D-glucopyranosyl]oxy]ethyl-1H-1,2,3-triazol-4-yl)methoxybenzoic acid

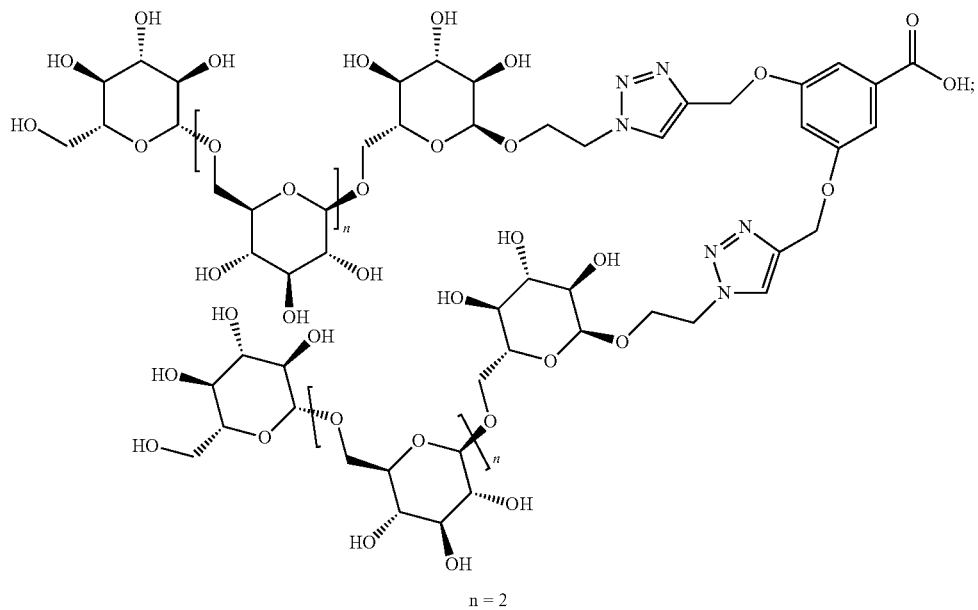

(formula 96)

n = 2

A solution of methyl 3,5-bis(prop-2-ynoxy)benzoate (0.8 mg, 3.2 μmol) and 1-O-(2-azidoethyl)-6-[O-β-D-glucopyranosyl-1,6]$_3$-α-D-glucopyranoside (5.0 mg, 7.0 μmol) were combined in anhydrous DMF (30 μL) at 23° C. and copper (I) iodide (0.6 mg, 3.2 μmol, 1.0 equiv) and DIPEA (1.4 μL, 8.0 μmol, 2.5 equiv) were added sequentially. The resultant mixture was heated at 35° C. After 18.5 hours, the reaction mixture was dried in vacuo, diluted with water (30 μL) and treated to NaOH (10.0 M (aq), 3.2 uL, 3.2 μmol, 10.0 equiv) at 0° C. Stirring was maintained at 0° C. for 10 min, then at 23° C. for 1.5 hours. Purification by HPLC via an Agilent Polaris A column (10×250 mm, 1-95% water/acetonitrile w/ 0.1% formic acid) and subsequent lyophilization yielded 2.2 mg of the desired product as a white solid: m/z=1701 (M+H$^+$); 1718 (M+NH$_4^+$); 1723 (M+Na$^+$)

Similarly prepared by the method of this example were:
a. Compounds of Formula 97
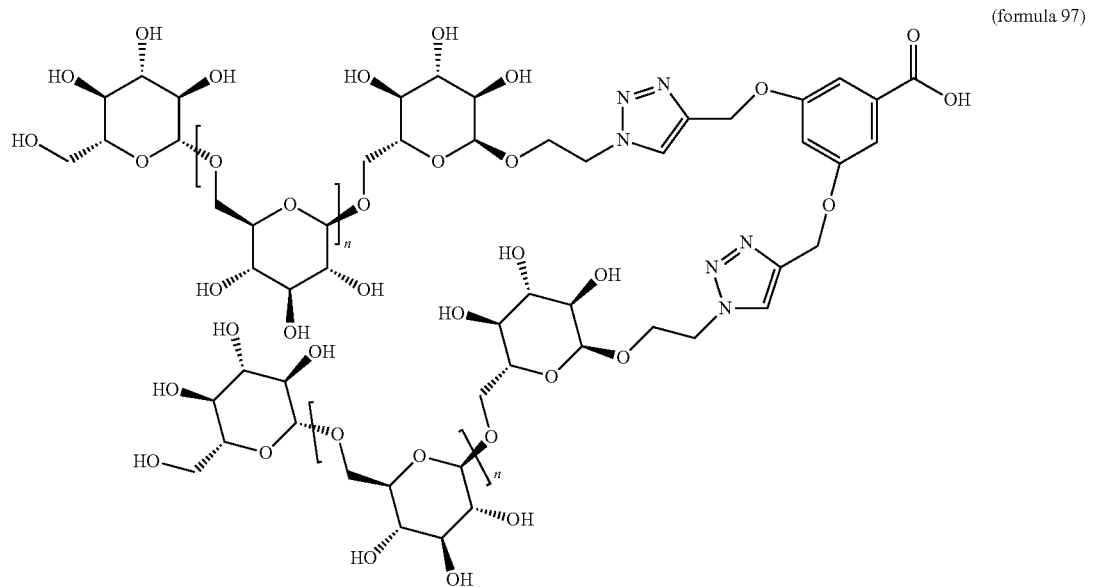
(formula 97)
97a. a 3mer (n=1): 3,5-bis(1[2-[O-β-D-glucopyranosyl-(1→6)-O-β-D-glucopyranosyl-(1→6)-α-D-glucopyranosyl]oxy]ethyl-1H-1,2,3-triazol-4-yl)methoxybenzoic acid: m/z=1377 (M+H$^+$); 1394 (M+NH$_4^+$); 1399 (M+Na$^+$).
b. Compounds of Formula 98
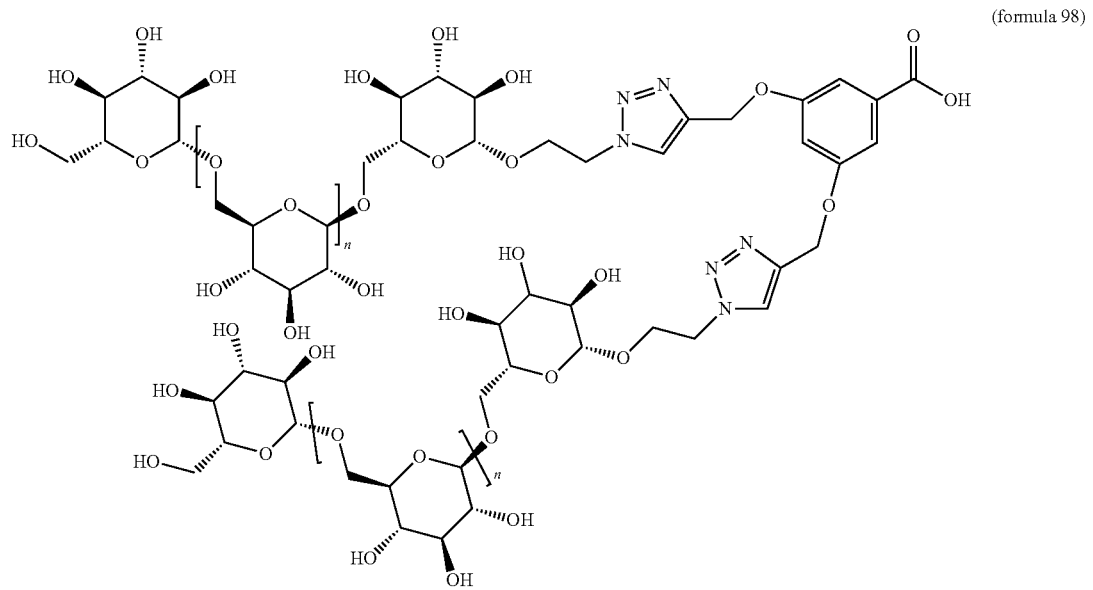
(formula 98)

98a. a 4mer (n=2): 3,5-bis(1[2-[O-β-D-glucopyranosyl-(1→6)]₄oxy]ethyl-1H-1,2,3-triazol-4-yl)methoxybenzoic acid: m/z=1701 (M+H⁺); 1718 (M+NH₄⁺); 1723 (M+Na⁺)

98b. a 5mer (n=3): 3,5-bis(1[2-[O-β-D-glucopyranosyl-(1→6)]₅oxy]ethyl-1H-1,2,3-triazol-4-yl)methoxybenzoic acid: m/z=1013 ((M+2H⁺)/2); 1021 ((M+NH₄+H⁺)/2); 1024 ((M+Na⁺+H⁺)/2);

98c. a timer (n=4): 3,5-bis(1[2-[O-β-D-glucopyranosyl-(1→6)]₆oxy]ethyl-1H-1,2,3-triazol-4-yl)methoxybenzoic acid: m/z=1175 ((M+2H⁺)/2); 1183 ((M+NH₄+H⁺)/2); 1186 ((M+Na⁺+H⁺)/2);

The following compounds can be similarly prepared by the method of this example.

a. Compounds of Formula 99

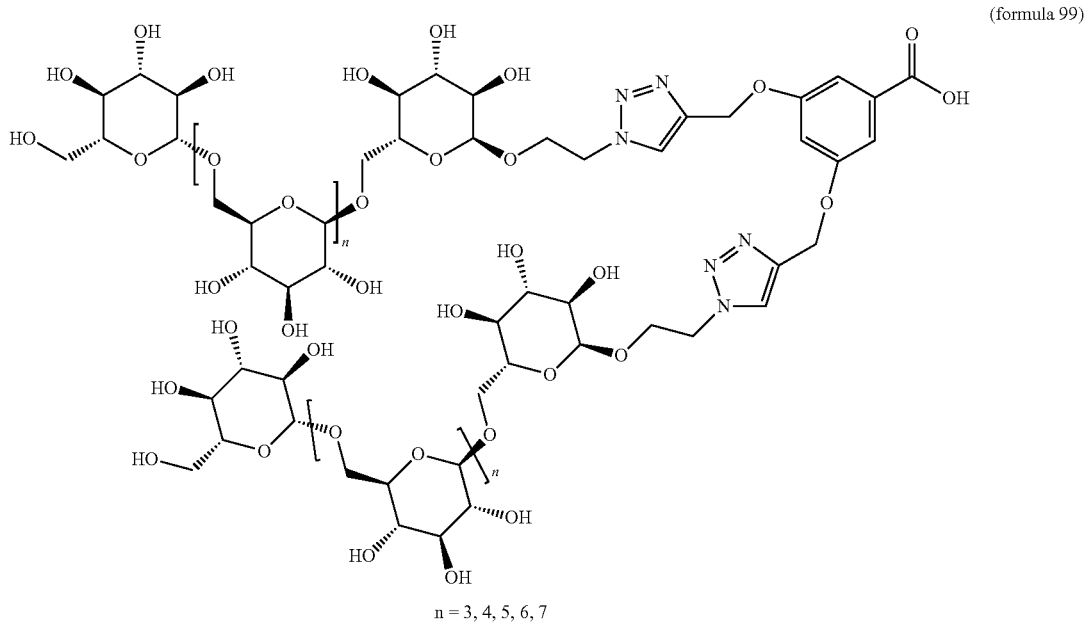

(formula 99)

n = 3, 4, 5, 6, 7

99a. a 5mer (n=3): 3,5-bis(1-[2-[O-β-D-glucopyranosyl-(1→6)-O-β-D-glucopyranosyl-(1→6)-O-β-D-glucopyranosyl-(1→6)-O-β-D-glucopyranosyl-(1→6)-α-D-glucopyranosyl]oxy]ethyl-1H-1,2,3-triazol-4-yl) methoxybenzoic acid: theoretical m/z=2025 (M+H⁺);

99b. a timer (n=4): 3,5-bis(1-[2-[O-β-D-glucopyranosyl-(1→6)-O-β-D-glucopyranosyl-(1→6)-O-β-D-glucopyranosyl-(1→6)-O-β-D-glucopyranosyl-(1→6)-O-β-D-glucopyranosyl-(1→6)-α-D-glucopyranosyl]oxy]ethyl-1H-1,2,3-triazol-4-yl)methoxybenzoic acid: theoretical m/z=2349 (M+H⁺);

99c. a 7mer (n=5): 3,5-bis(1-[2-[O-β-D-glucopyranosyl-(1→6)-O-β-D-glucopyranosyl-(1→6)-O-β-D-glucopyranosyl-(1→6)-O-β-D-glucopyranosyl-(1→6)-O-β-D-glucopyranosyl-(1→6)-O-β-D-glucopyranosyl-(1→6)-α-D-glucopyranosyl]oxy]ethyl-1H-1,2,3-triazol-4-yl) methoxybenzoic acid: theoretical m/z=2673 (M+H⁺);

99d. an 8mer (n=6): 3,5-bis(1-[2-[O-β-D-glucopyranosyl-(1→6)-O-β-D-glucopyranosyl-(1→6)-O-β-D-glucopyranosyl-(1→6)-O-β-D-glucopyranosyl-(1→6)-O-β-D-glucopyranosyl-(1→6)-O-β-D-glucopyranosyl-(1→6)-O-β-D-glucopyranosyl-(1→6)-α-D-glucopyranosyl]oxy] ethyl-1H-1,2,3-triazol-4-yl)methoxybenzoic acid: theoretical m/z=2997 (M+H⁺); and 99e. a 9mer (n=7): 3,5-bis(1-[2-[O-β-D-glucopyranosyl-(1→6)-O-β-D-glucopyranosyl-(1→6)-O-β-D-glucopyranosyl-(1→6)-O-β-D-glucopyranosyl-(1→6)-O-β-D-glucopyranosyl-(1→6)-O-β-D-glucopyranosyl-(1→6)-O-β-D-glucopyranosyl-(1→6)-O-β-D-glucopyranosyl-(1→6)-α-D-glucopyranosyl]oxy]ethyl-1H-1,2,3-triazol-4-yl)methoxybenzoic acid: theoretical m/z=3321 (M+H⁺).

b. Compounds of Formula 100

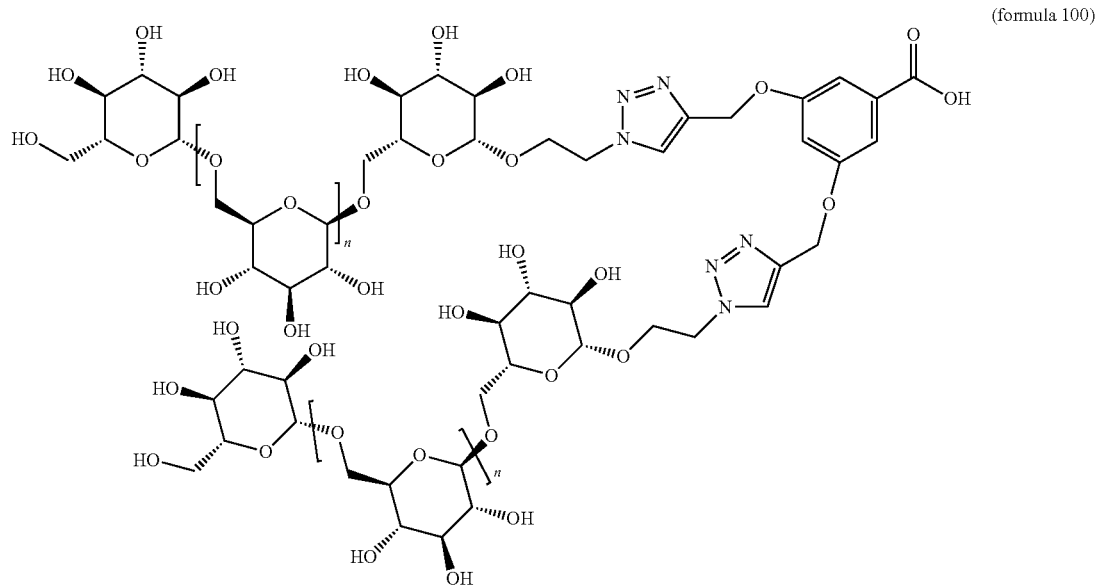

(formula 100)

100a. a 3mer (n=1): 3,5-bis(1[2-[O-β-D-glucopyranosyl-(1→6)]$_3$oxy]ethyl-1H-1,2,3-triazol-4-yl)methoxybenzoic acid: theoretical m/z=1377 (M+H$^+$);

100b. a 7mer (n=5): 3,5-bis(1[2-[O-β-D-glucopyranosyl-(1→6)]$_7$oxy]ethyl-1H-1,2,3-triazol-4-yl)methoxybenzoic acid: theoretical m/z=2673 (M+H$^+$);

100c. an 8mer (n=6): 3,5-bis(1[2-[O-β-D-glucopyranosyl-(1→6)]$_8$oxy]ethyl-1H-1,2,3-triazol-4-yl)methoxybenzoic acid: theoretical m/z=2997 (M+H$^+$); and 100d. a 9mer (n=7): 3,5-bis(1[2-[O-β-D-glucopyranosyl-(1→6)]$_9$oxy]ethyl-1H-1,2,3-triazol-4-yl)methoxybenzoic acid: theoretical m/z=3321 (M+H$^+$).

Example 39

Dendrimer Aldehyde 3,5-bis (1-[2-[O-β-D-glucopyranosyl-(1→6)]$_4$oxy] ethyl-1H-1,2,3-triazol-4-yl)methoxybenzaldehyde

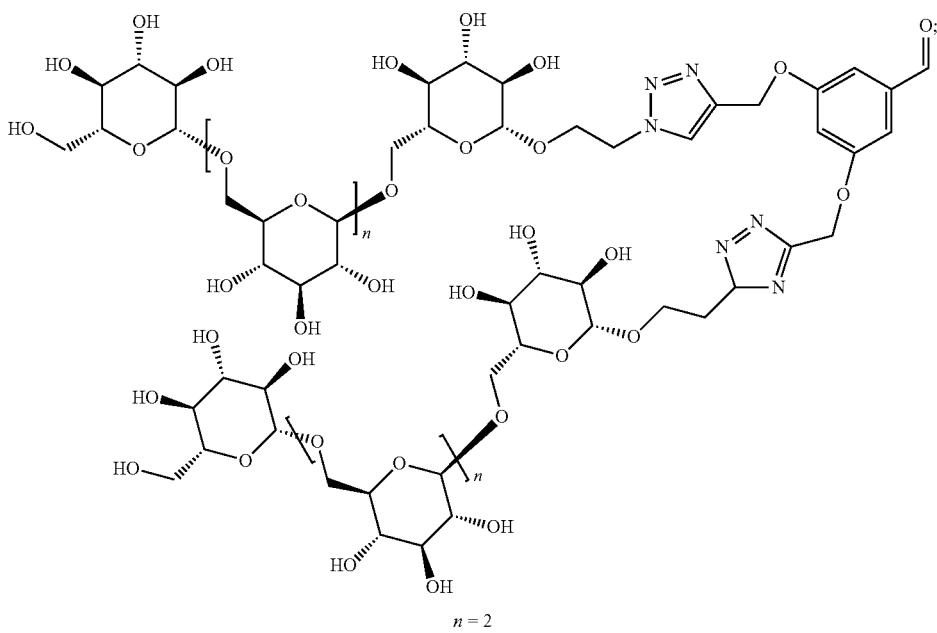

(formula 101)

A solution of methyl 3,5-bis(prop-2-ynoxy)benzaldehyde (0.8 mg, 3.2 μmol) and 1-O-(2-azidoethyl)-6-[O-β-D-glucopyranosyl-1,6]₃-β-D-glucopyranoside (5.0 mg, 7.0 μmol) were combined in anhydrous DMF (30 μL) at 23° C. and copper (I) iodide (0.6 mg, 3.2 μmol, 1.0 equiv) and DIPEA (1.4 μL, 8.0 μmol, 2.5 equiv) were added sequentially. The resultant mixture was heated at 35° C. After 18.5 hours, the reaction mixture was dried in vacuo, diluted with water (30 μL) and treated to NaOH (10.0 M (aq), 3.2 uL, 3.2 μmol, 10.0 equiv) at 0° C. Stirring was maintained at 0° C. for 10 min, then at 23° C. for 1.5 hours. Purification by HPLC via an Agilent Polaris A column (10×250 mm, 1-95% water/acetonitrile w/ 0.1% formic acid) and subsequent lyophilization yielded 2.2 mg of the desired product: m/z=1685 (M+H⁺); 1702 (M+NH₄⁺); 1707 (M+Na⁺).

The below compounds of formula 101 were prepared similarly.

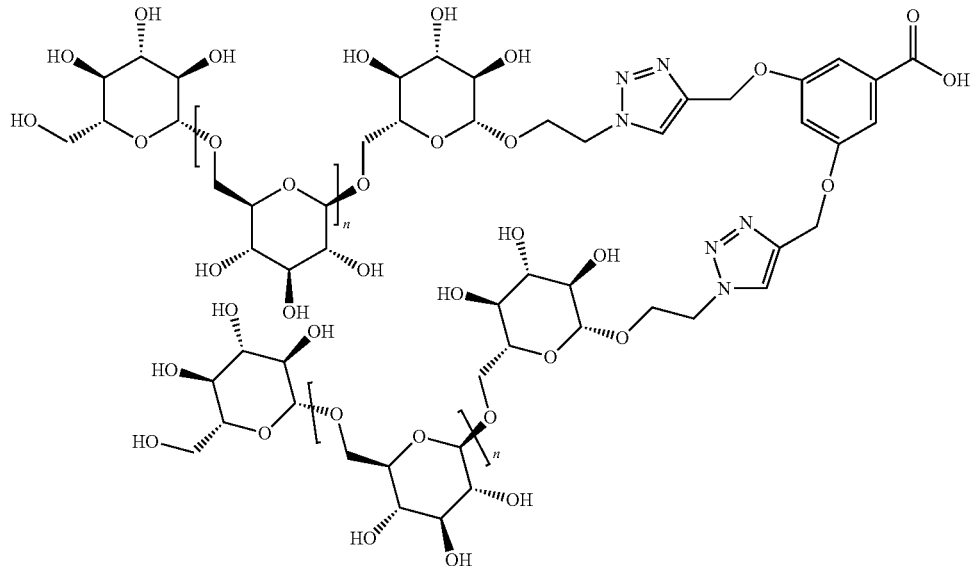

101b. a 5mer (n=3): 3,5-bis(1-[2-[O-β-D-glucopyranosyl-(1→6)]₅oxy]ethyl-1H-1,2,3-triazol-4-yl)methoxybenzaldehyde: m/z=1005 ((M+2H⁺)/2); 1013 ((M+NH₄+H⁺)/2); 1016 ((M+Na⁺+H⁺)/2); and 101c. a 6mer (n=4): 3,5-bis(1-[2-[O-β-D-glucopyranosyl-(1→6)]₆oxy]ethyl-1H-1,2,3-triazol-4-yl)methoxybenzaldehyde: m/z=1167 ((M+2H⁺)/2); 1175 ((M+NH₄+H⁺)/2); 1178 ((M+Na⁺+H⁺)/2).

The following compounds can be similarly prepared by the method of this example.

a. Compounds of Formula 102

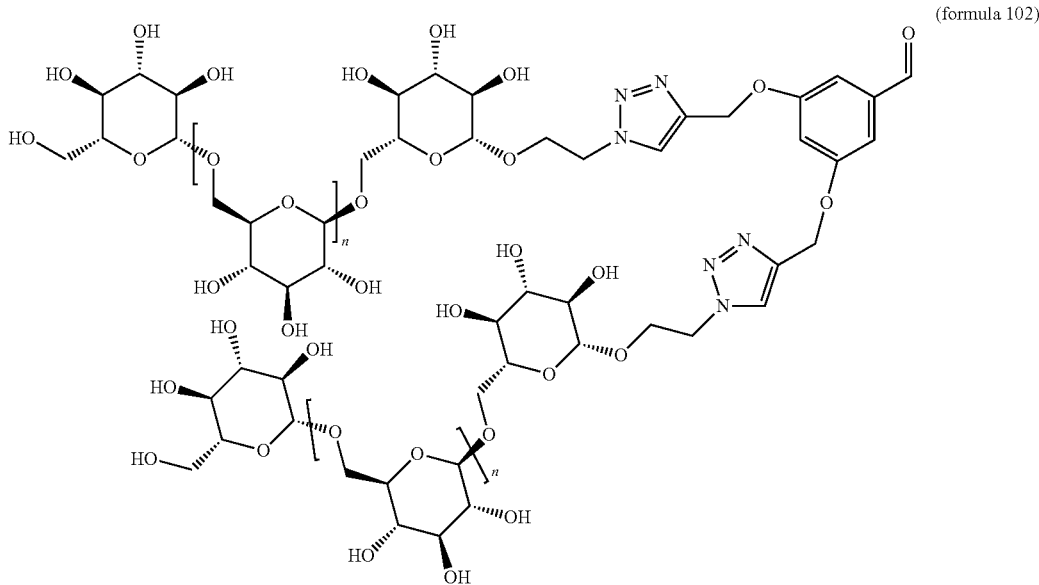

(formula 102)

102a. a 3mer (n=1): 3,5-bis(1-[2-[O-β-D-glucopyranosyl-(1→6)]₃oxy]ethyl-1H-1,2,3-triazol-4-yl)methoxybenzaldehyde: theoretical m/z=1361 (M+H⁺);

102b. a 7mer (n=5): 3,5-bis(1-[2-[O-β-D-glucopyranosyl-(1→6)]₇oxy]ethyl-1H-1,2,3-triazol-4-yl)methoxybenzaldehyde: theoretical m/z=2657 (M+H⁺);

102c. an 8mer (n=6): 3,5-bis(1-[2-[O-β-D-glucopyranosyl-(1→6)]₈oxy]ethyl-1H-1,2,3-triazol-4-yl)methoxybenzaldehyde: theoretical m/z=2981 (M+H⁺); and 102d. a 9mer (n=7): 3,5-bis(1-[2-[O-β-D-glucopyranosyl-(1→6)]₉oxy]ethyl-1H-1,2,3-triazol-4-yl)methoxybenzaldehyde: theoretical m/z=3305 (M+H⁺).

b. Compounds of Formula 103 copyranosyl-(1→6)-α-D-glucopyranosyl]oxy]ethyl-1H-1,2,3-triazol-4-yl) methoxybenzaldehyde: theoretical m/z=2333 (M+H⁺);

103e. a 7mer (n=5): 3,5-bis(1-[2-[O-β-D-glucopyranosyl-(1→6)-O-β-D-glucopyranosyl-(1→6)-O-β-D-glucopyranosyl-(1→6)-O-β-D-glucopyranosyl-(1→6)-O-β-D-glucopyranosyl-(1→6)-O-β-D-glucopyranosyl-(1→6)-α-D-glucopyranosyl]oxy]ethyl-1H-1,2,3-triazol-4-yl) methoxybenzaldehyde: theoretical m/z=2657 (M+H⁺);

103f. an 8mer (n=6): 3,5-bis(1-[2-[O-β-D-glucopyranosyl-(1→6)-O-β-D-glucopyranosyl-(1→6)-O-β-D-glucopyranosyl-(1→6)-O-β-D-glucopyranosyl-(1→6)-O-β-D-glucopyranosyl-(1→6)-O-β-D-glucopyranosyl-(1→6)-O-β-

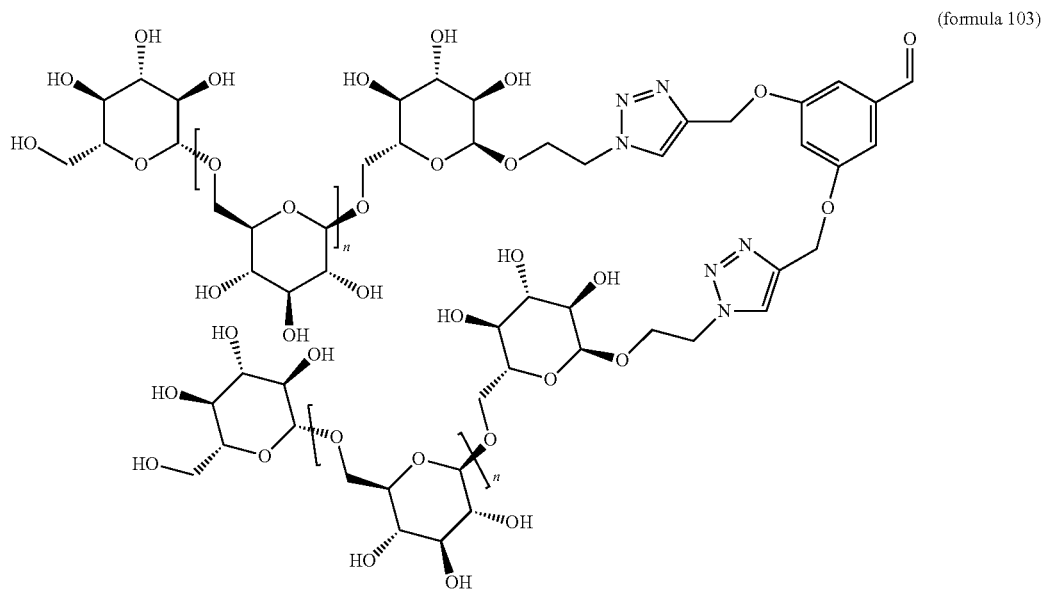

(formula 103)

103a. a 3mer (n=1): 3,5-bis(1[2-[O-β-D-glucopyranosyl-(1→6)-O-β-D-glucopyranosyl-(1→6)-α-D-glucopyranosyl]oxy]ethyl-1H-1,2,3-triazol-4-yl) methoxybenzaldehyde: theoretical m/z=1361 (M+H⁺);

103b. a 4mer (n=2): 3,5-bis(1-[2-[O-β-D-glucopyranosyl-(1→6)-O-β-D-glucopyranosyl-(1→6)-O-β-D-glucopyranosyl-(1→6)-α-D-glucopyranosyl]oxy]ethyl-1H-1,2,3-triazol-4-yl) methoxybenzaldehyd: theoretical m/z=1685 (M+H⁺);

103c. a 5mer (n=3): 3,5-bis(1-[2-[O-β-D-glucopyranosyl-(1→6)-O-β-D-glucopyranosyl-(1→6)-O-β-D-glucopyranosyl-(1→6)-O-β-D-glucopyranosyl-(1→6)-α-D-glucopyranosyl]oxy]ethyl-1H-1,2,3-triazol-4-yl) methoxybenzaldehyde: theoretical m/z=2009 (M+H⁺);

103d. a timer (n=4): 3,5-bis(1-[2-[O-β-D-glucopyranosyl-(1→6)-O-β-D-glucopyranosyl-(1→6)-O-β-D-glucopyranosyl-(1→6)-O-β-D-glucopyranosyl-(1→6)-O-β-D-glu- D-glucopyranosyl-(1→6)-α-D-glucopyranosyl]oxy]ethyl-1H-1,2,3-triazol-4-yl)methoxybenzaldehyde: theoretical m/z=2981 (M+H⁺); and 103g. a 9mer (n=7): 3,5-bis(1-[2-[O-β-D-glucopyranosyl-(1→6)-O-β-D-glucopyranosyl-(1→6)-O-β-D-glucopyranosyl-(1→6)-O-β-D-glucopyranosyl-(1→6)-O-β-D-glucopyranosyl-(1→6)-O-β-D-glucopyranosyl-(1→6)-O-β-D-glucopyranosyl-(1→6)-O-β-D-glucopyranosyl-(1→6)-α-D-glucopyranosyl]oxy]ethyl-1H-1,2,3-triazol-4-yl) methoxybenzaldehyde: theoretical m/z=3305 (M+H⁺).

Example 40

Aldol

7-[6-(O-β-D-glucopyranosyl-(1,6))₃ O-β-D-glucopyranosyl]-2-[3-[6-(O-(β-D-glucopyranosyl-(1,6))₃ O-β-D-glucopyranosyl]oxypropyl]hept-2-enal and 3-hydroxy-7-[6-(O-β-D-glucopyranosyl-(1,6))₃ O-β-D-glucopyranosyl]-2-[3-[6-(O-β-D-glucopyranosyl-(1,6))₂ O-β-D-glucopyranosyl]oxypropyl]heptane A solution of 1-O-β-(4-oxybutoxy)-6-O-[1-[O-β (2,3,4-tri-O-benzoyl)-D-glucopranosyl-(1,6)]₂-O-β-(2,3,4,6-tetra-O-benzoyl)-D-glucopranosyl]-D-glucopyranose-2,3,4-tri-O-benzoate (40 mg, 0.0.0190 mmol) in THF (0.500 mL) and MeOH (0.500 mL) was treated with NaOMe (0.5 M in MeOH, 0.057 mL, 0.0285 mmol). The reaction mixture was stirred at room temperature for 12 h. The reaction solvent was evaporated under vacuum with rotavapor and the residue was treated with ethyl acetate (5.0 mL) and filtered to afford a white solid. The solid was dissolved in aqueous 50% acetic acid (0.200 mL) and the mixture was stirred at 50° C.

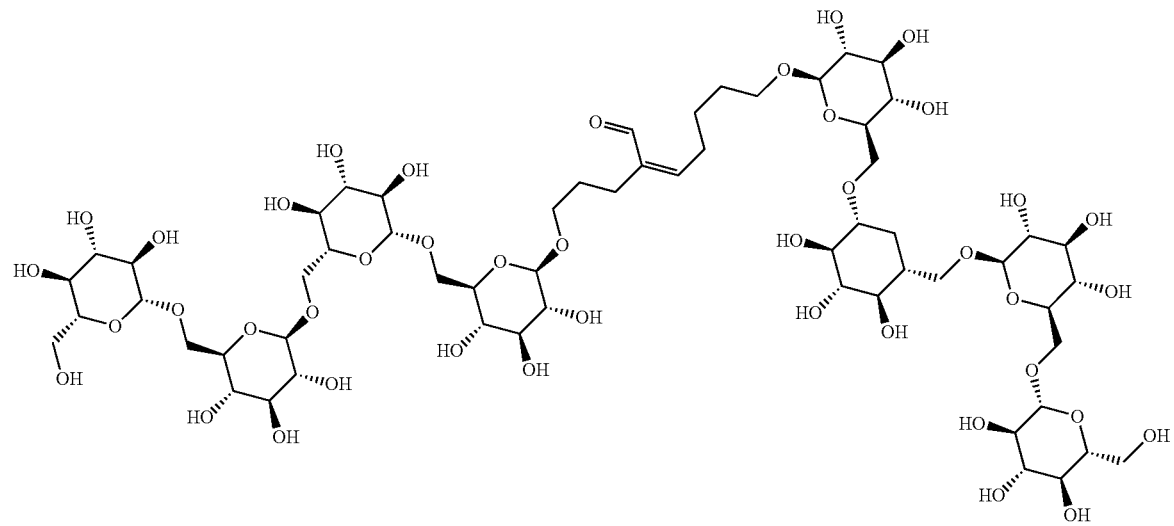

(formula 104)

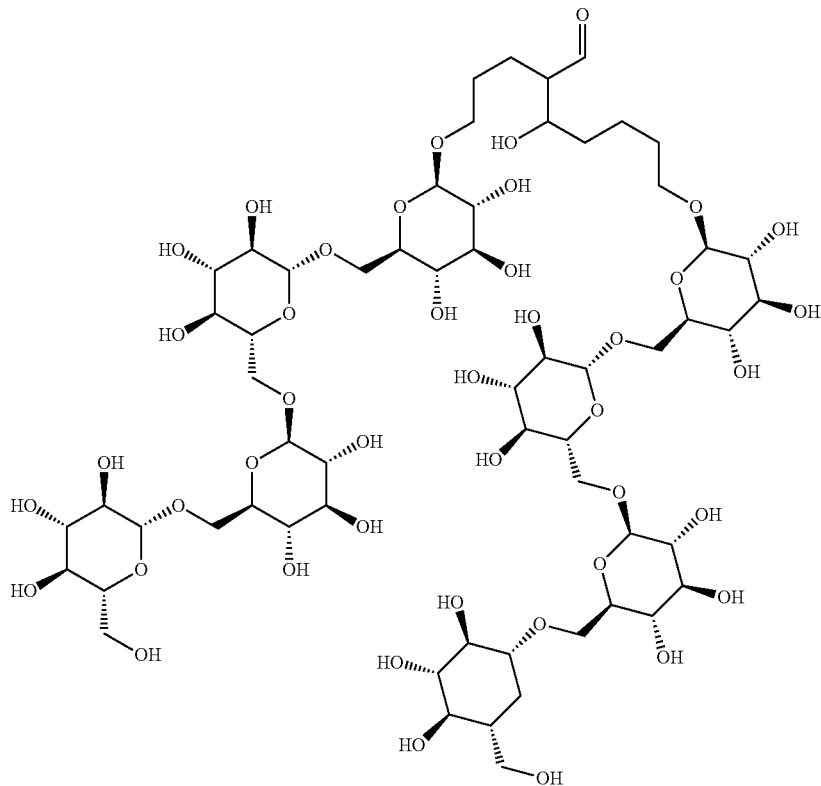

(formula 105)

for 2 h. The solvent was evaporated by lyophilization and the solid was purified by prepative HPLC on a Agilent Polaris A column (250×10.0 mm, 1-95% water/acetonitrile w/ 0.1% formic acid) to afford products 104 (2 mg) as a solid: m/z=1484 (M+H⁺) and 105 product (1 mg) as a solid: m/z=1501 (M+H⁺).

Similarly prepared by the method of this example are:

a. Compounds of Formula 104

104a. a 3mer: 7-[6-(O-β-D-glucopyranosyl-(1,6))$_2$ O-β-D-glucopyranosyl]-2-[3-[6-(O-β-D-glucopyranosyl-(1,6))$_2$ O-β-D-glucopyranosyl]oxypropyl]hept-2-enal: theoretical m/z=1160 (M+H⁺);

104b. a 5mer: 7-[6-(O-β-D-glucopyranosyl-(1,6))$_4$ O-β-D-glucopyranosyl]-2-[3-[6-(β-β-D-glucopyranosyl-(1,6))$_4$ O-β-D-glucopyranosyl]oxypropyl]hept-2-enal: theoretical m/z=1808 (M+H⁺);

104c. a 6mer: 7-[6-(O-β-D-glucopyranosyl-(1,6))$_4$ O-β-D-glucopyranosyl]-2-[3-[6-(O-β-D-glucopyranosyl-(1,6))$_5$ O-β-D-glucopyranosyl]oxypropyl]hept-2-enal: theoretical m/z=2132 (M+H⁺);

104d. a 7mer: 7-[6-(O-β-D-glucopyranosyl-(1,6))$_4$ O-β-D-glucopyranosyl]-2-[3-[6-(O-β-D-glucopyranosyl-(1,6))$_6$ O-β-D-glucopyranosyl]oxypropyl]hept-2-enal: theoretical m/z=2456 (M+H⁺);

104e. a 8mer: 7-[6-(O-β-D-glucopyranosyl-(1,6))$_4$ O-β-D-glucopyranosyl]-2-[3-[6-(O-β-D-glucopyranosyl-(1,6))$_7$ O-β-D-glucopyranosyl]oxypropyl]hept-2-enal: theoretical m/z=2780 (M+H⁺); and 104f. an 9mer: 7-[6-(O-β-D-glucopyranosyl-(1,6))$_4$ O-β-D-glucopyranosyl]-2-[3-[6-(O-β-D-glucopyranosyl-(1,6))$_8$ O-β-D-glucopyranosyl]oxypropyl]hept-2-enal: theoretical m/z=3104 (M+H⁺).

b. Compounds of Formula 105

105a. a 3mer: 3-hydroxy-7-[6-(O-β-D-glucopyranosyl-(1,6))$_2$ O-β-D-glucopyranosyl]-2-[3-[6-(O-β-D-glucopyranosyl-(1,6))$_2$ O-β-D-glucopyranosyl]oxypropyl]heptane: theoretical m/z=1177 (M+H⁺);

105b. a 5mer: 3-hydroxy-7-[6-(O-β-D-glucopyranosyl-(1,6))$_4$ O-β-D-glucopyranosyl]-2-[3-[6-(O-β-D-glucopyranosyl-(1,6))$_4$ O-β-D-glucopyranosyl]oxypropyl]heptane: theoretical m/z=1824 (M+H⁺);

105c. a 6mer: 3-hydroxy-7-[6-(O-β-D-glucopyranosyl-(1,6))$_5$ O-β-D-glucopyranosyl]-2-[3-[6-(O-β-D-glucopyranosyl-(1,6))$_5$ O-β-D-glucopyranosyl]oxypropyl]heptane: theoretical m/z=2148 (M+H⁺);

105d. a 7mer: 3-hydroxy-7-[6-(O-β-D-glucopyranosyl-(1,6))$_6$ O-β-D-glucopyranosyl]-2-[3-[6-(O-β-D-glucopyranosyl-(1,6))$_6$ O-β-D-glucopyranosyl]oxypropyl]heptane: theoretical m/z=2472 (M+H⁺);

105e. a 8mer: 3-hydroxy-7-[6-(O-β-D-glucopyranosyl-(1,6))$_7$ O-β-D-glucopyranosyl]-2-[3-[6-(O-β-D-glucopyranosyl-(1,6))$_7$ O-β-D-glucopyranosyl]oxypropyl]heptane: theoretical m/z=2796 (M+H⁺); and 105f. a 9mer: 3-hydroxy-7-[6-(O-β-D-glucopyranosyl-(1,6))$_8$ O-β-D-glucopyranosyl]-2-[3-[6-(O-β-D-glucopyranosyl-(1,6))$_8$ O-β-D-glucopyranosyl]oxypropyl]heptane: theoretical m/z=3120 (M+H⁺).

Example 41

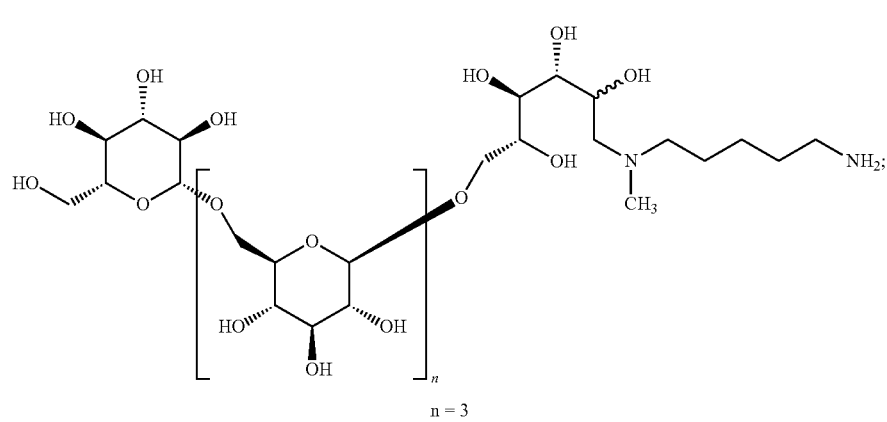

(formula 106)

n = 3

To a solution of product of Formula 16 (3.3 mg; see Example 9) was treated with TFA precooled to 0° C. to result in a total concentration of 75 mM. After 15 min at 0° C., the reaction was frozen via liquid nitrogen and the solvent was removed via a lypholizer. After the mixture was dried, the solid was resuspended in water (100 μL), and filtered through a 0.45 mm centrifugal filter and then re-lyphilized to afford the product (2.2 mg) as a solid; m/z=929 (M+H⁺); 951 (M+Na⁺);

The below compounds of formula 106 were prepared similarly.

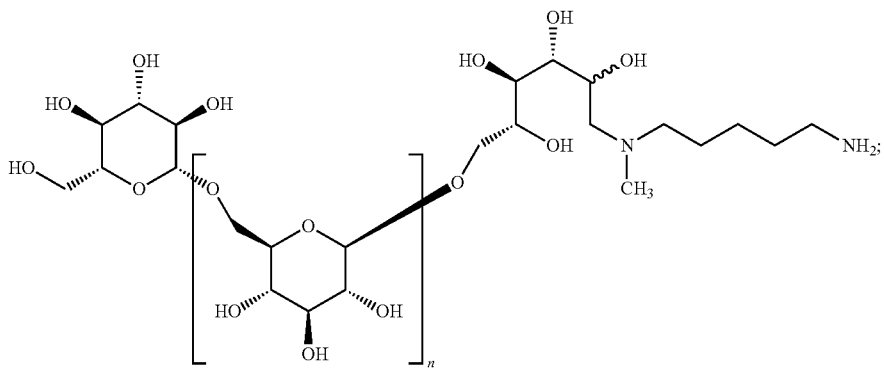

106a. a 3mer (n=2): [(2R,3R,4R,5RS)-2,3,4,5-tetrahydroxy-6-[(N-methyl-N-(5-aminopentyl))amino]hexyl [O-β-D-glucopyranosyl-1,6]$_2$-β-D-glucopyranoside: m/z=767 (M+H$^+$); 789 (M+Na$^+$);

106b. a 5mer (n=4): [(2R,3R,4R,5RS)-2,3,4,5-tetrahydroxy-6-[(N-methyl-N-(5-aminopentyl))amino]hexyl [O-β-D-glucopyranosyl-1,6]$_4$-β-D-glucopyranoside: m/z=1091 (M+H$^+$); 1113 (M+Na$^+$);

106c. a 6mer (n=5): [(2R,3R,4R,5RS)-2,3,4,5-tetrahydroxy-6-[(N-methyl-N-(5-aminopentyl))amino]hexyl [O-β-D-glucopyranosyl-1,6]$_5$-β-D-glucopyranoside: m/z=1253 (M+H$^+$); 1275 (M+Na$^+$); and 106d. a 7mer (n=6): [(2R,3R,4R,5RS)-2,3,4,5-tetrahydroxy-6-[(N-methyl-N-(5-aminopentyl))amino]hexyl [O-β-D-glucopyranosyl-1,6]$_6$-β-D-glucopyranoside: m/z=1415 (M+H$^+$) 1437 (M+Na$^+$);

The below compounds can be similarly prepared by the method of this example.

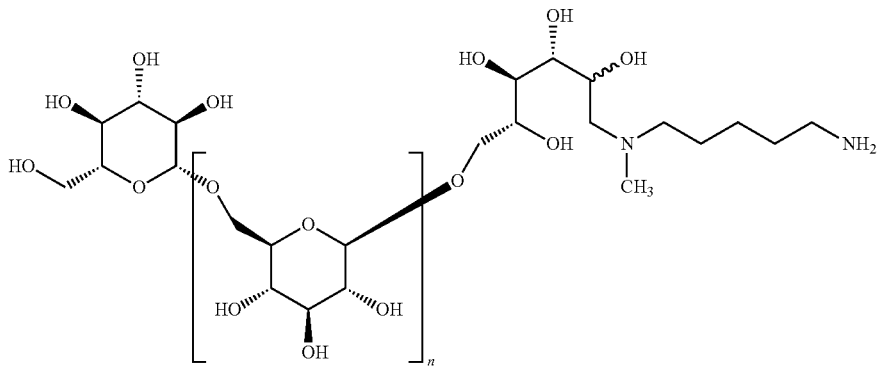

106e. an 8mer (n=7): [(2R,3R,4R,5RS)-2,3,4,5-tetrahydroxy-6-[(N-methyl-N-(5-aminopentyl))amino]hexyl [O-β-D-glucopyranosyl-1,6]$_7$-β-D-glucopyranoside: theoretical m/z=1515 (M+H$^+$); and 106f. a 9mer (n=8): [(2R,3R,4R,5RS)-2,3,4,5-tetrahydroxy-6-[(N-methyl-N-(5-aminopentyl))amino]hexyl [O-β-D-glucopyranosyl-1,6]$_8$-β-D-glucopyranoside: theoretical m/z=1677 (M+H$^+$).

Example 42

Binding of oligosaccharides to anti-β-1,6-glucan antibodies is performed as described in the following protocol.

I. Reagents
 1. Nunc 96 well flat bottom maxiSorp plate—0.4 mL/well (Thermo Scientific, cat #439454)
 2. PBS PH 7.2 (Gibco, cat #20012-027)
 3. Plate sealer VWR adhesive film for microplates (cat #60941-062)
 4. Casein in PBS (Thermo Scientific, cat #37528)
 5. Anti-β-1,6-Glucan IgG antibodies (affinity purified from IVIG, Baxter)
 6. Goat anti-human IgG (H&L)-HRP (Kpl cat #074-1006)
 7. 1-Step™ Ultra TMB—ELISA (Thermo Scientific cat #34028)
 8. PBS-Tween buffer (PH 7.2, 0.05% Tween 20, Kpl cat #51-12-01)

II. Method: Detection of Anti-Beta Glucan IgG by ELISA
 1. Coat plate with oligosaccharides in PBS overnight at 4° C.
 2. Wash 3 times with 250 uL of PBS-Tween
 3. Empty plate
 4. Block plate with 200 uL of Casein for 1 hour at room temperature
 5. Empty plate
 6. Add 40 ug/mL anti-Beta 1,6 Glucan IgG (4 ug/well) in Casein
 7. Incubate for 45 min at room temperature
 8. Wash 3 times with 250 uL of PBS-Tween
 9. Empty plate
 10. Add detection antibody: anti-human IgG-HRP at 1:5000—in casein. Incubate for 45 min at room temperature in the dark
 11. Wash 5 times with 250 uL of PBS-Tween
 12. Empty plate
 13. Add 100 uL of one step ultra TMB 14. Measure the absorbance at 620 nm every 1 min for 60 min Tables 1-3 provide ELISA assay data for certain glucan compounds. In these tables, a plus (+) sign indicates that the glucan was active in the assay, a minus (−) sign indicates that the glucan was not active, the "+/−" symbol indicates inconclusive results, and an empty cell indicates that the glucan was not tested.

TABLE 1

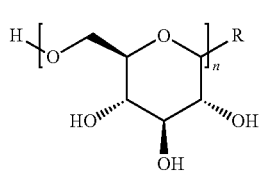

(formula 107)

| R group | Sugar Size (n =) | | | | | | | | | | |
|---|---|---|---|---|---|---|---|---|---|---|---|
|  | 2 | 3 | 4 | 5 | 6 | 7 | 8 | 9 | 10 | 11 | 12 |
| OH | + | + | + | + | + | + | + | + | + | + | + |
| OCH$_3$ |  | + | + | + | + | + | + | + | + | + |  |
| β-OCH(CN)Ph | − |  |  |  |  |  |  |  |  |  |  |
| α-O(CH$_2$)$_2$Cl |  | + | + | + | + | + | + | + |  |  |  |
| α-O(CH$_2$)$_2$N$_3$ |  | + | + | + | + | + | + | + |  |  |  |
| β-O(CH$_2$)$_2$N$_3$ |  |  | + | + | + |  |  |  |  |  |  |
| β-O(CH$_2$)$_4$C═O |  |  | + |  |  |  |  |  |  |  |  |
| β-O(CH$_2$)$_2$O(CH$_2$)$_2$C═O |  |  | + |  |  |  |  |  |  |  |  |

TABLE 2

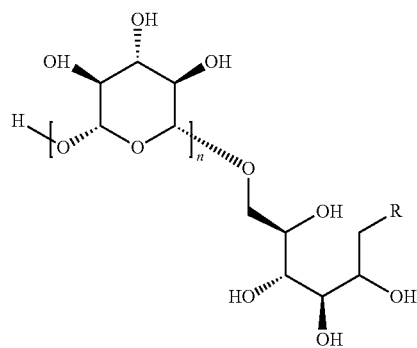

(formula 108)

| R group | Sugar Size (n =) | | | | |
|---|---|---|---|---|---|
|  | 3 | 4 | 5 | 6 | 7 |
| N(Me),N(CH$_2$)$_4$-BzOH |  | + | + | + |  |
| N(Me),N(CH$_2$)$_5$NH$_2$ | + | + | + | + | + |
| 4-piperidineCO$_2$H | + | + | + |  |  |
| 4-piperidine(CH$_2$)CO$_2$H | + | + | + |  |  |
| 3-pyrrolidineCO$_2$H | + | + | + |  |  |

TABLE 3

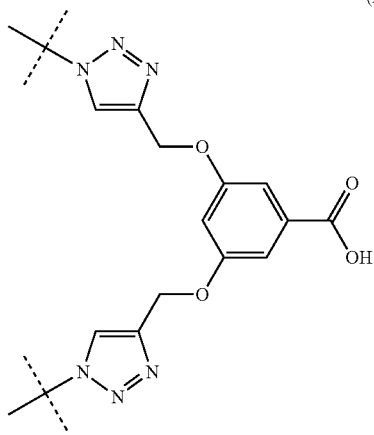

(formula 109)

| R group | Sugar Size (n =) | | | |
|---|---|---|---|---|
|  | 3 | 4 | 5 | 6 |
| (β-D-glucopyanosyl-1,6)$_n$α-O(CH$_2$)$_2$- | + | + |  |  |
| (β-D-glucopyanosyl-1,6)$_n$β-O(CH$_2$)$_2$- |  | + | + | + |

While we have described a number of embodiments of this invention, it is apparent that our basic examples may be altered to provide other embodiments, which utilize the compounds and methods of this invention. Therefore, it will be appreciated that the scope of this invention is to be defined by the appended claims rather than by the specific embodiments, which have been represented by way of example.

We claim:

1. A compound having a structure according to the following general formula (I),

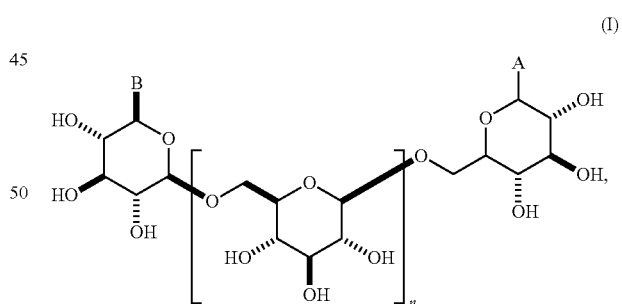

wherein n is an integer from 1 to 18;

B is —CH$_2$OH, —CHO, or —CO$_2$H;

A is α and is:

(a) —OR, wherein R is alkenyl, alkynyl, aryl, heteroaryl, or heteroaliphatic;

(b) —SR, wherein R is alkyl, alkenyl, alkynyl, aryl, heteroaryl, or heteroaliphatic;

(c) a 6-O-substituted-D-glucosamine (W),

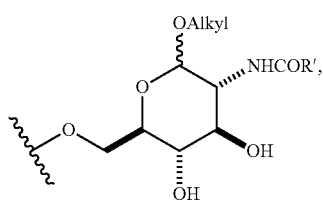

(W)

wherein
R' is alkyl, aryl, or heteroaryl;
(d) a 6-O-substituted-C-glycoside (X),

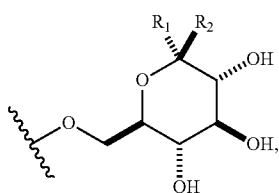

(X)

wherein
$R_1$ is H; and $R_2$ is alkenyl, alkynyl, or heteroaliphatic; or
$R_2$ is H; and $R_1$ is alkenyl, alkynyl, or heteroaliphatic; and
a is 0, 1, 2, 3, 4, or 5

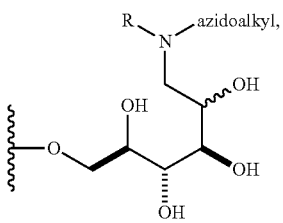

(e)

wherein
R is H, alkyl, or aryl, and
azidoalkvl is an alkyl group comprising an azide moiety;

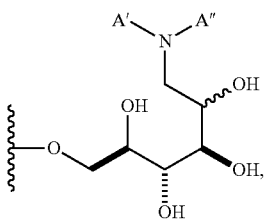

(f)

wherein
A' is alkyl, aryl, or heteroaryl; A" is carboxy alkyl, carboxy aryl, or carboxy heteroaryl; carboxy alkyl represents a residue formed from an aliphatic amino acid; carboxy aryl represents a residue formed from an aromatic amino acid; and carboxy heteroaryl represents a residue formed from a heteroaromatic amino acid;

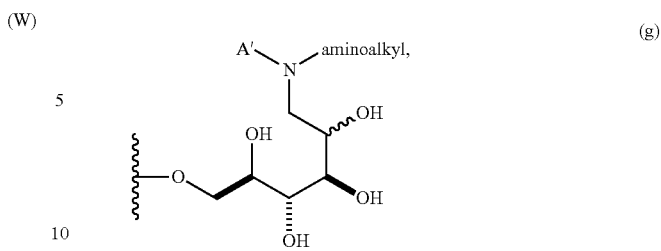

(g)

wherein
A' is alkyl, aryl, or heteroaryl; and aminoalkyl represents an alkyl group containing an amino moiety;

or

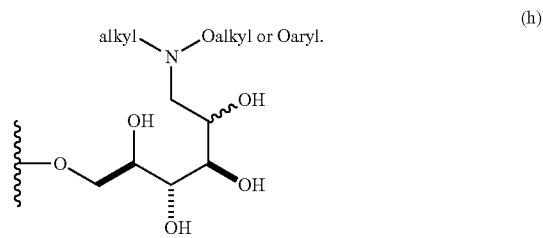

(h)

2. The compound of claim 1, wherein group A is —SR.

3. The compound of claim 1, wherein group A is —O(CH$_2$CH$_2$O)aCH$_2$CH$_2$N$_3$, wherein a is 0, 1, 2, 3, 4, or 5.

4. The compound of claim 1, wherein group A is a 6-O-substituted-D-glucosamine (W),

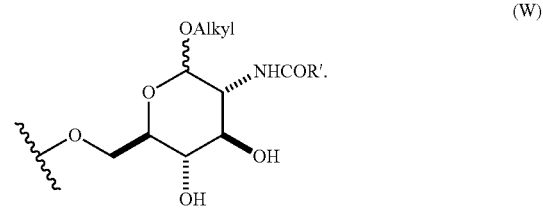

(W)

5. The compound of claim 1, wherein group A is

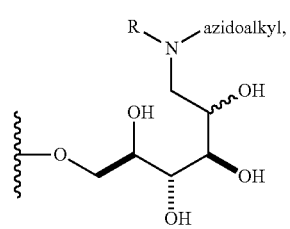

wherein R is H, alkyl, or aryl, and azidoalkyl is an alkyl group containing an azide moiety.

6. The compound of claim 5, wherein R is unsubstituted alkyl or substituted alkyl.

7. The compound of claim 1, wherein group A is

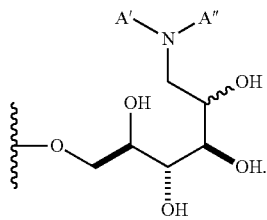

8. The compound of claim 7, wherein A' is alkyl or aryl; and
A" is carboxy alkyl.

9. The compound of claim 1, wherein group A is

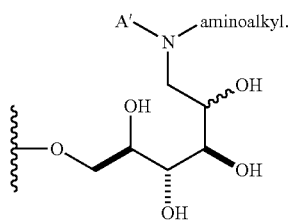

10. The compound of claim 1, wherein said compound has a structure according to formula (Ib), (Ib)

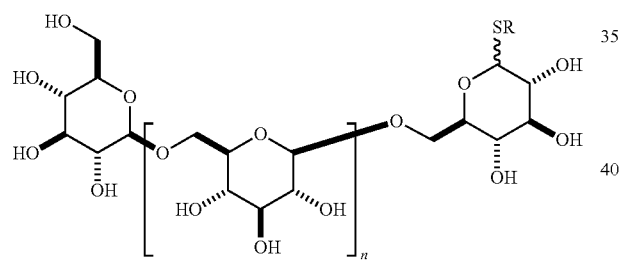

wherein
n is an integer between 1-18, and
R is selected from alkyl, alkenyl, alkynyl, alkylene, alkynylene, aryl, and heteroaryl.

11. A compound having a structure according to formula (Ic)

(Ic)

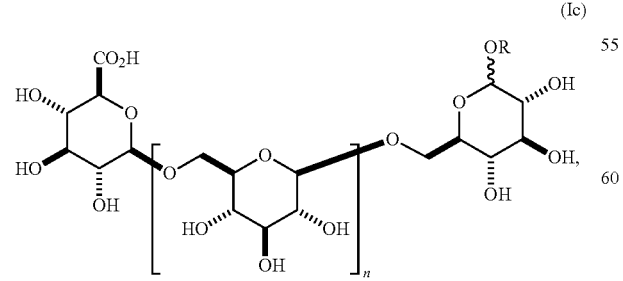

wherein n is an integer between 1-18, and
R is alkyl.

12. A compound having a structure according to formula (Id), (Id)

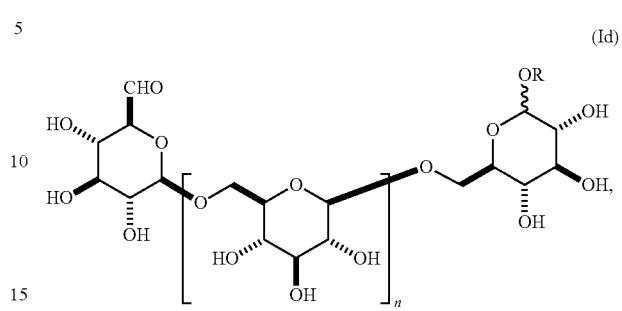

wherein n is an integer between 1-18, and
R is alkyl.

13. A compound having a structure according to the following general formula (I), (I)

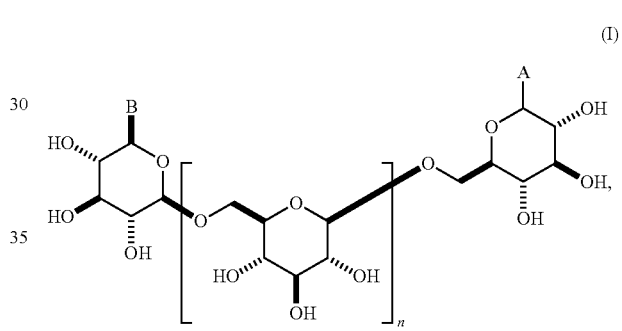

wherein
n is an integer from 1 to 18;
B is —CH$_2$OH, —CHO, or —CO$_2$H;
A is:
  (a) —SR, wherein R is alkyl, alkenyl, alkynyl, aryl, heteroaryl, or heteroaliphatic;
  (b) —O(CH$_2$CH$_2$O)aCH$_2$CH$_2$N$_3$, wherein a is 0, 1, 2, 3, 4, or 5;
  (c) a 6-O-substituted-D-glucosamine (W), (W)

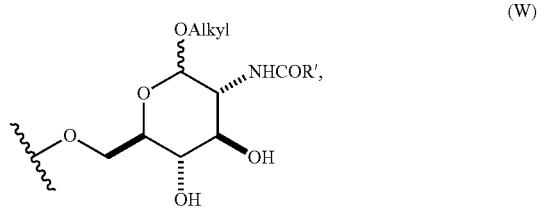

wherein
R' is alkyl, aryl, or heteroaryl;

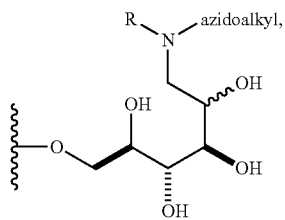 (d)

wherein
R is H, alkyl, or aryl, and
azidoalkyl is an alkyl group comprising an azide moiety;

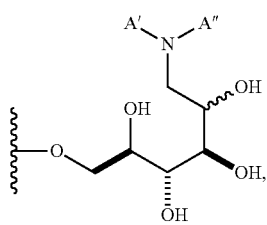 (e)

wherein
A' is alkyl, aryl, or heteroaryl; A" is carboxy alkyl, carboxy aryl, or carboxy heteroaryl; carboxy alkyl represents a residue formed from an aliphatic amino acid; carboxy aryl represents a residue formed from an aromatic amino acid; and carboxy heteroaryl represents a residue formed from a heteroaromatic amino acid;

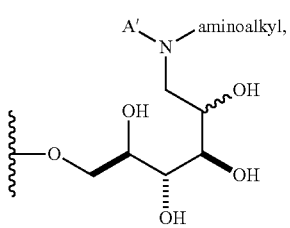 (f)

wherein
A' is alkyl, aryl, or heteroaryl; and aminoalkyl represents an alkyl group containing an amino moiety; or
(g) —O-alkyl, when B is —CHO, or —CO₂H.

14. The compound of claim 13, wherein A is β.
15. The compound of claim 13, wherein group A is

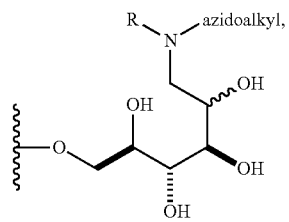

wherein R is H, alkyl, or aryl, and azidoalkyl is an alkyl group containing an azide moiety.

16. The compound of claim 15, wherein R is unsubstituted alkyl or substituted alkyl.
17. The compound of claim 13, wherein group A is

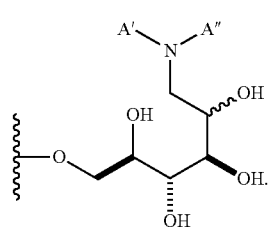

18. The compound of claim 17, wherein:
A' is alkyl or aryl; and
A" is carboxy alkyl.
19. The compound of claim 13, wherein group A is

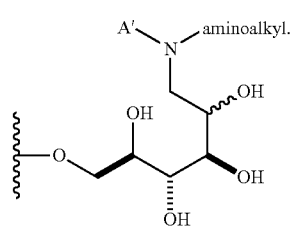

\* \* \* \* \*